US011723644B2

(12) United States Patent
Martinelli et al.

(10) Patent No.: US 11,723,644 B2
(45) Date of Patent: Aug. 15, 2023

(54) SURGICAL ACCESS SYSTEM AND RELATED METHODS

(71) Applicant: NuVasive, Inc., San Diego, CA (US)

(72) Inventors: Scot Martinelli, San Diego, CA (US);
Jared Arambula, San Diego, CA (US);
Eric Finley, San Diego, CA (US);
Patrick Miles, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 356 days.

(21) Appl. No.: 17/162,292

(22) Filed: Jan. 29, 2021

(65) Prior Publication Data
US 2021/0290216 A1 Sep. 23, 2021

Related U.S. Application Data

(63) Continuation of application No. 16/400,978, filed on May 1, 2019, now abandoned, which is a continuation
(Continued)

(51) Int. Cl.
*A61B 17/02* (2006.01)
*A61N 1/05* (2006.01)
(Continued)

(52) U.S. Cl.
CPC ............ *A61B 17/025* (2013.01); *A61B 5/389* (2021.01); *A61B 5/742* (2013.01); *A61B 17/02* (2013.01);
(Continued)

(58) Field of Classification Search
CPC .......... A61B 17/025; A61B 2017/0256; A61B 17/02; A61B 17/0206; A61B 5/0488; A61B 5/742; A61B 17/848; A61F 2/4611
(Continued)

(56) References Cited

U.S. PATENT DOCUMENTS 208,227 A 9/1878 Dorr
751,475 A 2/1904 De Vilbiss
(Continued)

FOREIGN PATENT DOCUMENTS

DE 299 08 259 7/1999
DE 20016971 1/2001
(Continued)

OTHER PUBLICATIONS

Anatomy of the Lumbar Spine in MED TM MicroEndoscopic Discectomy (1997, Ludann Grand Rapids MI), 14 pgs.
(Continued)

*Primary Examiner* — Matthew J Lawson
(74) *Attorney, Agent, or Firm* — Seager, Tufte & Wickhem, LLP

(57) ABSTRACT

A surgical access system including a tissue distraction assembly 40 and a tissue retraction assembly 10, both of which may be equipped with one or more. electrodes 23 for use in detecting the existence of (and optionally the distance and/or direction to) neural structures before, during, and after the establishment of an operative corridor 15 to a surgical target site. The tissue retraction assembly 10 has a plurality of blades 12, 16, 18 which may be introduced while in a closed configuration, after which point they may be opened to create an operation corridor 15 to the surgical target site, including pivoting at least one blade 12, 16, 18 to expand the operative corridor 15 adjacent to the operative site.

30 Claims, 49 Drawing Sheets

Related U.S. Application Data of application No. 15/484,871, filed on Apr. 11, 2017, now abandoned, which is a continuation of application No. 11/665,039, filed as application No. PCT/US2005/036454 on Oct. 11, 2005, now Pat. No. 9,622,732.

(60) Provisional application No. 60/720,710, filed on Sep. 26, 2005, provisional application No. 60/617,498, filed on Oct. 8, 2004.

(51) Int. Cl.
| | | |
|---|---|---|
| *A61F 2/46* | (2006.01) | |
| *A61N 1/36* | (2006.01) | |
| *A61B 5/389* | (2021.01) | |
| *A61F 2/44* | (2006.01) | |
| *A61B 5/00* | (2006.01) | |
| *A61B 17/84* | (2006.01) | |
| *A61B 17/00* | (2006.01) | |

(52) U.S. Cl.
CPC ...... *A61B 17/0206* (2013.01); *A61B 17/0218* (2013.01); *A61B 17/848* (2013.01); *A61F 2/4455* (2013.01); *A61F 2/4611* (2013.01); *A61N 1/0551* (2013.01); *A61N 1/36017* (2013.01); *A61B 2017/00022* (2013.01); *A61B 2017/00199* (2013.01); *A61B 2017/00407* (2013.01); *A61B 2017/0256* (2013.01); *A61B 2017/0262* (2013.01); *A61B 2505/05* (2013.01); *A61F 2002/4619* (2013.01); *A61N 1/36003* (2013.01)

(58) Field of Classification Search
USPC .......................................... 600/201–241, 244
See application file for complete search history.

(56) References Cited

U.S. PATENT DOCUMENTS

| | | |
|---|---|---|
| 972,983 A | 10/1910 | Arthur |
| 1,003,232 A | 10/1910 | Cerbo |
| 1,044,348 A | 6/1912 | Cerbo |
| 1,328,624 A | 1/1920 | Graham |
| 1,548,184 A | 8/1925 | Cameron |
| 1,796,072 A | 3/1931 | Baer |
| 2,300,040 A | 10/1942 | Betts |
| 2,320,709 A | 6/1943 | Arnesen |
| 2,594,086 A | 4/1952 | Smith |
| 2,704,064 A | 3/1955 | Fizzell et al. |
| 2,736,002 A | 2/1956 | Oriel |
| 2,807,259 A | 9/1957 | Guerriero |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Colyer |
| 3,747,592 A | 7/1973 | Santos |
| 3,752,149 A | 8/1973 | Ungar |
| 3,785,368 A | 1/1974 | McCarthy et al. |
| 3,789,829 A | 2/1974 | Hasson |
| 3,803,716 A | 4/1974 | Garnier |
| 3,830,226 A | 8/1974 | Staub et al. |
| 3,957,036 A | 5/1976 | Normann |
| 3,985,125 A | 10/1976 | Rose |
| D245,789 S | 9/1977 | Shea et al. |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,226,288 A | 10/1980 | Collins, Jr. |
| 4,235,242 A | 11/1980 | Howson et al. |
| 4,263,899 A | 4/1981 | Burgin |
| 4,285,347 A | 8/1981 | Hess |
| 4,291,705 A | 9/1981 | Severinghaus et al. |
| 4,449,532 A | 5/1984 | Storz |
| 4,461,300 A | 7/1984 | Christensen |
| 4,512,351 A | 4/1985 | Pohndorf |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,013 A | 6/1986 | Jones et al. |
| 4,595,018 A | 6/1986 | Rantala |
| 4,611,597 A | 9/1986 | Kraus |
| 4,616,635 A | 10/1986 | Caspar et al. |
| 4,633,889 A | 1/1987 | Talalla |
| 4,658,835 A | 4/1987 | Pohndorf |
| 4,716,901 A | 1/1988 | Jackson et al. |
| D295,445 S | 4/1988 | Freeman |
| 4,744,371 A | 5/1988 | Harris |
| 4,753,223 A | 6/1988 | Bremer |
| 4,759,377 A | 7/1988 | Dykstra |
| 4,765,311 A | 8/1988 | Kulik et al. |
| 4,784,150 A | 11/1988 | Voorhies et al. |
| 4,807,600 A | 2/1989 | Hayes |
| 4,807,642 A | 2/1989 | Brown |
| D300,561 S | 4/1989 | Asa et al. |
| 4,817,587 A | 4/1989 | Janese |
| 4,836,186 A | 6/1989 | Scholz |
| 4,862,891 A | 9/1989 | Smith |
| 4,892,105 A | 1/1990 | Prass |
| 4,913,134 A | 4/1990 | Luque |
| 4,917,274 A | 4/1990 | Asa et al. |
| 4,917,704 A | 4/1990 | Frey et al. |
| 4,926,865 A | 5/1990 | Oman |
| 4,950,257 A | 8/1990 | Hibbs et al. |
| 4,962,766 A | 10/1990 | Herzon |
| 4,964,411 A | 10/1990 | Johnson et al. |
| 4,989,587 A | 2/1991 | Farley |
| 5,007,902 A | 4/1991 | Witt |
| 5,015,247 A | 5/1991 | Michelson |
| 5,045,054 A | 9/1991 | Hood et al. |
| 5,052,373 A | 10/1991 | Michelson |
| 5,058,602 A | 10/1991 | Brody |
| 5,081,990 A | 1/1992 | Deletis |
| 5,088,472 A | 2/1992 | Fakhrai |
| 5,092,344 A | 3/1992 | Lee |
| 5,127,403 A | 7/1992 | Brownlee |
| 5,161,533 A | 11/1992 | Prass et al. |
| 5,171,279 A | 12/1992 | Mathews |
| 5,192,327 A | 3/1993 | Brantigan |
| 5,195,541 A | 3/1993 | Obenchain |
| 5,196,015 A | 3/1993 | Neubardt |
| 5,215,100 A | 6/1993 | Spitz et al. |
| RE34,390 E | 9/1993 | Culver |
| D340,521 S | 10/1993 | Heinzelman et al. |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,295,994 A | 3/1994 | Bonutti |
| 5,299,563 A | 4/1994 | Seton |
| 5,312,417 A | 5/1994 | Wilk |
| 5,313,956 A | 5/1994 | Knutsson et al. |
| 5,313,962 A | 5/1994 | Obenchain |
| 5,327,902 A | 7/1994 | Lemmen |
| 5,331,975 A | 7/1994 | Bonutti |
| 5,333,618 A | 8/1994 | Lekhtman et al. |
| 5,342,384 A | 8/1994 | Sugarbaker |
| 5,357,983 A | 10/1994 | Mathews |
| 5,375,067 A | 12/1994 | Berchin |
| 5,375,594 A | 12/1994 | Cueva |
| 5,377,667 A | 1/1995 | Patton et al. |
| 5,383,876 A | 1/1995 | Nardella |
| 5,395,317 A | 3/1995 | Kambin |
| 5,450,845 A | 9/1995 | Alexgaard |
| 5,472,426 A | 12/1995 | Bonati et al. |
| 5,474,057 A | 12/1995 | Makower et al. |
| 5,474,558 A | 12/1995 | Neubardt |

(56) References Cited

U.S. PATENT DOCUMENTS

| | | |
|---|---|---|
| 5,480,440 A | 1/1996 | Kambin |
| 5,482,038 A | 1/1996 | Ruff |
| 5,484,437 A | 1/1996 | Michelson |
| 5,487,739 A | 1/1996 | Aebischer et al. |
| 5,509,893 A | 4/1996 | Pracas |
| 5,512,038 A | 4/1996 | O'Neal et al. |
| 5,514,153 A | 5/1996 | Bonutti |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,569,290 A | 10/1996 | McAfee |
| 5,571,149 A | 11/1996 | Liss et al. |
| 5,579,781 A | 12/1996 | Cooke |
| 5,593,429 A | 1/1997 | Ruff |
| 5,599,279 A | 2/1997 | Slotman et al. |
| 5,630,813 A | 5/1997 | Kieturakis |
| 5,667,481 A | 9/1997 | Villalta et al. |
| 5,667,508 A | 9/1997 | Errico et al. |
| 5,671,752 A | 9/1997 | Sinderby et al. |
| 5,681,265 A | 10/1997 | Maeda et al. |
| 5,688,223 A | 11/1997 | Rosendahl |
| 5,707,359 A | 1/1998 | Bufalini |
| 5,711,307 A | 1/1998 | Smits |
| 5,728,046 A | 3/1998 | Mayer et al. |
| 5,741,253 A | 4/1998 | Michelson |
| 5,741,261 A | 4/1998 | Moskovitz et al. |
| 5,759,159 A | 6/1998 | Masreliez |
| 5,762,629 A | 6/1998 | Kambin |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,648 A | 7/1998 | Min |
| 5,785,658 A | 7/1998 | Benaron |
| 5,788,630 A | 8/1998 | Furnish |
| 5,792,044 A | 8/1998 | Foley et al. |
| 5,795,291 A | 8/1998 | Koros et al. |
| 5,797,854 A | 8/1998 | Hedgecock |
| 5,797,909 A | 8/1998 | Michelson |
| 5,814,073 A | 9/1998 | Bonutti |
| 5,830,151 A | 11/1998 | Hadzic et al. |
| 5,851,191 A | 12/1998 | Gozani |
| 5,853,373 A | 12/1998 | Griffith et al. |
| 5,860,973 A | 1/1999 | Michelson |
| 5,862,314 A | 1/1999 | Jeddeloh |
| 5,868,668 A | 2/1999 | Weiss |
| 5,872,314 A | 2/1999 | Clinton |
| 5,885,210 A | 3/1999 | Cox |
| 5,885,219 A | 3/1999 | Nightengale |
| 5,888,196 A | 3/1999 | Bonutti |
| 5,891,147 A | 4/1999 | Moskovitz et al. |
| 5,902,231 A | 5/1999 | Foley et al. |
| 5,928,139 A | 7/1999 | Koros et al. |
| 5,928,158 A | 7/1999 | Aristides |
| 5,931,777 A | 8/1999 | Sava |
| 5,935,131 A | 8/1999 | Bonutti et al. |
| 5,938,688 A | 8/1999 | Schiff |
| 5,944,658 A | 8/1999 | Koros et al. |
| 5,954,635 A | 9/1999 | Foley et al. |
| 5,976,094 A | 11/1999 | Gozani et al. |
| 5,993,385 A | 11/1999 | Johnston et al. |
| 6,004,262 A | 12/1999 | Putz et al. |
| 6,004,312 A | 12/1999 | Finneran |
| 6,004,341 A | 12/1999 | Zhu et al. |
| 6,007,487 A | 12/1999 | Foley et al. |
| 6,010,520 A | 1/2000 | Pattison |
| 6,024,696 A | 2/2000 | Hoftman et al. |
| 6,024,697 A | 2/2000 | Pisarik |
| 6,027,456 A | 2/2000 | Feler et al. |
| 6,038,469 A | 3/2000 | Karlsson et al. |
| 6,038,477 A | 3/2000 | Kayyali |
| 6,042,540 A | 3/2000 | Johnston et al. |
| 6,050,992 A | 4/2000 | Nichols |
| 6,074,343 A | 6/2000 | Nathanson et al. |
| 6,083,154 A | 7/2000 | Liu et al. |
| 6,095,987 A | 8/2000 | Schmulewitz |
| 6,096,046 A | 8/2000 | Weiss |
| 6,099,547 A | 8/2000 | Gellman et al. |
| 6,102,853 A | 8/2000 | Scirica et al. |
| 6,104,957 A | 8/2000 | Alo et al. |
| 6,104,960 A | 8/2000 | Duysens et al. |
| 6,120,436 A | 9/2000 | Anderson et al. |
| 6,120,503 A | 9/2000 | Michelson |
| 6,126,660 A | 10/2000 | Dietz |
| 6,132,386 A | 10/2000 | Gozani et al. |
| 6,132,387 A | 10/2000 | Gozani et al. |
| 6,135,965 A | 10/2000 | Tumer et al. |
| 6,139,493 A | 10/2000 | Koros et al. |
| 6,146,335 A | 11/2000 | Gozani |
| 6,152,871 A | 11/2000 | Foley et al. |
| 6,159,179 A | 12/2000 | Simonson |
| 6,161,047 A | 12/2000 | King et al. |
| 6,174,311 B1 | 1/2001 | Branch et al. |
| 6,181,961 B1 | 1/2001 | Prass |
| 6,196,969 B1 | 3/2001 | Bester et al. |
| 6,206,826 B1 | 3/2001 | Mathews et al. |
| 6,217,509 B1 | 4/2001 | Foley et al. |
| 6,224,545 B1 | 5/2001 | Cocchia et al. |
| 6,224,549 B1 | 5/2001 | Drongelen |
| 6,245,082 B1 | 6/2001 | Gellman et al. |
| 6,259,945 B1 | 7/2001 | Epstein et al. |
| 6,264,651 B1 | 7/2001 | Underwood et al. |
| 6,266,558 B1 | 7/2001 | Gozani et al. |
| 6,273,905 B1 | 8/2001 | Streeter |
| 6,287,322 B1 | 9/2001 | Zhu et al. |
| 6,292,701 B1 | 9/2001 | Prass et al. |
| 6,302,842 B1 | 10/2001 | Auerbach et al. |
| 6,306,100 B1 | 10/2001 | Prass |
| 6,308,712 B1 | 10/2001 | Shaw |
| 6,309,349 B1 | 10/2001 | Bertolero et al. |
| 6,312,392 B1 | 11/2001 | Herzon |
| 6,325,764 B1 | 12/2001 | Griffith et al. |
| 6,334,068 B1 | 12/2001 | Hacker |
| 6,348,058 B1 | 2/2002 | Melkent et al. |
| 6,360,750 B1 | 3/2002 | Gerber et al. |
| 6,371,968 B1 | 4/2002 | Kogasaka et al. |
| 6,395,007 B1 | 5/2002 | Bhatnagar et al. |
| 6,425,859 B1 | 7/2002 | Foley et al. |
| 6,425,887 B1 | 7/2002 | McGuckin et al. |
| 6,425,901 B1 | 7/2002 | Zhu et al. |
| 6,450,952 B1 | 9/2002 | Rioux et al. |
| 6,451,015 B1 | 9/2002 | Rittman et al. |
| 6,466,817 B1 | 10/2002 | Kaula et al. |
| 6,468,205 B1 | 10/2002 | Mollenauer et al. |
| 6,468,207 B1 | 10/2002 | Fowler, Jr. |
| 6,500,116 B1 | 12/2002 | Knapp |
| 6,500,128 B2 | 12/2002 | Marino |
| 6,520,907 B1 | 2/2003 | Foley et al. |
| 6,524,320 B2 | 2/2003 | DiPoto |
| 6,535,759 B1 | 3/2003 | Epstein et al. |
| 6,554,768 B1 | 4/2003 | Leonard |
| 6,564,078 B1 | 5/2003 | Marino et al. |
| 6,579,244 B2 | 6/2003 | Goodwin |
| 6,599,294 B2 | 7/2003 | Fuss et al. |
| 6,620,157 B1 | 9/2003 | Dabney et al. |
| 6,645,194 B2 | 11/2003 | Briscoe et al. |
| 6,679,833 B2 | 1/2004 | Smith |
| 6,712,795 B1 | 3/2004 | Cohen |
| 6,719,692 B2 | 4/2004 | Kleffner et al. |
| 6,760,616 B2 | 7/2004 | Hoey et al. |
| 6,770,074 B2 | 8/2004 | Michelson |
| 6,796,985 B2 | 9/2004 | Bolger et al. |
| 6,810,281 B2 | 10/2004 | Brock et al. |
| 6,819,956 B2 | 11/2004 | DiLorenzo |
| 6,829,508 B2 | 12/2004 | Schulman et al. |
| 6,847,849 B2 | 1/2005 | Mamo et al. |
| 6,849,047 B2 | 2/2005 | Goodwin |
| 6,851,430 B2 | 2/2005 | Tsou |
| 6,855,105 B2 | 2/2005 | Jackson, III et al. |
| 6,860,850 B2 | 3/2005 | Phillips et al. |
| 6,869,398 B2 | 3/2005 | Obenchain |
| 6,871,099 B1 | 3/2005 | Whitehurst et al. |
| 6,902,569 B2 | 6/2005 | Parmer et al. |

(56) References Cited

U.S. PATENT DOCUMENTS

| | | |
|---|---|---|
| 6,916,330 B2 | 7/2005 | Simonson |
| 6,926,728 B2 | 8/2005 | Zucherman et al. |
| 6,929,606 B2 | 8/2005 | Ritland |
| 6,945,933 B2 | 9/2005 | Branch |
| 6,951,538 B2 | 10/2005 | Ritland |
| 7,047,082 B1 | 5/2006 | Schrom et al. |
| 7,050,848 B2 | 5/2006 | Hoey et al. |
| 7,079,883 B2 | 7/2006 | Marino et al. |
| 7,089,059 B1 | 8/2006 | Pless |
| 7,177,677 B2 | 2/2007 | Kaula et al. |
| 7,198,598 B2 | 4/2007 | Smith et al. |
| 7,207,949 B2 | 4/2007 | Miles et al. |
| 7,226,451 B2 | 6/2007 | Shluzas et al. |
| 7,261,688 B2 | 8/2007 | Smith et al. |
| 7,435,219 B2 | 10/2008 | Kim |
| 7,470,236 B1 | 12/2008 | Kelleher et al. |
| 7,473,222 B2 | 1/2009 | Dewey et al. |
| 7,481,766 B2 | 1/2009 | Lee et al. |
| 7,522,953 B2 | 4/2009 | Kaula et al. |
| 7,556,601 B2 | 7/2009 | Branch et al. |
| 7,582,058 B1 | 9/2009 | Miles et al. |
| 7,643,884 B2 | 1/2010 | Pond et al. |
| 7,691,057 B2 | 4/2010 | Miles et al. |
| 7,693,562 B2 | 4/2010 | Marino et al. |
| 7,717,959 B2 | 5/2010 | William et al. |
| 7,819,801 B2 | 10/2010 | Miles et al. |
| 7,935,051 B2 | 5/2011 | Miles et al. |
| 8,000,782 B2 | 8/2011 | Gharib et al. |
| 8,005,535 B2 | 8/2011 | Gharib et al. |
| 8,021,430 B2 | 9/2011 | Michelson |
| 8,133,173 B2 | 3/2012 | Miles et al. |
| 8,192,356 B2 | 6/2012 | Miles et al. |
| 8,251,997 B2 | 8/2012 | Michelson |
| 8,303,458 B2 | 11/2012 | Fukano et al. |
| 8,343,046 B2 | 1/2013 | Miles et al. |
| 8,343,224 B2 | 1/2013 | Lynn et al. |
| 8,388,527 B2 | 3/2013 | Miles |
| 2001/0039949 A1 | 11/2001 | Loubser |
| 2001/0056280 A1 | 12/2001 | Underwood et al. |
| 2002/0007129 A1 | 1/2002 | Marino |
| 2002/0010392 A1 | 1/2002 | Desai |
| 2002/0072686 A1 | 6/2002 | Hoey et al. |
| 2002/0077632 A1 | 6/2002 | Tsou |
| 2002/0111538 A1 | 8/2002 | Wright et al. |
| 2002/0123744 A1 | 9/2002 | Reynard |
| 2002/0123780 A1 | 9/2002 | Grill et al. |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0070682 A1 | 4/2003 | Wilson et al. |
| 2003/0083688 A1 | 5/2003 | Simonson |
| 2003/0105503 A1 | 6/2003 | Marino |
| 2003/0139648 A1 | 7/2003 | Foley et al. |
| 2003/0149341 A1 | 8/2003 | Clifton |
| 2003/0225405 A1 | 12/2003 | Weiner |
| 2003/0236544 A1 | 12/2003 | Lunsford et al. |
| 2004/0087833 A1 | 5/2004 | Bauer et al. |
| 2004/0199084 A1 | 10/2004 | Kelleher et al. |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0080320 A1 | 4/2005 | Lee et al. |
| 2005/0096508 A1 | 5/2005 | Valentini et al. |
| 2005/0113644 A1 | 5/2005 | Obenchain et al. |
| 2005/0149035 A1 | 7/2005 | Pimenta et al. |
| 2005/0159650 A1 | 7/2005 | Ramond et al. |
| 2005/0182454 A1 | 8/2005 | Gharib et al. |
| 2005/0192575 A1 | 9/2005 | Pacheco |
| 2005/0215866 A1 | 9/2005 | Kim et al. |
| 2006/0025656 A1 | 2/2006 | Buckner et al. |
| 2006/0025703 A1 | 2/2006 | Miles et al. |
| 2006/0052672 A1 | 3/2006 | Landry et al. |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2007/0016097 A1 | 1/2007 | Farquhar et al. |
| 2007/0198062 A1 | 8/2007 | Miles et al. |
| 2007/0293782 A1 | 12/2007 | Marino |
| 2008/0058606 A1 | 3/2008 | Miles et al. |
| 2008/0058838 A1 | 3/2008 | Steinberg |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0097164 A1 | 4/2008 | Miles et al. |
| 2008/0300465 A1 | 12/2008 | Feigenwinter et al. |
| 2009/0124860 A1 | 5/2009 | Miles et al. |
| 2009/0138050 A1 | 5/2009 | Ferree |
| 2009/0192403 A1 | 7/2009 | Gharib et al. |
| 2009/0204016 A1 | 8/2009 | Gharib et al. |
| 2010/0069783 A1 | 3/2010 | Miles et al. |
| 2010/0130827 A1 | 5/2010 | Pimenta et al. |
| 2010/0152603 A1 | 6/2010 | Miles et al. |
| 2010/0160738 A1 | 6/2010 | Miles et al. |
| 2010/0174146 A1 | 7/2010 | Miles |
| 2010/0174148 A1 | 7/2010 | Miles et al. |
| 2012/0238822 A1 | 9/2012 | Miles et al. |

FOREIGN PATENT DOCUMENTS

| | | |
|---|---|---|
| DE | 100 48 790 | 4/2002 |
| EP | 0 334 116 | 9/1989 |
| EP | 0 567 424 | 10/1993 |
| EP | 0455282 | 12/1994 |
| EP | 0 972 538 | 1/2000 |
| EP | 1 002 500 | 5/2000 |
| EP | 1192905 | 4/2002 |
| FR | 613642 | 11/1926 |
| FR | 2702364 | 3/1993 |
| FR | 2 795 624 | 1/2001 |
| JP | 793186 | 5/1990 |
| JP | 10-14928 | 3/1996 |
| KR | 3019990007098 | 11/1999 |
| RU | 2019136 | 9/1994 |
| RU | 2192177 | 6/2000 |
| RU | 2157656 | 10/2000 |
| WO | 93/20741 | 10/1993 |
| WO | 94/28824 | 12/1994 |
| WO | 97/00702 | 1/1997 |
| WO | 98/23324 | 6/1998 |
| WO | 99/52446 | 10/1999 |
| WO | 00/27291 | 5/2000 |
| WO | 00/38574 | 7/2000 |
| WO | 00/44288 | 8/2000 |
| WO | 00/66217 | 11/2000 |
| WO | 00/67645 | 11/2000 |
| WO | 01/08563 | 2/2001 |
| WO | 01/37728 | 5/2001 |
| WO | 01/60263 | 8/2001 |
| WO | 02/054960 | 7/2002 |
| WO | 02/058780 | 8/2002 |
| WO | 02/71953 | 9/2002 |
| WO | 02/87678 | 11/2002 |
| WO | 03/005887 | 1/2003 |
| WO | 03/026482 | 4/2003 |
| WO | 03/037170 | 5/2003 |
| WO | 05/013805 | 2/2005 |
| WO | 05/030318 | 4/2005 |
| WO | 06/042241 | 4/2006 |
| WO | 06/066217 | 6/2006 |

OTHER PUBLICATIONS

Dirksmeier et al., "Microendoscopic and Open Laminotomy and Discectomy in Lumbar Disc Disease" *Seminars in Spine Surgery*, 1999, 11(2): 138-146.

METRx Delivered Order Form, 1999, 13 pages.

Medtronic Sofamor Danek "METRx™ MicroDiscectomy System," *Medtronic Sofamor Danek USA*, 21 pgs.

Medtronic Sofamor Danek "METRx System Surgical Technique," 2004, 22 pages.

(56) References Cited

OTHER PUBLICATIONS

"MetRx System MicroEndoscopic Discectomy: An Evolution in Minimally Invasive Spine Surgery," *Sofamor Danek*, 1999, 6 pages.
Smith and Foley "MetRx System MicroEndoscopic Discectomy: Surgical Technique" *Medtronic Sofamor Danek*, 2000, 24 pages.
"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.
Japanese Patent Office JP Patent Application No. 2006-528306 Office Action with English Translation, Jun. 10, 2009, 4 pages.
Plaintiffs' Preliminary Invalidity Contentions re U.S. Pat. Nos. 7,207,949; 7,470,236 and 7,582,058, Sep. 18, 2009, 19 pages.
Plaintiffs' Preliminary Invalidity Contentions—Appendices, Sep. 18, 2009, 191 pages.
Plaintiffs' Supplemental Preliminary Invalidity Contentions re U.S. Pat. Nos. 7,207,949, 7,470,236, arid 7,582,058, Sep. 29, 2009, 21 pages.
Plaintiffs' Supplemental Preliminary Invalidity Contentions—Appendices, Sep. 29, 2009, 294 pages.
Axon 501(k) Notification: Epoch 2000 Neurologica Workstation, Dec. 3, 1997, 464 pages.
Foley and Smith, "Microendoscopic Discectomy," *Techniques in Neurosurgery*, 1997, 3(4):301-307.
Medtronic Sofamor Danek "UNION™ / UNION-L™ Anterior & Lateral Impacted Fusion Devices: Clear choice of stabilization," *Medtronic Sofamor Danek*, 2000, 4 pages.
NuVasive Vector™ Cannulae, 2000, 1 page.
NuVasive Triad™ Tri-Columnar Spinal EndoArthrodesis™ via Minimally Invasive Guidance, 2000, 1 page (prior to Sep. 25, 2003).
NuVasive Triad™ Cortical Bone Allografl, 2000, 1 page (prior to Sep. 25, 2003).
NuVasive Vertebral Body Access System, 2000, 1 page.
Marina, "New Technology for Guided Navigation with Real Time Nerve Surveillance for Minimally Invasive Spine Discectomy & Arthrodesis," *Spineline*, 2000, p. 39.
NuVasive "INS-1 Screw Test," 2001, 10 pages.
NuVasive letter re 510k Neuro Vision JJB System, Oct. 16, 2001, 5 pages.
NuVasive letter re 510k Guided Arthroscopy System, Oct. 5, 1999, 6 pages.
NuVasive letter re 510k INS-1 Intraoperative Nerve Surveillance System, Nov. 13, 2000, 7 pages.
"NuVasiveTM Receives Clearance to Market Two Key Elem Minimally Invasive Spine Surgery System," Nov. 27, 2001, 20 pages.
Schick et al., "Microendoscopic lumbar discectomy versus open surgery: an intraoperative EMG study," *Eur Spine J*, 2002, 11: 20-26.
NuVasive letter re: 510(k) for Neurovision JJB System (Summary), Sep. 25, 2001, 28 pages.
NuVasive letter re: Special 510(k) Premarket Notification: Neurovision JJB System (Device Description), Jul. 3, 2003, 18 pages.
NuVasive letter re: Special 510(k) Premarket Notification: Neurovision JJB System (Device Description), Mar. 1, 2004, 16 pages.
NuVasive letter re: Special 510(k) Premarket Notification: Neurovision JJB System (Device Description), May 26, 2005, 17 pages.
NuVasive letter re: 510(k) Premarket Notification: Neurovision JJB System (Device Description), Jun. 24, 2005, 16 pages.
NuVasive letter re: Special 510(k) Premarket Notification: Neurovision JJB System (Device Description), Sep. 14, 2006, 17 pages.
NuVasive 510(k) Premarket Notification: Neurovision JJB System (Device Description), Aug. 20, 2007, 8 pages.
NuVasive letter re: 510(k) Premarket Notification: Guided Spinal Arthroscopy System (Device Description), Feb. 1, 1999, 40 pages.
NuVasive 510(k) Premarket Notification: Spinal System (Summary), Apr. 12, 2004, 10 pages.
NuVasive 510(k) Summary NIM Monitor, Sep. 4, 1998, 4 pages.
NuVasive correspondence re 510(k) Premarket Notification INS-1 Intraoperative Nerve Surveillance System: Section IV Device Description, pp. 12-51 (prior to Sep. 25, 2003).
Isley et al., "Recent Advances in Intraoperative Neuromonitoring of Spinal Cord Function: Pedicle Screw Stimulation Techniques," *American Journal of Electroneurodiagnostic Technology*, Jun. 1997, 37(2): 93-126.
Mathews et al., "Laparoscopic Discectomy with Anterior Lumbar Interbody Fusion," *Spine*, 1995, 20(16): 1797-1802.
Rose et al., "Persistently Electrified Pedicle Stimulation Instruments in Spinal Instrumentation: Techniques and Protocol Development," *Spine*, 1997, 22(3): 334-343.
"Electromyography System," International Search report from International Application No. PCT/US00/32329, Apr. 27, 2001, 9 pages.
"Nerve Proximity and Status Detection System and Method," International Search Report from International Application No. PCT/US01/18606, dated Oct. 18, 2001, 6 pages.
"Relative Nerve Movement and Status Detection System and Method," International Search Report from International Application No. PCT/US01/18579, dated Jan. 15, 2002, 6 pages.
"System and Method for Determining Nerve Proximity Direction and Pathology During Surgery," International Search Report from International Application No. PCT/US02/22247, dated Mar. 27, 2003, 4 pages.
"System and Methods for Determining Nerve Direction to a Surgical Instrument," International Search Report from International Application No. PCT/US03/02056, dated Aug. 12, 2003, 5 pages.
"Systems and Methods for Performing Percutaneous Pedicle Integrity Assessments," International Search Report from International Application No. PCT/US02/35047, dated Aug. 11, 2003, 5 pages.
"Systems and Methods for Performing Surgery Procedures and Assessments," International Search Report from International Application No. PCT/US02/30617, dated Jun. 5, 2003, 4 pages.
Lenke et al., "Triggered Electromyographic Threshold for Accuracy of Pedicle Screw Placement," *Spine*, 1995, 20(4): 1585-1591.
"Brackmann II EMG System," *Medical Electronics*, 1999, 4 pages.
"Neurovision SE Nerve Locator/Monitor", RLN Systems Inc. Operators Manual, 1999, 22 pages.
"The Brackmann II EMG Monitoring System," Medical Electronics Co. Operator's Manual Version 1.1, 1995, 50 pages.
"The Nicolet Viking IV," Nicolet Biomedical Products, 1999, 6 pages.
Anderson et al., "Pedicle screws with high electrical resistance: a potential source of error with stimulus-evoked EMG," *Spine*, Department of Orthopaedic Surgery University of Virginia, Jul. 15, 2002, 27(14): 1577-1581.
Bose et al., "Neurophysiologic Monitoring of Spinal Nerve Root Function During Instrumented Posterior Lumbar Spine Surgery," *Spine*, 2002, 27(13):1444-1450.
Calancie et al., "Stimulus-Evoked EMG Monitoring During Transpedicular Lumbosacral Spine Instrumentation" *Spine*, 1994, 19(24): 2780-2786.
Clements et al., "Evoked and Spontaneous Electromyography to Evaluate Lumbosacral Pedicle Screw Placement," *Spine*, 1996, 21(5): 600-604.
Danesh-Clough et al. ,"The Use of Evoked EMG in Detecting Misplaced Thoracolumbar Pedicle Screws," *Spine*, Orthopaedic Department Dunedin Hospital, Jun. 15, 2001, 26(12): 1313-1316.
Darden et al., "A Comparison of Impedance and Electromyogram Measurements in Detecting the Presence of Pedicle Wall Breakthrough," *Spine*, Charlotte Spine Center North Carolina, Jan. 15, 1998, 23(2): 256-262.
Ebraheim et al., "Anatomic Relations Between the Lumbar Pedicle and the Adjacent Neural Structures," *Spine*, Department of Orthopaedic Surgery Medical College of Ohio, Oct. 15, 1997, 22(20): 2338-2341.
Ford et al. "Electrical Characteristics of Peripheral Nerve Stimulators Implications for Nerve Localization," *Regional Anesthesia*, 1984, 9: 73-77.
Glassman et al., "A Prospective Analysis of Intraoperative Electromyographic Monitoring of Pedicle Screw Placement With Computed Tomographic Scan Confirmation," *Spine*, 1995, 20(12): 1375-1379.
Greenblatt et al., "Needle Nerve Stimulator-Locator: Nerve Blocks with a New Instrument for Locating Nerves," *Anesthesia& Analgesia*, 1962, 41(5): 599-602.

(56) References Cited

OTHER PUBLICATIONS

Haig, "Point of view," *Spine*, 2002, 27(24): 2819.
Haig et al., "The Relation Among Spinal Geometry on MRI, Paraspinal Electromyographic Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.
Holland et al., "Higher Electrical Stimulus Intensities are Required to Activate Chronically Compressed Nerve Roots: Implications for Intraoperative Electromyographic Pedicle Screw Testing," *Spine*, Department of Neurology, Johns Hopkins University School of Medicine, Jan. 15, 1998, 23(2): 224-227.
Holland, "Intraoperative Electromyography During Thoracolumbar Spinal Surgery," *Spine*, 1998, 23(17): 1915-1922.
Journee et al., "System for Intra-Operative Monitoring of the Cortical Integrity of the Pedicle During Pedicle Screw Placement in Low-Back Surgery: Design and Clinical Results," *Sensory and Neuromuscular Diagnostic Instrumentation and Data Analysis I, 18th Annual International Conference on Engineering in Medicine and Biology Society*, Amsterdam, 1996, pp. 144-145.
Maguire et al., "Evaluation of Intrapedicular Screw Position Using Intraoperative Evoked Electromyography," *Spine*, 1995, 20(9): 1068-1074.
Martin et al. "Initiation of Erection and Semen Release by Rectal Probe Electrostimulation (RPE)," *The Journal of Urology*, The Williams& Wilkins Co., 1983, 129: 637-642.
Minahan et al., "The Effect of Neuromuscular Blockade on Pedicle Screw Stimulation Thresholds" *Spine*, Department of Neurology, Johns Hopkins University School of Medicine, Oct. 1, 2000, 25(19): 2526-2530.
Pither et al., "The Use of Peripheral Nerve Stimulators for Regional Anesthesia: Review of Experimental Characteristics Technique and Clinical Applications," *Regional Anesthesia*, 1985, 10:49-58.
Raj et al., "Infraclavicular Brachial Plexus Block—A New Approach" *Anesthesia and Analgesia*, 1973, (52)6: 897-904.
Raj et al., "The Use of Peripheral Nerve Stimulators for Regional Anesthesia," *Clinical Issues in Regional Anesthesia*, 1985, 1(4):1-6.
Raj et al., "Use of the Nerve Stimulator for Peripheral Blocks," *Regional Anesthesia*, Apr.-Jun. 1980, pp. 14-21.
Raymond et al., "The Nerve Seeker: A System for Automated Nerve Localization," *Regional Anesthesia*, 1992, 17(3): 151-162.
Shafik, "Cavernous Nerve Simulation through an Extrapelvic Subpubic Approach: Role in Penile Erection," *Eur. Urol*, 1994, 26: 98-102.
Toleikis et al., "The Usefulness of Electrical Stimulation for Assessing Pedicle Screw Replacements," *Journal of Spinal Disorder*, 2000, 13(4): 283-289.
Medtronic Sofamor Danek "UNION™ / UNION-L™ Anterior & Lateral Impacted Fusion Devices: Surgical Technique" *Medtronic Sofamor Danek*, 2001, 20 pages.
Defendant's Disclosure of Asserted Claims and Preliminary Infringement Contentions Regarding U.S. Pat. Nos. 7,207,949; 7,470,236 and 7,582,058, Aug. 31, 2009, 21 pages.
Bergey et al., "Endoscopic Lateral Transpsoas Approach to the Lumbar Spine," *Spine*, 2004, 29(15): 1681-1688.
Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.
Gardocki, "Tubular diskectomy minimizes collateral damage: A logical progression moves spine surgery forward," *AAOS Now*, 2009, 5 pages.
Hovorka et al., "Five years' experience of retroperitoneal lumbar and thoracolumbar surgery," *Eur Spine J.*, 2000, 9(1): S30-S34.
Kossmann et al., "The use of a retractor system (SynFrame) for open, minimal invasive reconstruction of the anterior column of the thoracic and lumbar spine," *Eur Spine J.*, 2001, 10: 396-402.
Mayer, "A New Microsurgical Technique for Minimally Invasive Anterior Lumbar Interbody Fusion," *Spine*, 1997, 22(6): 691-699.
Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.
McAfee et al., "Minimally Invasive Anterior Retroperitoneal Approach to the Lumbar Spine: Emphasis on the Lateral BAK," *Spine*, 1998, 23(13): 1476-1484.
Rao, et al. "Dynamic retraction of the psoas muscle to expose the lumbar spine using the retroperitoneal approach," *J. Neurosurg Spine*, 2006, 5: 468-470.
Wolfla et al., "Retroperitoneal lateral lumbar interbody fusion with titanium threaded fusion cages," *J. Neurosurg (Spine 1)*, 2002, 96: 50-55.
Larson and Maiman, "Surgery of the Lumbar Spine," Thieme Medical Publishers, Inc., 1999, pp. 305-319.
Medtronic Xomed Surgical Products, Inc., NIM-Response Nerve Integrity Monitor Intraoperative EMG Monitor User's Guide, Revision B, 2000, 47pages.
"NuVasive's spine surgery system cleared in the US," Pharrn & Medical Industry Week, Dec. 10, 2001, 1 page.
Pimenta, "Initial Clinical Results of Direct Lateral, Minimally Invasive Access to the Lumbar Spine for Disc Nucleus Replacement Using a Novel Neurophysiological Monitoring System." *The 9$^{th}$ IMAST*, May 2002, 1 page.
Pimenta et al., "The Lateral Endoscopic Transpsoas Retroperitoneal Approach (Letra) fbr Implants in the Lumbar Spine," *World Spine II—Second Interdisciplinary Congress on Spine Care*, Aug. 2003, 2 pages.
Crock, H.V. MD., "Anterior Lumbar Interbody Fusion," Clinical Orthopaedics and Related Research, No. One Hundred Sixty Five, 1982, pp. 157-163, 13 pages.
Mayer and Brock, "Percutaneous endoscopic discectomy: surgical technique and preliminary results compared to microsurgical discectomy," *J. Neurosurg*, 1993, 78: 216-225.
Schaffer and Kambin, "Percutaneous Posterolateral Lumbar Discectomy and Decompression with a 6.9-Millimeter Cannula," *The Journal of Bone and Joint Surgery*, 1991, 73A(6): 822-831.
Friedman, "Percutaneous discectomy: An alternative to chemonucleolysis," *Neurosurgery*, 1983, 13(5): 542-547.
Request for Inter PartesReexamination in re U.S. Pat. No. 7,905,840, dated Feb. 8, 2012, 204 pages.
Brau, "Chapter 22: Anterior Retroperitoneal Muscle-Sparing approach to L2-S1 of the Lumbar Spine," *Surgical Approaches to the Spine.* Robert G. Watkins, MD. (ed) 2003. pp. 165-181.
Kossrnann et al., "Minimally Invasive Vertebral Replacement with Cages in Thoracic and Lumbar Spine," *European Journal of Trauma*, 2001, 27: 292-300.
Mayer H. M. (ed.) *Minimally Invasive Spine Surgery: A Surgical Manual.* 2000. 51 pages.
Pimenta et al., "Implante de protese de nucleo pulposo: analise inicial," *Journal Brasileiro de Neurocirurgia*, 2001, 12(2): 93-96.
Traynelis, "Spinal Arthroplasty," *Neurological Focus*, 2002, 13(2): 12 pages.
Zdeblick, Thomas A. (ed.). Anterior Approaches to the Spine. 1999. 43 pages.
Amended Complaint for *NuVasive, Inc. v. Globus Medical, Inc.*, Case No. 1:10-cv-0849 (D. Del., Oct. 5, 2010), 28 pages.
Request for Inter PartesReexamination in re U.S. Pat. No. 7,819,801, dated Feb. 8, 2012, 89 pages.
Kossman et al., "The use of a refractor system (SynFrame) for open, minimal invasive reconstruction of the anterior column of the thoracic and lumbar spine," *Eur Spine J*, 2001, 10: 396-402.
De Peretti et al., "New possibilities in L2-L5 lumbar arthrodesis using a lateral retroperitoneal approach assisted by laparoscopy: preliminary results," *Eur Spine J*, 1996, 5: 210-216.
Litwin et al., "Hand-assisted laparoscopic surgery (HALS) with the handport system," *Annals of Surgery*, 2000, 231(5): 715-723.
Acland's Video Atlas of Human Anatomy, Section 3.1.7: Paravertebral Muscles. Available online: http://aclandanatomy.com/abstract/4010463. Accessed Jul. 11, 2012.
MedlinePlus, a Service of the U.S. National Library of Medicine and National Institutes of Health. Available online: http://www.nlm.nih.gov/medlineplus/. Accessed Jul. 11, 2012.

(56) References Cited

OTHER PUBLICATIONS

Baulot et al., Adjuvant Anterior Spinal Fusion via Thoracoscopy, *Lyon Chirurgical*, 1994, 90(5): 347-351 including English Translation and Certificate of Translation.
Leu et al., "Percutaneous Fusion of the Lumbar Spine," *Spine*, 1992, 6(3): 593-604.
Rosenthal et al., "Removal of a Protruded Thoracic Disc Using Microsurgical Endoscopy," *Spine*, 1994, 19(9): 1087-1091.
Counterclaim Defendants' Corrected Amended Invalidity Contentions re U.S. Pat. Nos. 8,000,782; 8,005,535; 8,016,767; 8,192,356; 8,187,334; 8,361,156, D. 652,922; D. 666,294 re Case No. 3:12-cv-02738-CAB(MDD), dated Aug. 19, 2013, 30 pages.
Petition for Inter Partes Review IPR2014-00034, filed Oct. 8, 2013, 65 pages.
Petition for Inter Partes Review IPR2014-00035, filed Oct. 8, 2013, 65 pages.
Declaration of Lee Grant, from IPR2014-00034, Oct. 7, 2013, 36 pages.
Declaration of David Hacker from IPR2014-00034, Oct. 4, 2013, 64 pages.
NuVasive, Inc's Opening Claim Construction Brief Regarding U.S. Pat. Nos. 8,000,782; 8,005,535; 8,016,767; 8,192,356; 8,187,334; 8,361,156; D. 652,922; and 5,676,146 C2, filed Sep. 3, 2013, in *Warsaw Orthopedic, Inc.* v. *NuVasive, Inc.*, No. 3:12-cv-02738-CAB-MDD (S.D. Cal.)., 34 pages.
Petition for Inter Partes Review IPR2014-00073, filed Oct. 18, 2013, 65 pages.
Petition for Inter Partes Review IPR2014-00074, filed Oct. 18, 2013, 65 pages.
Petition for Inter Partes Review IPR2014-00075, filed Oct. 21, 2013, 66 pages.
Petition for Inter Partes Review IPR2014-00076, filed Oct. 21, 2013, 65 pages.
Petition for Inter Partes Review IPR2014-00081, filed Oct. 22, 2013, 64 pages.
Petition for Inter Partes Review IPR2014-00087, filed Oct. 22, 2013, 64 pages.
Declaration of Lee Grant, from IPR2014-00073, Oct. 9, 2013, 36 pages.
Declaration of David Hacker, from IPR2014-00073, Oct. 10, 2013, 64 pages.
U.S. Appl. No. 60/392,214, filed Jun. 26, 2002, 97 pages.
Amendment in reply to Feb. 15, 2012 Office Action in U.S. Appl. No. 12/635,418, dated Mar. 16, 2012, 24 pages.
Decision on Appeal in Inter Partes Reexamination Control No. 95/001,247, dated Mar. 18, 2013, 49 pages.
Declaration of Lee Grant, from IPR2014-00074, Oct. 9, 2013, 36 pages.
Declaration of David Hacker, from IPR2014-00074, Oct. 10, 2013, 64 pages.
Declaration of David Hacker, from IPR2014-00075, Oct. 10, 2013, 64 pages.
Amendment in reply to Action of Feb. 7, 2011 and Notice of May 12, 2011, in U.S. Appl. No. 11/789,284, dated May 17, 2011, 16 pages.
Notice of Allowance in U.S. Appl. No. 11/789,284, dated Jul. 18, 2011, 8 pages.
Office action from U.S. Appl. No. 11/789,284, dated Feb. 7, 2011, 10 pages.
Merriam-Webster's Collegiate Dictionary, p. 65 (10th ed. 1998).
Declaration of Lee Grant, from IPR2014-00076, Oct. 9, 2013, 36 pages.
Moed et al., "Evaluation of Intraoperative Nerve-Monitoring During Insertion of an Iliosacral Implant in an Animal Model, *Journal of Bone and Joint Surgery*," 1999, 81-A(11): 9.
Declaration of Lee Grant, from IPR2014-0081, Oct. 9, 2013, 36 pages.
Declaration of David Hacker from IPR2014-00081, Oct. 10, 2013, 64 pages.
U.S. Appl. No. 60/325,424, filed Sep. 25, 2001, 346 pages.
Declaration of Lee Grant, from IPR2014-0087, Oct. 9, 2013, 36 pages.
Declaration of David Hacker from IPR2014-00087, Oct. 10, 2013, 64 pages.
Request for Inter Partes Reexamination in re: U.S. Pat. No. 7,691,057, dated Feb. 8, 2012, 50 pages.
Declaration of Daniel Schwartz, Ph.D. from IPR2014-00034, Oct. 7, 2013, 1056 pages.
Declaration of Daniel Schwartz, Ph.D. from IPR2014-00035, Oct. 7, 2013, 661 pages.
510(K) No. K002677, approved by the FDA on Nov. 13, 2000, 634 pages.
510(K) No. K013215, approved by the FDA on Oct. 16, 2001, 376 pages.
Declaration of Robert G. Watkins, from IPR2014-00073, Oct. 18, 2013, 1101 pages.
Declaration of Daniel Schwartz, from IPR2014-00073, Oct. 12, 2013, 1226 pages.
Declaration of Robert G. Watkins, from IPR2014-00074, Oct. 18, 2013, 548 pages.
Declaration of Daniel Schwartz, from IPR2014-00074, Oct. 12, 2013, 565 pages.
Declaration of Robert G. Watkins, from IPR2014-00075, Oct. 18, 2013, 674 pages.
Declaration of Daniel Schwartz, from IPR2014-00075, Oct. 12, 2013, 1107 pages.
Declaration of Robert G. Watkins, from IPR2014-00076, Oct. 18, 2013, 543 pages.
Declaration of Daniel Schwartz, from IPR2014-00076, Oct. 12, 2013, 1247 pages.
Declaration of David Hacker, from IPR2014-00076, Oct. 10, 2013, 64 pages.
Declaration of Daniel Schwartz, from IPR2014-0081, Oct. 21, 2013, 585 pages.
Declaration of Daniel Schwartz from IPR2014-0087, Oct. 21, 2013, 585 pages.
International Search Report from PCT/US2005/036454, dated Jul. 26, 2007, 2 pages; International Preliminary Report on Patentability from PCT/US2005/036454, dated Aug. 21, 2007, 8 pages.
Wolfhard Caspar, Technique of Microsurgery, in Microsurgery of the Lumbar Spine, Ch. 12 (Dec. 1989 Williams et al. ed.), pp. 105-122.
Catalogue of Surgical Instruments and Appliances (Philip Harris & Co.) 1904, 7 pages.
Riordan, T. "A business man invents a device to give laparoscopic surgeons a better view of their work," *The New York Times*, Mar. 29, 2004, 1 page.
Illustrated Catalogue of Surgical Instruments, Medical Appliances, Diagnostic Apparatus, Etc., by Hynson, Westcott & Co., 1895, 9 pages.
Surgical & Dental Instruments, by Noyes Bros. & Cutler, St. Paul, MN US, 1895, 6 pages.
Massey, Conservative Gynecology and Electro-Therapeutics (Philadelphia, F.A. Davis Company, 1909), 545 pages.
Winckel F., Diseases of Women: a Handbook for Physicians and Students (Philadelphia, P. Biakiston, Son & Co., 1887), 713 pages.
Ashton, W. A Text-Book on the Practice of Gynecology for Practitioners and Students, (Philadelphia, W. B. Saunders Company, 1916), 1120 pages.
Illustrated Catalogue of Surgical and Scientific Instruments and Appliances, The Surgical Manufacturing Co., London, 1920, 3 pages.
Reid, "On the Vaginal Speculum." in: *The American Journal of Obstetrics and Diseases of Women and Children*, vol. 16 (New York, W.A. Townsend & Adams, 1883), pp. 276-281.
Reid, "New Bivalve Speculum." in: *The Transactions of the Edinburgh Obsterical Society* (Edinburgh, Oliver & Boyd, 1883), pp. 57-59.
Thorburn, A Practical Treatise on the Diseases of Women (Philadelphia, Miller, 1887), pp. 16-17.
Ricci, The Vaginal Speculum and Its Modifications Throughout the Ages (New York Medical College, City Hospital Division, 1949), 29 pages.

(56) References Cited

OTHER PUBLICATIONS

Clinical Gynecology, Medical and Surgical, for Students and Practitioners (Philadelphia, Keating & Coe ed,, 1894), 1067 pages.
Miltex Surgical Instruments, *Miltex Instrument Company, Inc.*, 1996, 656 pages.
Standard Surgical Instruments, *Medical Department, U.S. Army*, 1920, 23 pages.
Davenport, Diseases of Women: A Manual of Gynecology Designed Especially for the Use of Students and General Practitioners, (Philadelphia, Lea Brothers & Co., 1898), 437 pages.
Montgomery, E. "Endometritis: Uterine Dilatation and Drainage." in: *The Medical News: A Weekly Medical Journal*, vol. 60 (Jan.-Jun. 1892), pp. 404-407.
The Surgical Armamentarium (V. Mueller 1973), 2 pages.
Goodell's Speculum I, Dittrick Museum of Medical History, No later than Jun. 25, 2001, 6 pages.
Goodell's Speculum II, Dittrick Museum of Medical History, No later than Jun. 25, 2001, 8 pages.
De Vilbiss Speculum II, Dittrick Museum of Medical History, No later than Jun. 25, 2001, 2 pages.
De Vilbiss Speculum III, Dittrick Museum of Medical History, No later than Jun. 25, 2001, 7 pages.
De Vilbiss Speculum I, Dittrick Museum of Medical History, No later than Jun. 25, 2001, 8 pages.
Illustrated Catalogue of Surgical and Scientific Instruments and Appliances (The Surgical Manufacturing Co.) 1920, 3 pages.
McCulloch and Young, "Instrumentation for Spinal Microsurgery, Including Ancillary Equipment." in: *Essentials of Spinal Microsurgery*, (Philadelphia, Lippincott-Raven,1998), 24 pages.
Caspar W., "The Microsurgical Technique for Herniated Lumbar Disk Operations." in: *Aesculap Scientific Information*, Edition 4, No later than Jun. 25, 2001, 4 pages.
Papavero and Caspar, "The Lumbar Microdiscectorny," *Acts Orthop Scand (Suppl. 251)*, 1993, 64:34-37.

SURGICAL ACCESS SYSTEM AND RELATED METHODS

CROSS-REFERENCES TO RELATED APPLICATIONS

The present application is a continuation of U.S. patent application Ser. No. 16/400,978, filed May 1, 2019, which is a continuation of U.S. patent application Ser. No. 15/484, 871, filed Apr. 11, 2017, which is a continuation of U.S. patent application Ser. No. 11/665,039, filed Apr. 9, 2007, which is a U.S. national phase under 35 U.S.C. 371 of international application PCT/US2005/036454, filed Oct. 11, 2005. International patent application PCT/US2005/036454 claims the benefit of priority from U.S. provisional patent application 60/617,498, filed Oct. 8, 2004, and U.S. provisional patent application 60/720,710, filed Sep. 26, 2005. The entire contents of these priority applications are hereby expressly incorporated by reference into this disclosure as if set forth fully herein.

BACKGROUND OF THE INVENTION

I. Field of the Invention

The present invention relates generally to systems and methods for performing surgical procedures and, more particularly, for accessing a surgical target site in order to perform surgical procedures.

II. Discussion of the Prior Art

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. The access systems developed to date, however, fail in various respects to meet all the needs of the surgeon population.

One drawback associated with prior art surgical access systems relates to the ease with which the operative corridor can be created, as well as maintained over time, depending upon the particular surgical target site. For example, when accessing surgical target sites located beneath or behind musculature or other relatively strong tissue (such as, by way of example only, the psoas muscle adjacent to the spine), it has been found that advancing an operative corridor-establishing instrument directly through such tissues can be challenging and/or lead to unwanted or undesirable effects (such as stressing or tearing the tissues). While certain efforts have been undertaken to reduce the trauma to tissue while creating an operative corridor, such as (by way of example only) the sequential dilation system of U.S. Pat. No. 5,792,044 to Foley et al., these attempts are nonetheless limited in their applicability based on the relatively narrow operative corridor. More specifically, based on the generally cylindrical nature of the so-called "working cannula," the degree to which instruments can be manipulated and/or angled within the cannula can be generally limited or restrictive, particularly if the surgical target site is a relatively deep within the patient.

This highlights yet another drawback with the prior art surgical access systems, namely, the challenges in establishing an operative corridor through or near tissue having major neural structures which, if contacted or impinged, may result in neural impairment for the patient. Due to the threat of contacting such neural structures, efforts thus far have largely restricted to establishing operative corridors through tissue having little or substantially reduced neural structures, which effectively limits the number of ways a given surgical target site can be accessed. This can be seen, by way of example only, in the spinal arts, where the exiting nerve roots and neural plexus structures in the psoas muscle have rendered a lateral or far lateral access path (so-called trans-psoas approach) to the lumbar spine virtually impossible. Instead, spine surgeons are largely restricted to accessing the spine from the posterior (to perform, among other procedures, posterior lumbar interbody fusion (PLIF)) or from the anterior (to perform, among other procedures, anterior lumbar interbody fusion (ALIF)).

Posterior-access procedures involve traversing a shorter distance within the patient to establish the operative corridor, albeit at the price of oftentimes having to reduce or cut away part of the posterior bony structures (e.g. lamina, facets, spinous process) in order to reach the target site (which typically comprises the disc space). Anterior-access procedures are relatively simple for surgeons in that they do not involve reducing or cutting away bony structures to reach the surgical target site. However, they are nonetheless disadvantageous in that they require traversing through a much greater distance within the patient to establish tire operative corridor, oftentimes requiring an additional surgeon to assist with moving the various internal organs out of the way to create the operative corridor.

The present invention is directed at eliminating, or at least minimizing the effects of, the above-identified drawbacks in the prior art.

SUMMARY OF THE INVENTION

The present invention accomplishes this goal by providing a novel access system and related methods which involve detecting the existence of (and optionally the distance and/or direction to) neural structures before, during, and after the establishment of air operative corridor through (or near) any of a variety of tissues having such neural structures which, if contacted or impinged, may otherwise result in neural impairment for the patient. It is expressly noted that, although described herein largely in terms of use in spinal surgery, the access system of the present invention is suitable for use in any number of additional surgical procedures wherein tissue having significant neural structures must be passed through (or near) in order to establish an operative corridor. It is also expressly noted that, although shown and described herein largely within the context of lateral surgery in the lumbar spine, the access system of the present invention may be employed in any number of other spine surgery access approaches, including but not limited to posterior, postero-lateral, anterior, and antero-lateral access, and may be employed in the lumbar, thoracic and/or cervical spine, all without departing from the present invention.

According to one broad aspect of the present invention, the access system comprises a tissue distraction assembly and a tissue retraction assembly, both of which may be equipped with one or more electrodes for use in detecting the existence of (and optionally the distance and/or direction to) neural structures. The tissue distraction assembly (in conjunction with one or more elements of the tissue retraction assembly) is capable of, as an initial step, distracting a region of tissue between the skin of the patient and the surgical target site. The tissue retraction assembly is capable of, as a secondary step, being introduced into this distracted region to thereby define and establish the operative corridor. Once established, any of a variety of surgical instruments, devices, or implants may be passed through and/or manipulated within the operative corridor depending upon the given surgical procedure. The electrode(s) are capable of, during both tissue distraction and retraction, defecting the existence of (and optionally the distance and/or direction to) neural structures such that the operative corridor may be established through (or near) any of a variety of tissues having such neural structures which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly may include any number of components capable of performing the necessary distraction. By way of example only, the tissue distraction assembly may include a K-wire and one or more dilators (e.g., sequentially dilating cannulae) for performing the necessary tissue distraction to receive the remainder of the tissue retractor assembly thereafter. One or more electrodes may be provided on one or more of the K-wire and dilator(s) to detect the presence of (and optionally the distance and/or direction to) neural structures during tissue distraction.

The tissue retraction assembly may include any number of components capable of performing the necessary retraction. By way of example only, the tissue retraction assembly may include one or more retractor blades extending from a handle assembly. The handle assembly may be manipulated to open the retractor assembly; that is, allowing the retractor blades to separate from one another (simultaneously or sequentially) to create an operative corridor to the surgical target site. In a preferred embodiment, this is accomplished by maintaining a posterior retractor blade in a fixed position relative to the surgical target site (so as to avoid having it impinge upon any exiting nerve roots near the posterior elements of the spine) while the additional retractor blades (i.e. cephalad-most and caudal-most blades) are moved or otherwise translated away from the posterior retractor blade (and each other) so as to create the operative corridor in a fashion that doesn't impinge upon the region of the exiting nerve roots. In one optional aspect of the present invention, the cephalad-most and/or caudal-most blades may pivot or rotate outward from a central axis of insertion, such that the operative corridor may be further expanded. In a further optional aspect of the present invention, the retractor may include a locking element to maintain the blades in an initial alignment during insertion, and a variable-stop mechanism to allow the user to control the degree of expansion of the operative corridor. A blade expander tool may be provided to facilitate manual pivoting of the retractor blades.

The retractor blades may be optionally dimensioned to receive and direct a rigid shim element to augment the structural stability of the retractor blades and thereby ensure the operative corridor, once established, will not decrease or become more restricted, such as may result if distal ends of the retractor blades were permitted to "slide" or otherwise move in response to the force exerted by the displaced tissue. In a preferred embodiment, only the posterior refractor blade is equipped with such a rigid shim element. In an optional aspect, this shim element may be advanced into the disc space after the posterior retractor blade is positioned, but before the retractor is opened into the fully retracted position. The rigid shim element is preferably oriented within the disc space such that is distracts the adjacent vertebral bodies, which serves to restore disc height. It also preferably advances a sufficient distance within the disc space (preferably past the midline), which advantageously forms a protective barrier that prevents the migration of tissue (such as nerve roots) into the operative field and the inadvertent advancement of instruments outside the operative field. In an optional embodiment, the caudal-most and/or cephalad-most blades may be fitted with any number of retractor extenders for extending (laterally or length-wise) the blades, which advantageously forms a protective barrier that prevents the migration of tissue (such as muscle and soft tissue) into the operative field and the inadvertent advancement of instruments outside the operative field.

The retractor blades may optionally be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, coupling one or more light sources to the retractor blades such that the terminal ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Figure 1:
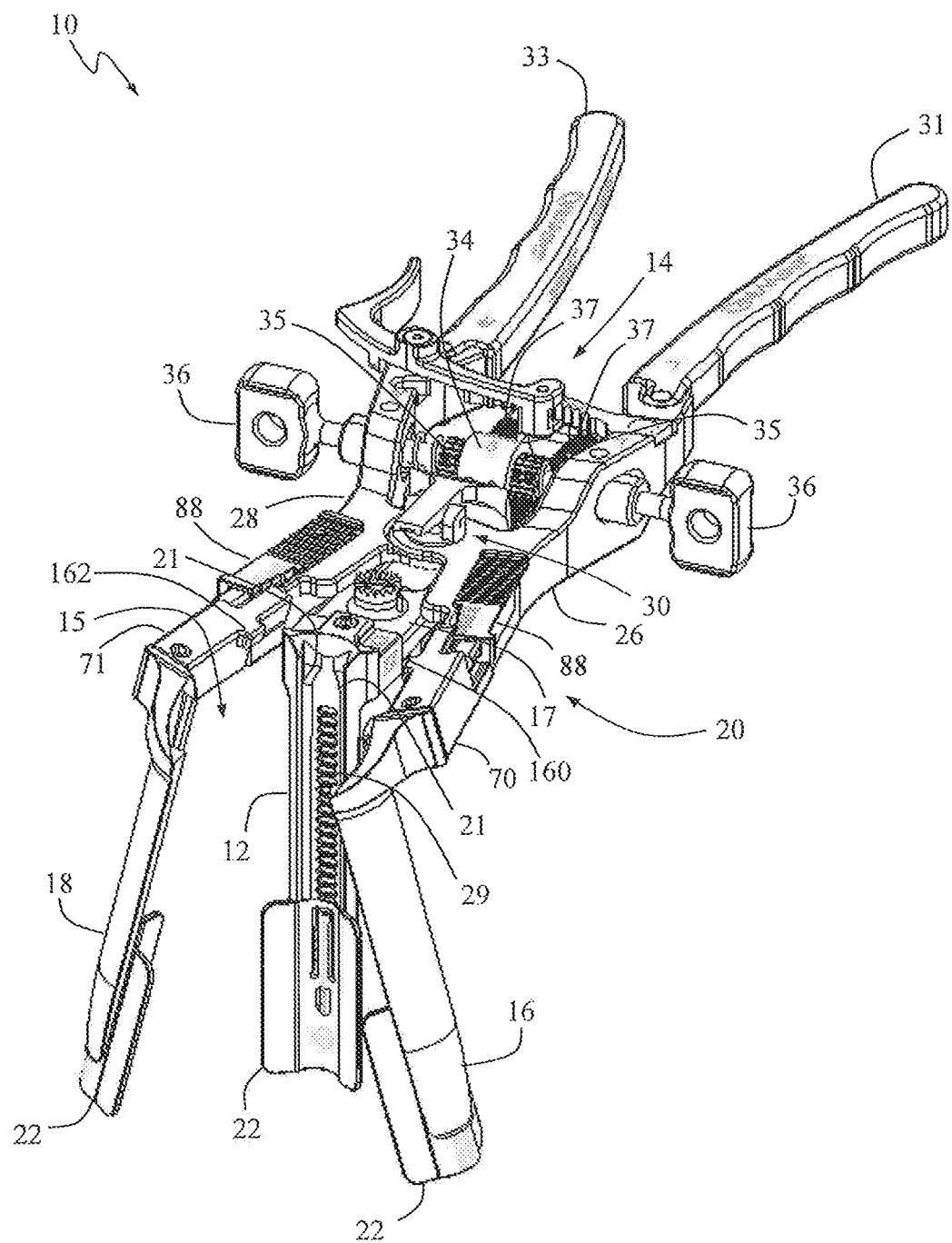
FIG. 1 is a perspective view of a tissue retraction assembly forming part of a surgical access system according to the present invention, shown in a fully retracted or "open" position.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. It is also expressly noted that, although shown and described herein largely within the context of lateral surgery in the lumbar spine, the access system of the present invention may be employed in any number of other spine surgery access approaches, including but not limited to posterior, postero-lateral, anterior, and antero-lateral access, and may be employed in the lumbar, thoracic and/or cervical spine, all without departing from the present invention. The surgical access system disclosed herein boasts a variety of inventive features and components that warrant patent protection, both individually and in combination.

The present invention involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present invention accomplishes this by providing a tissue distraction assembly and a tissue retraction assembly, both of which may be equipped with one or more electrodes for use in detecting the existence of (and optionally the distance and/or direction to) neural structures.

These electrodes are preferably provided for use with a nerve surveillance system such as, by way of example, the type shown and described in the above referenced Neuro-Vision PCT Applications. Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present invention. In so doing, the system as a whole (including the surgical access system of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly of the present invention (comprising a K-wire, an initial dilator, and a plurality of sequentially dilating cannulae) is employed to distract the tissues extending between the skin of the patient and a given surgical target site (preferably along the posterior region of the target intervertebral disc). Once distracted, the resulting void or distracted region within the patient is of sufficient size to accommodate a tissue retraction assembly of the present invention. More specifically, the tissue retraction assembly (comprising a plurality of retractor blades extending from a handle assembly) may be advanced relative to the secondary distraction assembly such that the retractor blades, in a first, closed position, are advanced over the exterior of the secondary distraction assembly. At that point, the handle assembly may be operated to move the retractor blades into a second, open or "retracted" position to create an operative corridor to the surgical target site.

According to one aspect of the invention, following (or before) this retraction, a posterior shim element (which is preferably slidably engaged with the posterior retractor blade) may be advanced such that a distal shim extension in positioned within the posterior region of the disc space. If done before retraction, this helps ensure that the posterior retractor blade will not move posteriorly during the retraction process, even though the other retractor blades (e.g. cephalad-most and caudal-most) are able to move and thereby create an operative corridor. Fixing the posterior retractor blade in this fashion serves several important functions. First, the distal end of the shim element serves to distract the adjacent vertebral bodies, thereby restoring disc height. It also rigidly couples the posterior retractor blade in fixed relation relative to the vertebral bodies. The posterior shim element also helps ensure that surgical instruments employed within the operative corridor are incapable of being advanced outside the operative corridor, preventing inadvertent contact with the exiting nerve roots during the surgery. Once in the appropriate retracted state, the cephalad-most and caudal-most retractor blades may be locked in position and, thereafter, retractor extenders advanced therealong to prevent the ingress or egress of instruments or biological structures (e.g. nerves, vasculature, etc. . . .) into or out of the operative corridor. Optionally, the cephalad-most and/or caudal-most retractor blades may be pivoted in an outward direction to further expand the operative corridor. Once the operative corridor is established, any of a variety of surgical instruments, devices, or implants may be passed through and/or manipulated within the operative corridor depending upon the given surgical procedure.

Figure 2:
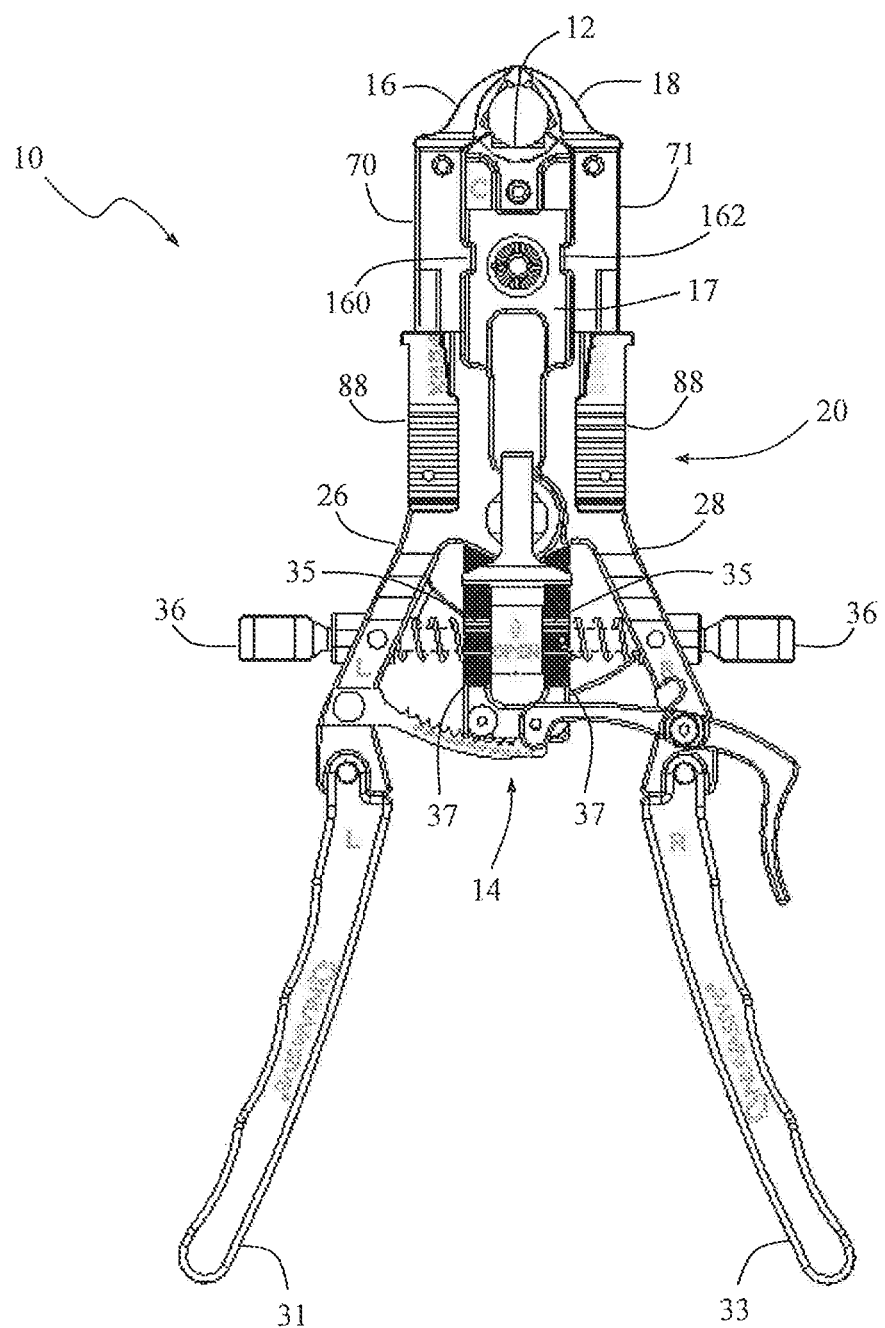
FIGS. 2-3 are top and perspective views, respectively, of the tissue retraction assembly of FIG. 1 shown in a closed position according to the present invention.
Figure 3:
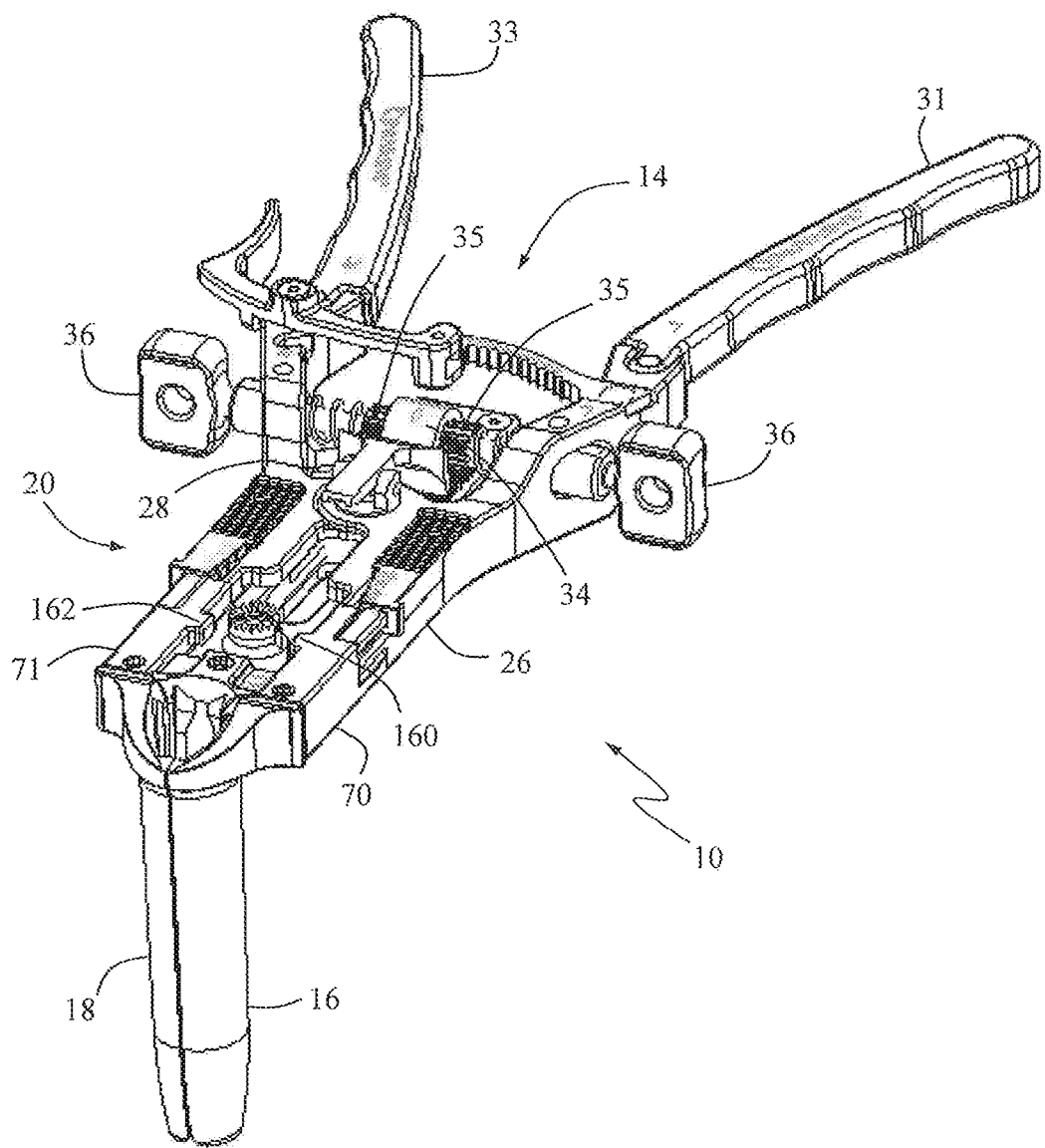
Figure 4:
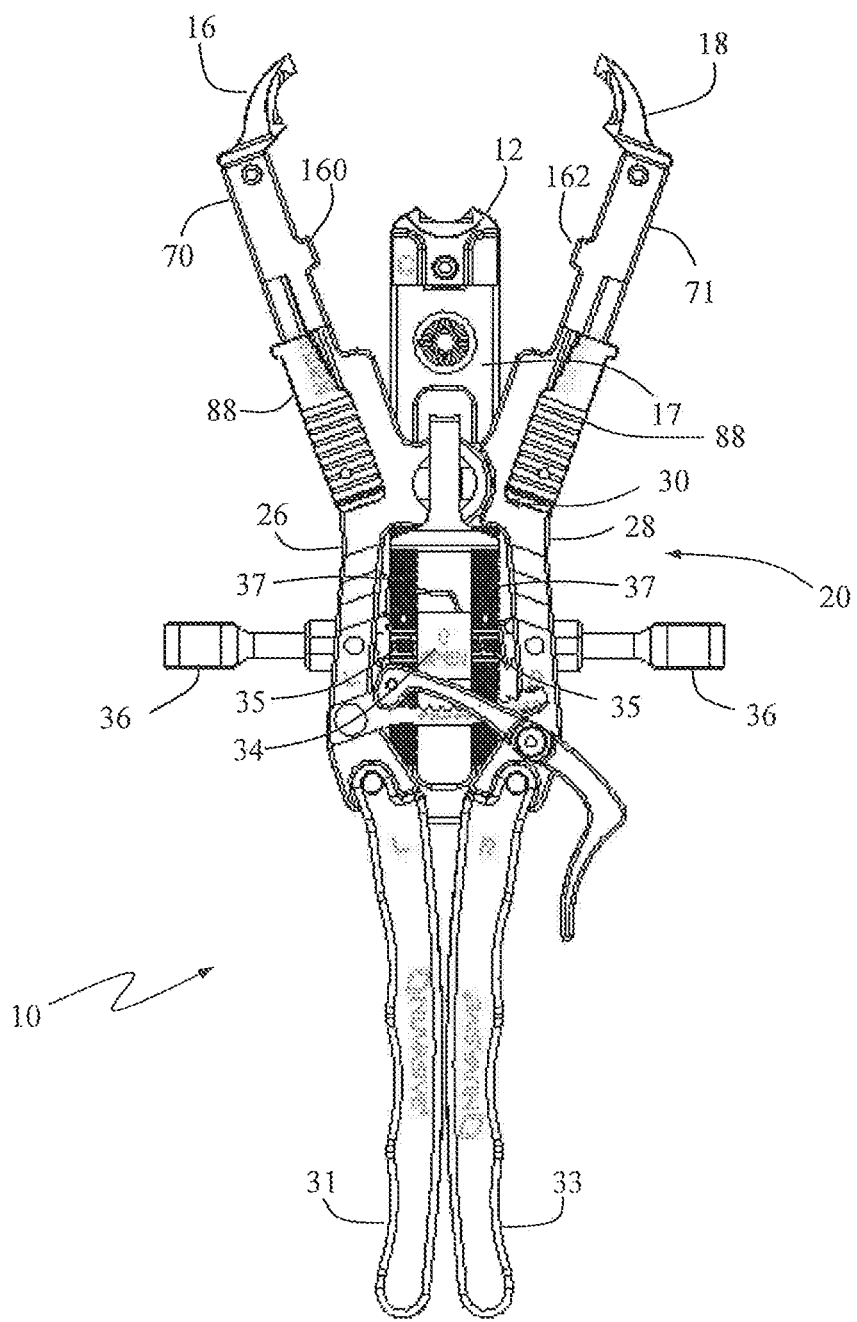
FIGS. 4-5 are top and perspective views, respectively, of the tissue retraction assembly of FIG. 1 in an open position.
Figure 5:
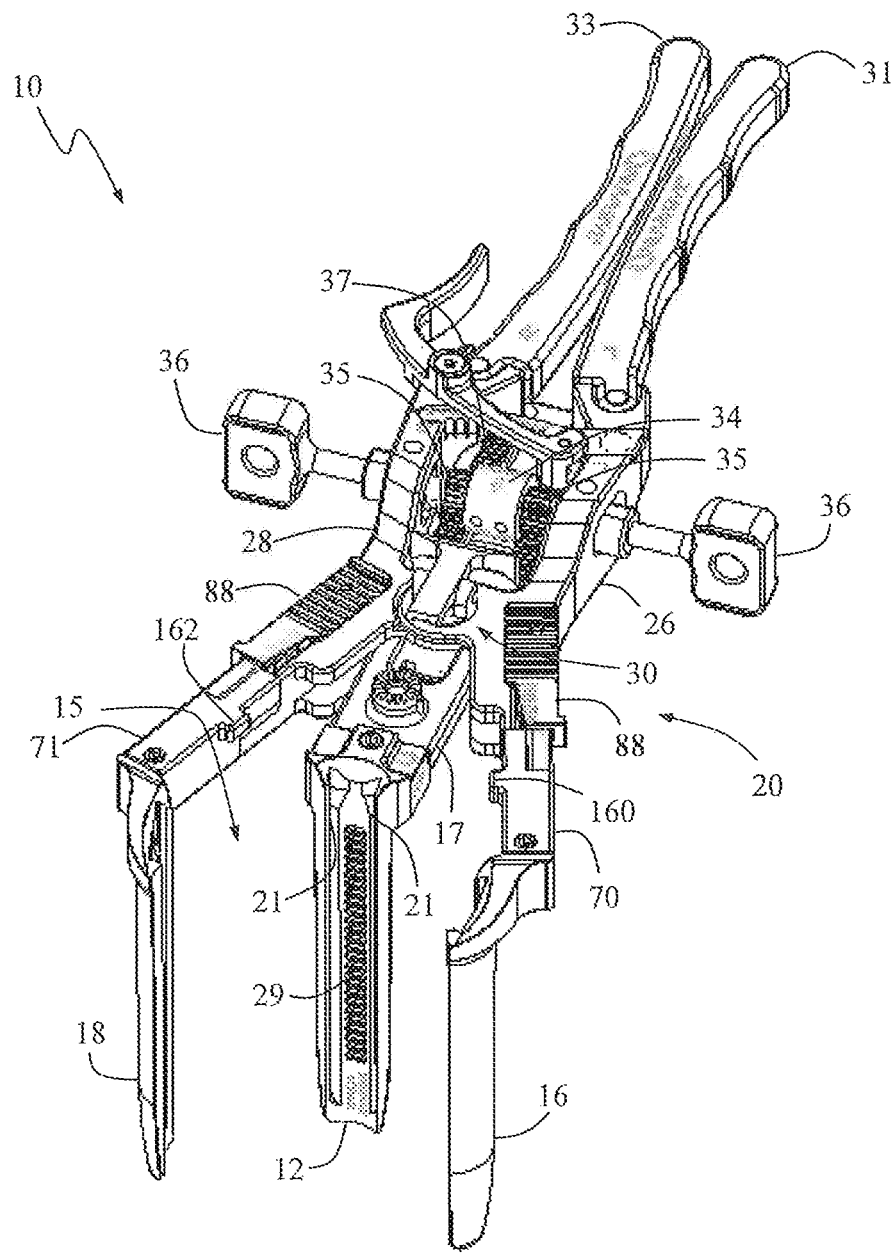

FIGS. 1-S illustrate a tissue retraction assembly 10 forming part of a surgical access system according to the present invention, including a plurality of retractor blades extending from a handle assembly 20. By way of example only, the handle assembly 20 is provided with a first retractor blade 12, a second retractor blade 16, and a third retractor blade 18. FIG. 1 illustrates the retractor assembly 10 in a fully retracted or "open" configuration, with the retractor blades 12, 16, 18 positioned a distance from one another so as to form an operative corridor 15 therebetween which extends to a surgical target site (e.g. an annulus of an intervertebral disc). In an important aspect of the present invention, the blades 16, 18 are capable of being pivoted or rotated relative to the handle 10, as best appreciated with combined reference to FIGS. 1 and 4-5. FIGS. 2-3 show the retractor assembly 10 in an initial "closed" configuration, with the retractor blades 12, 16, 18 in a generally abutting relation to one another. Although shown and described below with regard to the three-bladed configuration, it is to be readily appreciated that the number of retractor blades may be increased or decreased without departing from the scope of the present invention. Moreover, although described and shown herein with reference to a generally lateral approach to a spinal surgical target site (with the first blade 12 being the "posterior" blade, the second blade 36 being the "cephalad-most" blade, and the third blade 18 being the "caudal-most" blade), it will be appreciated that the retractor assembly 10 of the present invention may find use in any number of different surgical approaches, including generally posterior, generally postero-lateral, generally anterior and generally antero-lateral.

The retractor blades 12, 16, 18 may be composed of any material suitable for introduction into the human body, including but not limited to aluminum, titanium, and/or clear polycarbonate, that would ensure rigidity during tissue distraction. The retractor blades 12, 16, 18 may be optionally coated with a carbon fiber reinforced coating to increase strength and durability. The blades 12, 16, 18 may be optionally constructed from partially or wholly radiolucent materials (e.g. aluminum, PEEK, carbon-fiber, and titanium) to improve the visibility of the surgeon during imaging (e.g. radiographic, MRI, CT, fluoroscope, etc. . . . ). The retractor blades 12, 14, 18 may also be composed of a material that would destruct when autoclaved (such as polymer containing a portion of glass particles), which may be advantageous in preventing the unauthorized re-use of the blades 12, 16, 18 (which would be provided to the user in a sterile state). The retractor blades 12, 16, 18 may be provided in any number of suitable lengths, depending upon the anatomical environment and surgical approach, such as (by way of example only) the range from 20 mm to 150 mm. Based on this range of sizes, the tissue retraction assembly 10 of the present invention is extremely versatile and may be employed in any of a variety of desired surgical approaches, including but not limited to lateral, posterior, postero-lateral, anterior, and antero-lateral, by simply selecting the desired size retractor blades 12, 16, 18 and attaching them to the handle assembly 20 as will be described herein.

Figure 6:
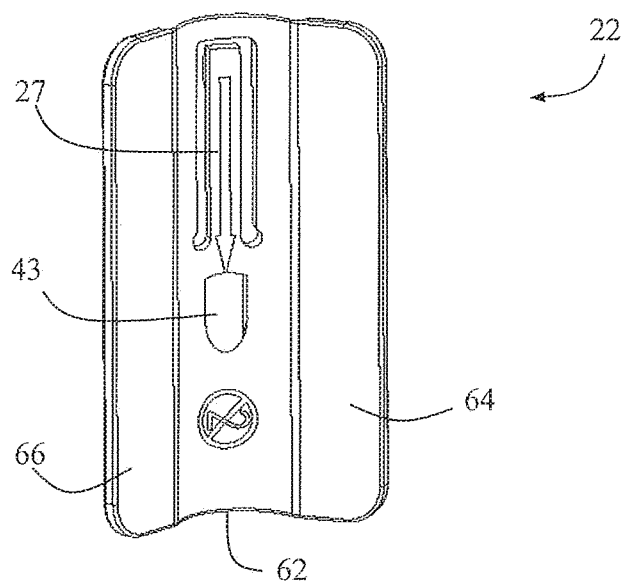
FIGS. 6-7 are perspective views illustrating the front and back of a wide retractor extender for use with any one of the retractor blades according to the retractor of the present invention.
Figure 7:
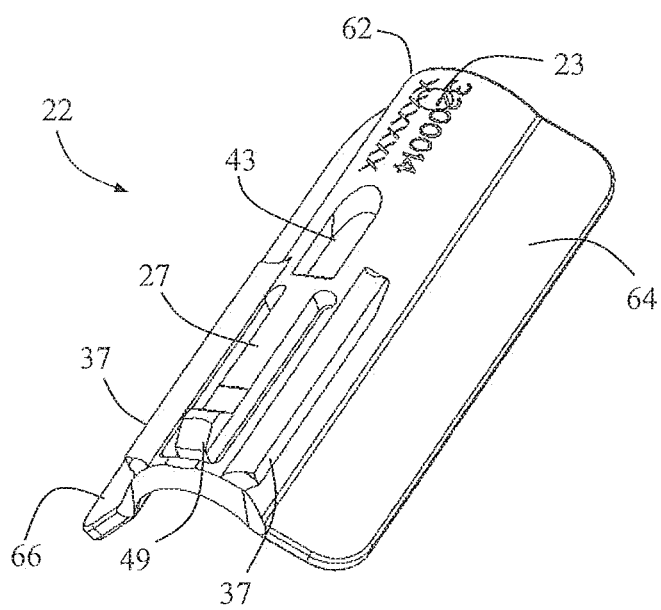
Figure 8:
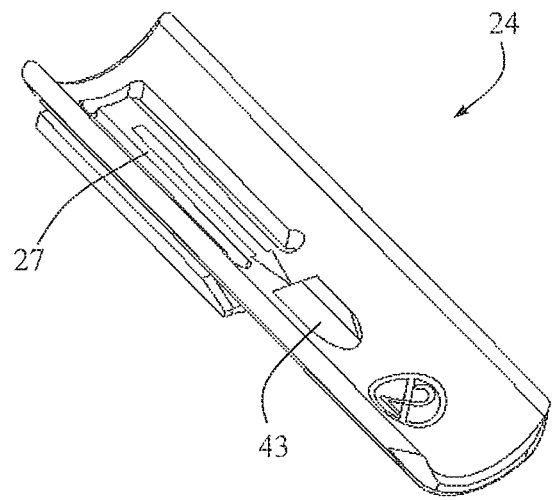
FIGS. 8-9 are perspective views illustrating the front and back of a narrow retractor extender for use with one of the retractor blades according to the retractor of the present invention.
Figure 9:
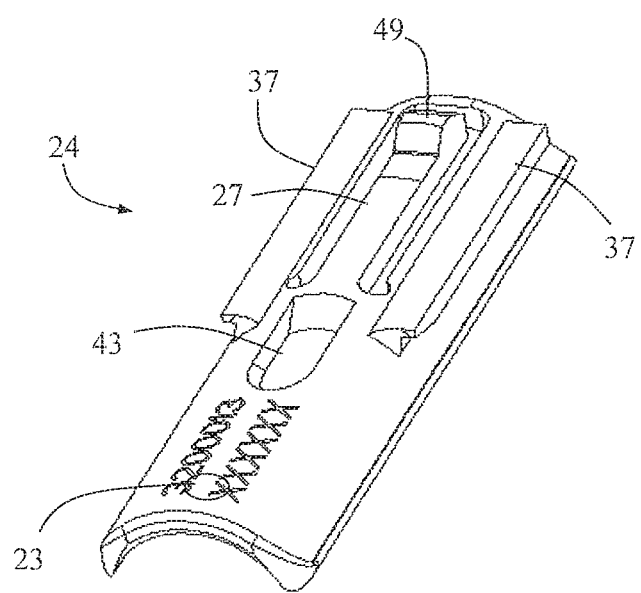
Figure 10:
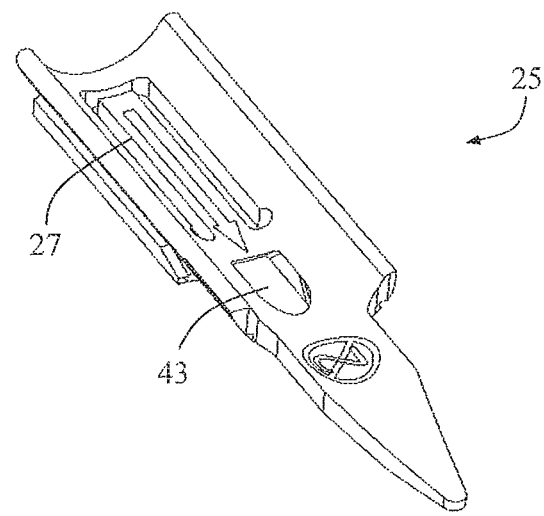
FIGS. 10-11 are perspective views illustrating the front and back of a shim element for use with a posterior retractor blade of the retractor according to the retractor of the present invention.
Figure 11:
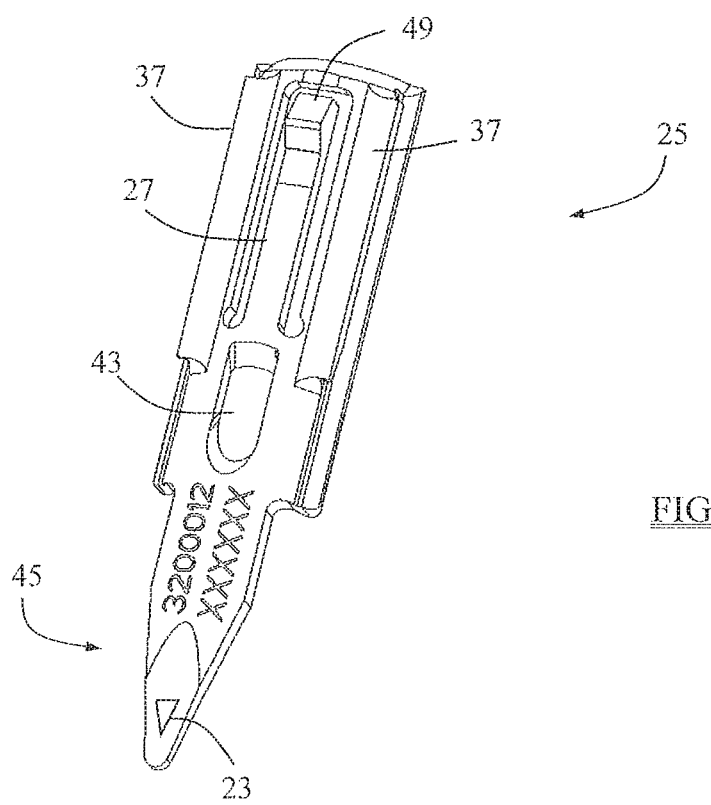
Figure 12:
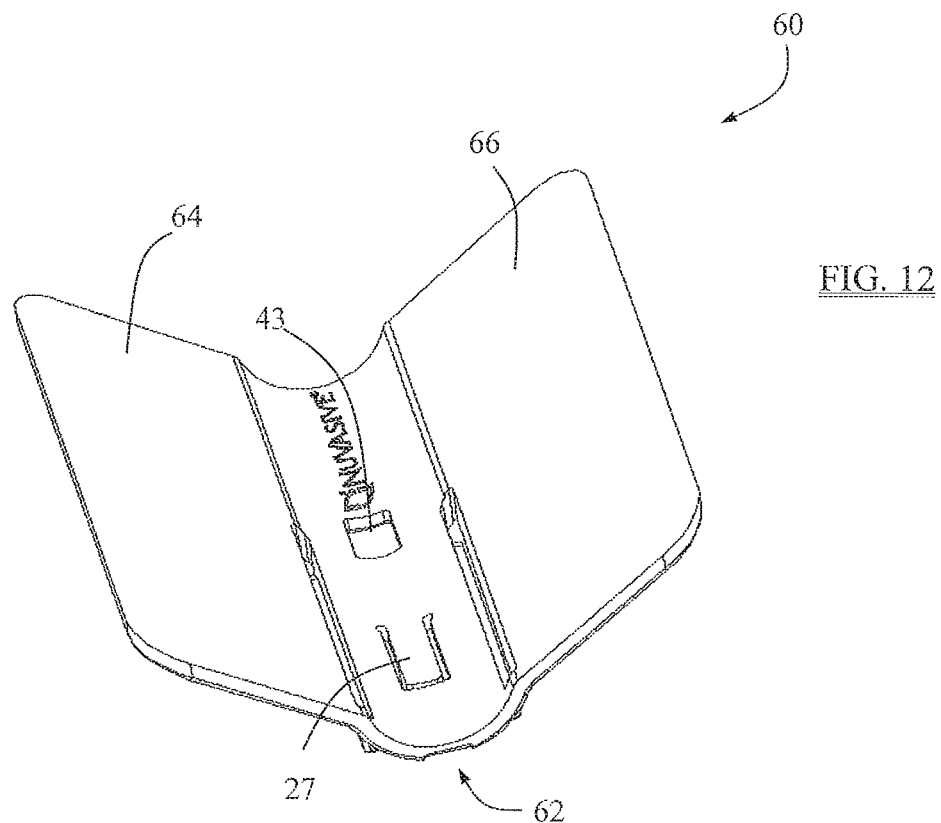
FIGS. 12-13 are perspective views of the front and back, respectively, of a shim element according to one embodiment of the present invention.
Figure 13:
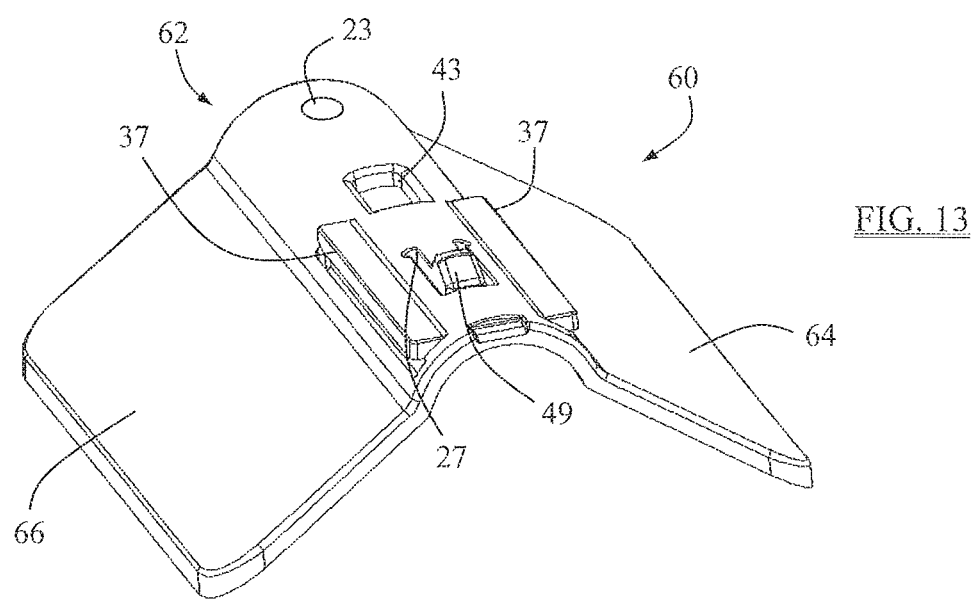
Figure 14:
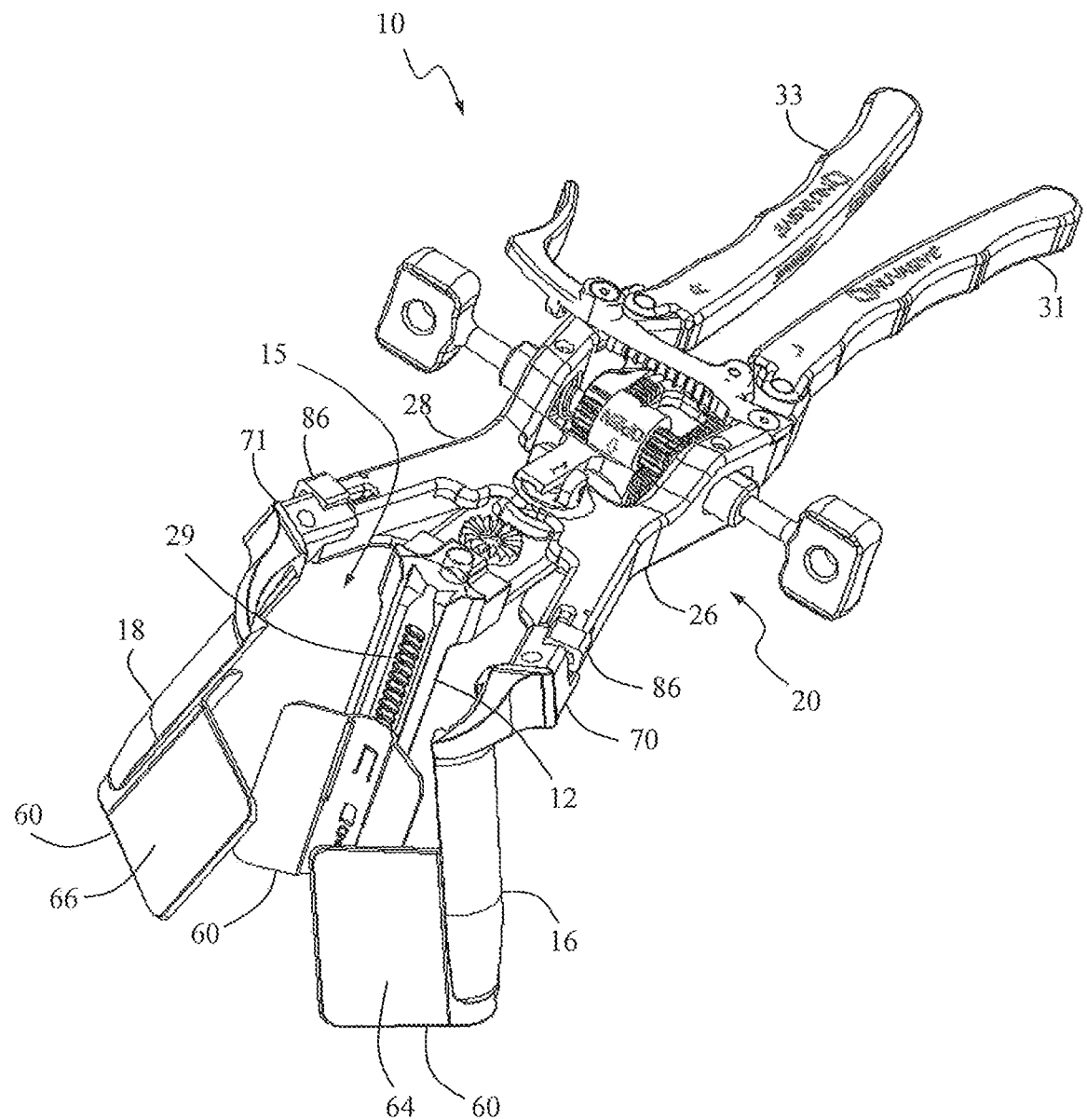
FIGS. 14-15 are perspective and top views, respectively, of a tissue refraction assembly of according to one embodiment of the present invention, shown in an open position with a shim and/or retractor extender installed on each retractor blade.
Figure 15:
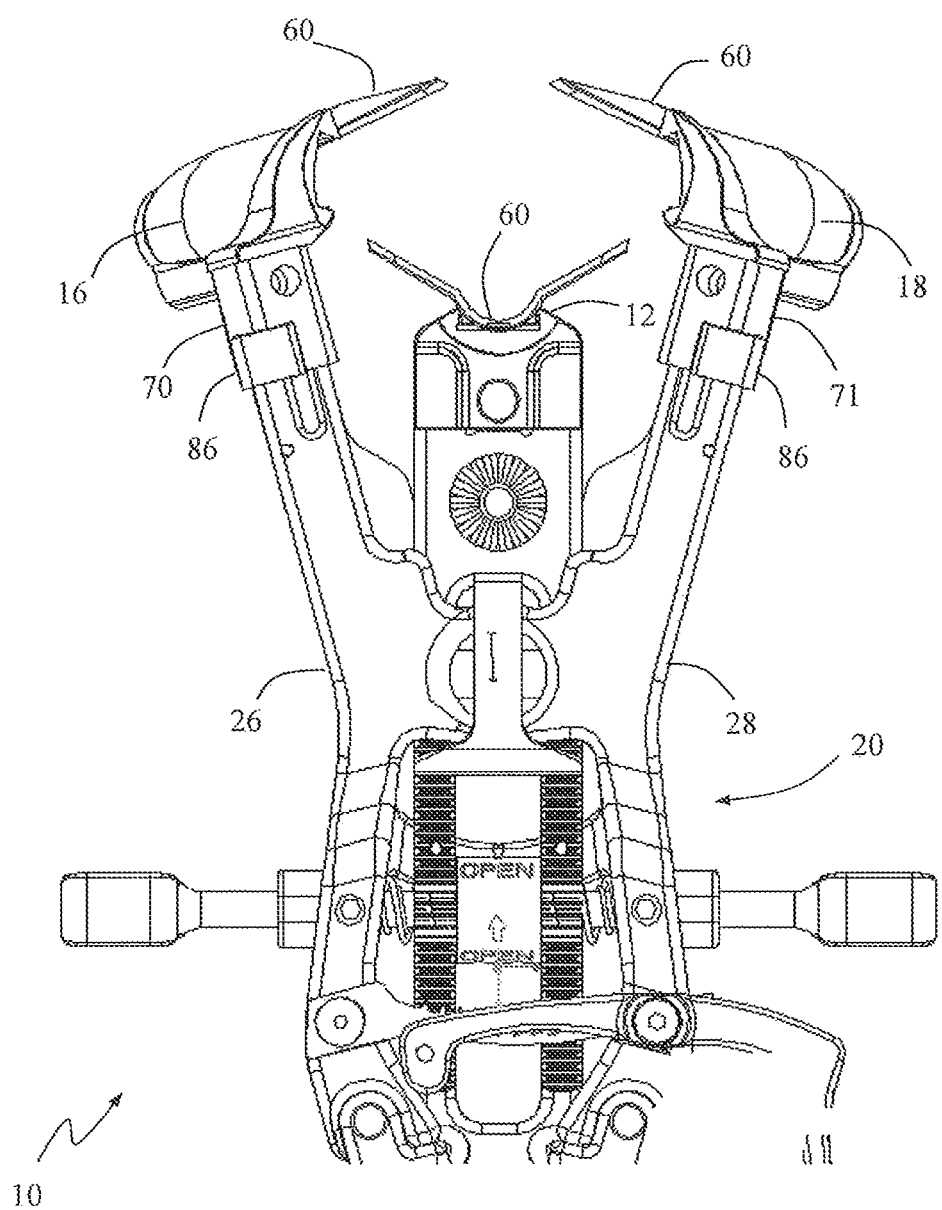

The retractor blades 12, 16, 18 may be equipped with various additional features or components. By way of example only, one or more of the retractor blades 12, 16, 18 may be equipped with a retractor extender, such as a wide retractor extender 22 as shown in FIGS. 6-7, a narrow retractor extender 24 as shown in FIGS. 8-9 and/or an extra wide retractor extender 60 as shown in FIGS. 12-13. The retractor extenders 22, 24, 60 extend from the retractor blades 12, 16, 18 (as shown in FIGS. 14-15, by way of example, with reference to retractor extender 60) to form a protective barrier to prevent the ingress or egress of instruments or biological structures (e.g. nerves, vasculature, etc. . . . ) into or out of the operative corridor 15. Depending upon the anatomical setting and surgical approach, one or more of the retractor blades 12, 16, 18 may be equipped with a shim element 25 as shown in FIGS. 10-11. Shim element 25 has a distal tapered region 45 which may be advanced into tissue (e.g. bone, soft tissue, etc. . . . ) for the purpose of anchoring the blades 12, 16, 18 and/or advanced into the disc space to distract the adjacent vertebral bodies (thereby restoring disc height). In similar fashion to the retractor extenders 22, 24, 60, the shim element 25 also forms a protective barrier to prevent the ingress or egress of instruments or biological structures (e.g. nerves, vasculature, etc. . . . ) into or out of the operative corridor 15.

Retractor extenders 22, 24, 60 and/or shim element 25 may be made out any material suitable for use in the human body, including but not limited to biologically compatible plastic and/or metal, preferably partially or wholly radiolucent in nature material (such as aluminum, PEEK, carbon-fibers and titanium). Construction from plastic or thin metal provides the additional benefit of allowing the shim 25 and/or retractor extenders 22, 24, 60 to be collapsed into a compressed or low profile configuration at the skin level as the element is inserted, and then expanded once it is below skin level and within the operative corridor 15. Retractor extenders 22, 24, 60 may have symmetric narrow configurations (FIGS. 8-9) and/or broad configurations (FIGS. 6-7 and 12-13) and/or an asymmetric configuration of narrow and broad elements (FIGS. 14-15). For example, any or all of the retractor extenders 22, 24, 60 may be provided with a lateral section 64 of the type shown in FIGS. 6-7, a narrow configuration (without lateral sections 64, 66) of the type shown in FIGS. 8-9, and/or a lateral section 66 of the type shown in FIGS. 12-13, all without departing from the scope of the present invention. The retractor extenders 22, 24, 60 and/or the shim element 25 may be composed of a material that would destruct when autoclaved (such as polymer containing a portion of glass particles), which may be advantageous in preventing the unauthorized re-use of the retractor extenders 22, 24, 60 and/or the shim element 25 (which would be provided to the user in a sterile state). Slits may also be provided on the shim 25 to improve flexibility. The retractor extenders 22, 24, 60 and/or the shim element 25 may have a parabolic concave curvature in addition to the configuration shown by way of example only in FIGS. 12-13.

Each of the retractor extenders 22, 24, 60 and/or the shim element 25 may be equipped with a mechanism to selectively and releasably engage with the respective retractor blades 12, 16, 18. By way of example only, this may be accomplished by configuring the retractor extenders 22, 24, 60 and/or the shim element 25 with a tab element 27 capable of engaging with corresponding ratchet-like grooves (shown at 29 in FIG. 1) along the inner-facing surfaces of the retractor blades 12, 16, 18. Each of the retractor extenders 22, 24, 60 and/or the shim element 25 is provided with a pair of engagement elements 37 having, by way of example only, a generally dove-tailed cross-sectional shape. The engagement elements 37 are dimensioned to engage with receiving portions 21 on the respective retractor blades 12, 16, 18. In a preferred embodiment, each of the retractor extenders 22, 24, 60 and/or the shim element 25 may be provided with an elongate slot 43 for engagement with an insertion tool 140 of the type shown in FIGS. 34-37 (as will be described in greater detail below). Each tab member 27 is also equipped with an enlarged tooth element 49 which engages within corresponding grooves 29 provided along the inner surface of the retractor blades 12, 16, 18. On the wide and extra wide retractor extenders 22, 60, respectively, each includes a center portion 62 flanked by a pair of lateral sections 64, 66, which effectively increase the width of the retractor blades 12, 16, 18.

According to the present invention, any or all of the retractor blades 12, 16, 18, the retractor extenders 22, 24, 60, and/or the shim element 25 may be provided with one or more electrodes 23 (preferably at or near their distal regions) equipped for use with a nerve surveillance system, such as, by way of example, the type shown and described in the NeuroVision PCT Applications. Such a nerve surveillance system is capable of detecting the existence of (and optionally the distance and/or direction to) neural structures during the retraction of tissue by detecting the presence of nerves by applying a stimulation signal to electrodes 23 and monitoring the evoked EMG signals from the myotomes associated with the nerves in the vicinity of the retraction system 10 of the present invention. In so doing, the system as a whole (including the surgical retraction system 10 of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

With reference to FIGS. 1-5, the handle assembly 20 may be coupled to any number of mechanisms for rigidly registering the handle assembly 20 in fixed relation to the operative site, such as through the use of an articulating arm mounted to the operating table (not shown). The handle assembly 20 includes first and second arm members 26, 28 hingedly coupled via coupling mechanism shown generally at 30. The second retractor blade 16 is rigidly coupled (generally perpendicularly) to the end of the first arm member 26. The third retractor blade 18 is rigidly coupled (generally perpendicularly) to the end of the second arm member 28. The first retractor blade 12 is rigidly coupled (generally perpendicularly to) a translating member 17, which is coupled to the handle assembly 20 via a linkage assembly shown generally at 14. The linkage assembly 14 includes a roller member 34 having a pair of manual knob members 36 which, when rotated via manual actuation by a user, causes teeth 35 on the roller member 34 to engage within ratchet-like grooves 37 in the translating member 17. Thus, manual operation of the knobs 36 causes the translating member 17 to move relative to the first and second arm members 26, 28.

Through the use of handle extenders 31, 33, the arms 26, 28 may be simultaneously opened such that the second and third retractor blades 16, 18 move away from one another. In this fashion, the dimension and/or shape of the operative corridor 15 may be tailored depending upon the degree to which the translating member 17 is manipulated relative to the arms 26, 28. That is, the operative corridor 15 may be tailored to provide any number of suitable cross-sectional shapes, including but not limited to a generally circular cross-section, a generally ellipsoidal cross-section, and/or an oval cross-section. Optional light emitting devices (not shown) may be coupled to one or more of the retractor blades 12, 16, 18 to direct light down the operative corridor 15.

Figure 16:
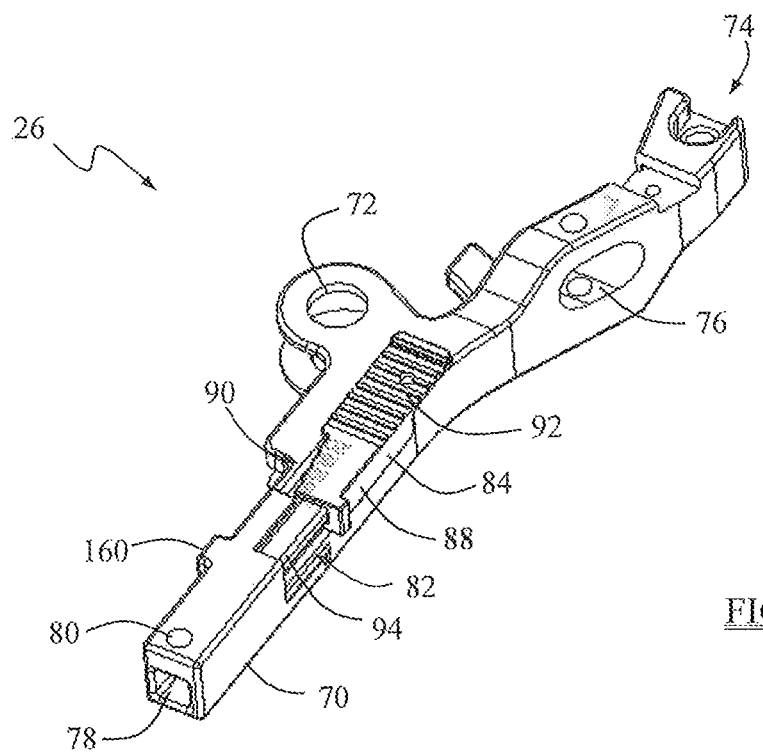
FIGS. 16-17 are perspective views of an arm member comprising part of the tissue retraction assembly of FIG. 1.
Figure 17:
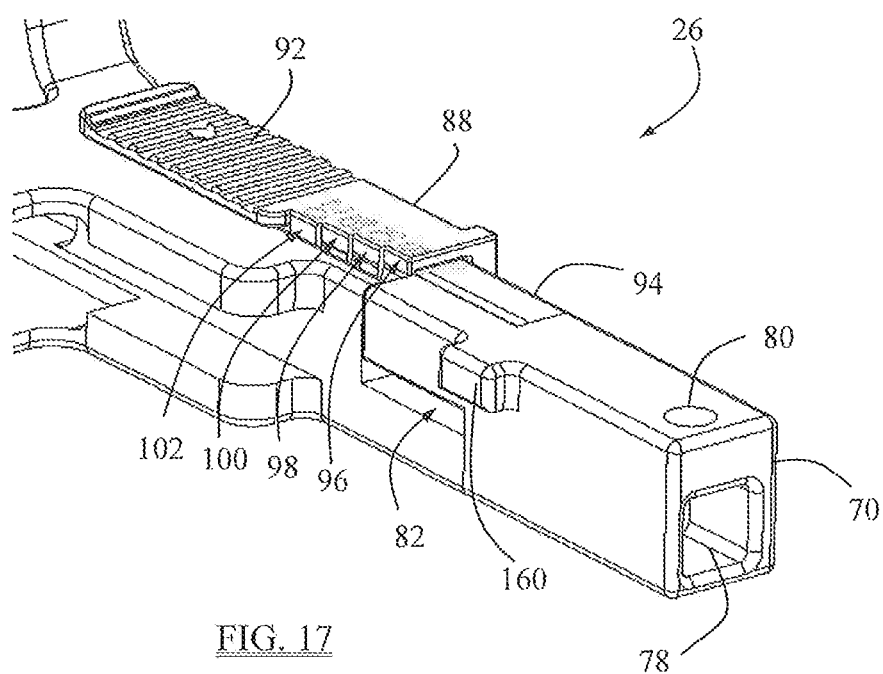
Figure 18:
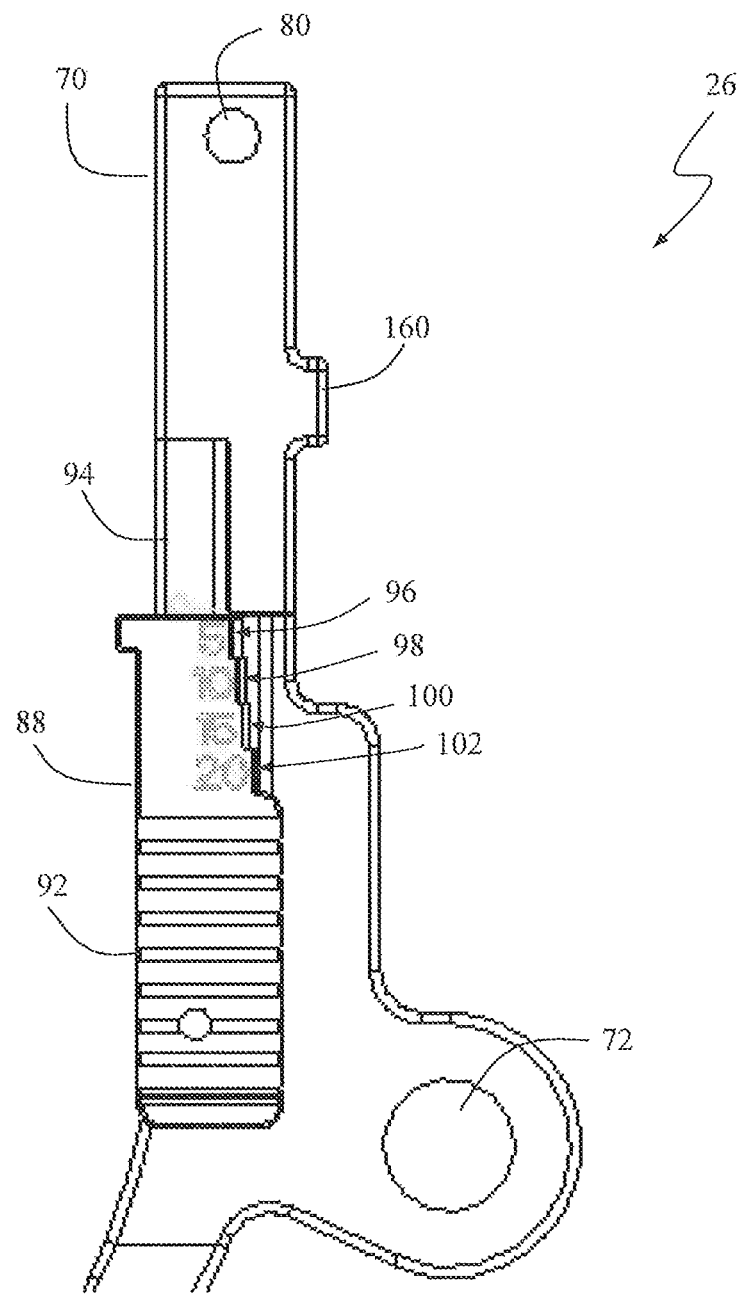
FIG. 18 is a top view of the arm member of FIG. 16.

FIGS. 16-18 illustrate the first arm member 26 in greater detail. First arm member 26 includes a distal pivot member 70, a coupling aperture 72, a proximal region 74 at which handle extender 31 may be attached, an aperture 76 through which knob 36 passes, and a slidable locking mechanism 84 (which may include a single-step lock 86 shown by way of example in FIGS. 14-15 and/or a variable-stop lock 88 as shown in FIGS. 16-18 and described by way of example below). The distal pivot member 70 includes a blade aperture 78, an aperture 80, and a cutout region 82. The blade aperture 78 is dimensioned to interact with the proximal region of the retractor blade 16 in a male female relationship, such that the male end of blade 16 fits into the female blade aperture 78. To rigidly secure blade 16 to retractor arm 26, a pin or screw (not shown) may be inserted into aperture 80.

The variable-stop lock 88 allows the user to control the degree of expansion of the operative corridor 15. Variable-stop lock 88 includes a variable-stop region 90 and a user engagement region 92, and is dimensioned to slidably engage locking bar 94. The variable-stop region 90 may include any number of sequential step-wise cutout regions corresponding to the angulation desired for the retractor blades 16, 18. By way of example only, the variable-stop locking mechanism includes four sequential step-wise cutout regions 96, 98, 100, 102. Each sequential step-wise cutout region 96, 98, 100, 102 may correspond to a distinct degree of angulation of the retractor blades 16, 18 (relative to the "closed" position shown in FIGS. 2-3). By way of example only, sequential step-wise cutout regions 96, 98, 100, 102 may correspond to 5°, 10°, 15° and 20° of angulation, respectively. Each sequential step-wise cutout region 96, 98, 100, 102 is dimensioned to interact with the distal pivot member 70 once the desired degree of angulation is determined. The user engagement region 92 may include a series of ridges 104 or any other suitable friction-causing element to allow a user to manually operate the variable-stop lock 88 (to adjust and/or lock it).

Figure 19:
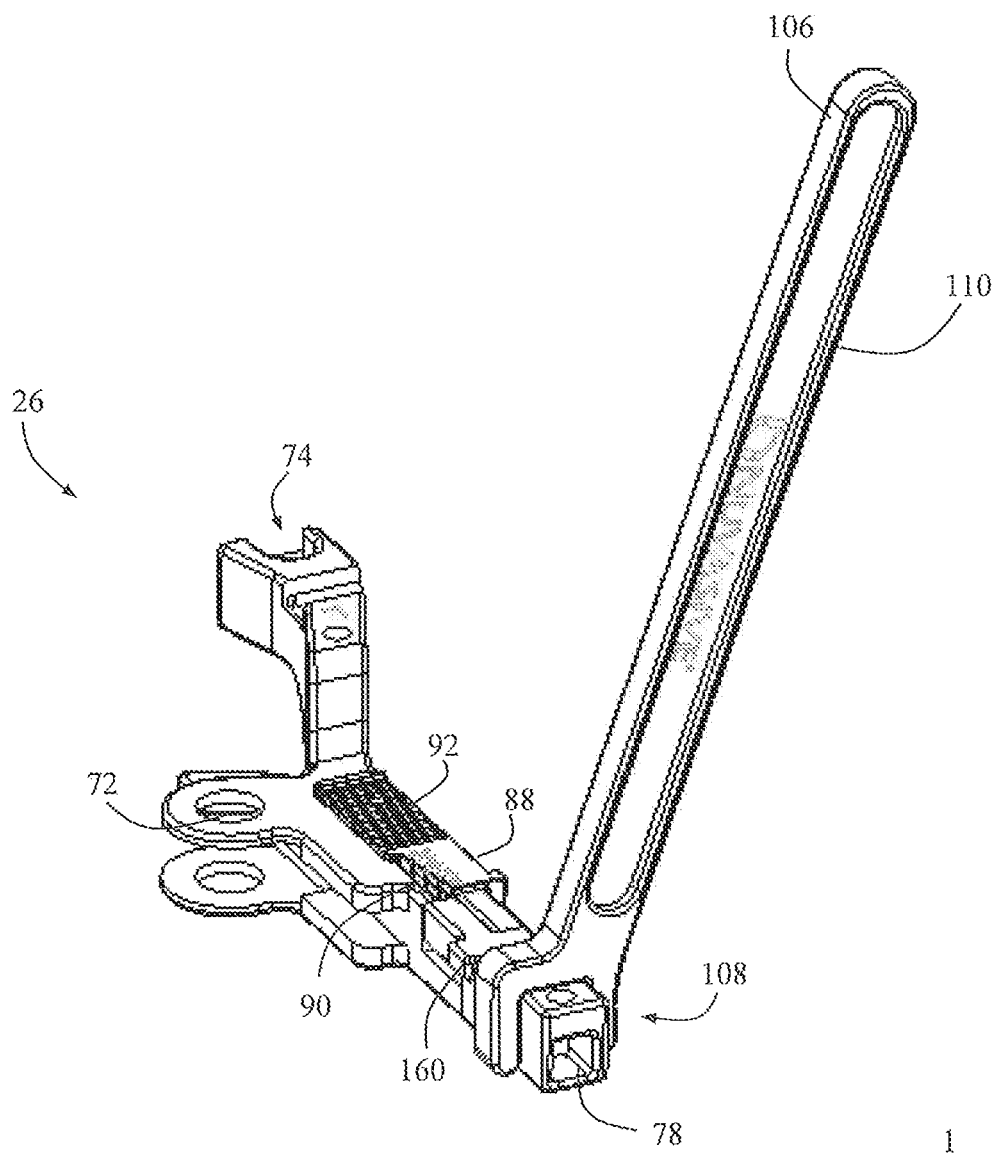
FIGS. 19-20 are perspective and top views, respectively, of the arm member of FIG. 16 in which a pivot wrench is coupled with a distal pivot region of the arm member.
Figure 20:
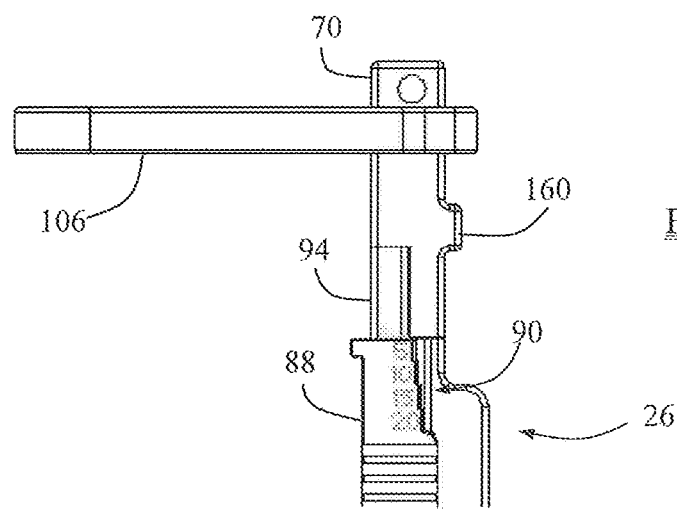
Figure 21:
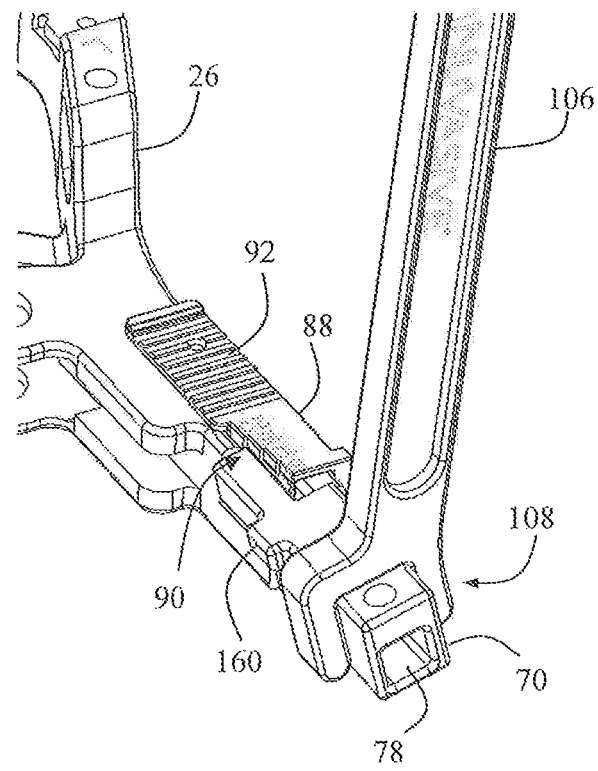
FIG. 21 is a perspective view of the arm member of FIG. 19 after the distal pivot region as been pivoted and the locking mechanism has been engaged.
Figure 22:
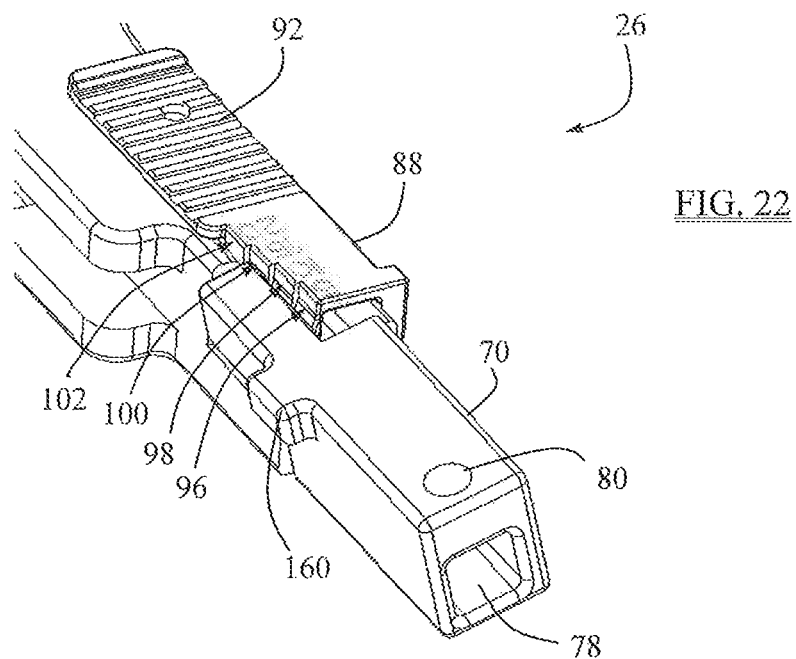
FIGS. 22-23 are perspective and top views, respectively, of the arm member of FIG. 21 in which the pivot wrench has been removed.
Figure 23:
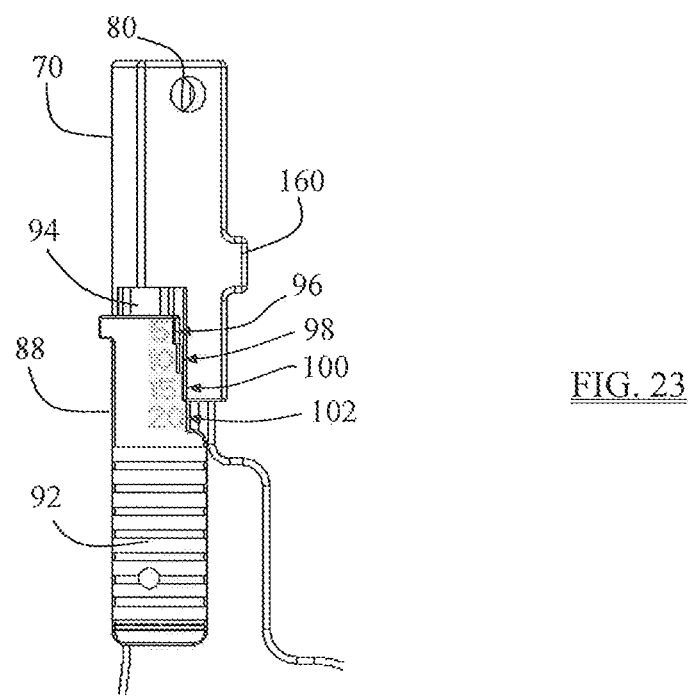
Figure 25:
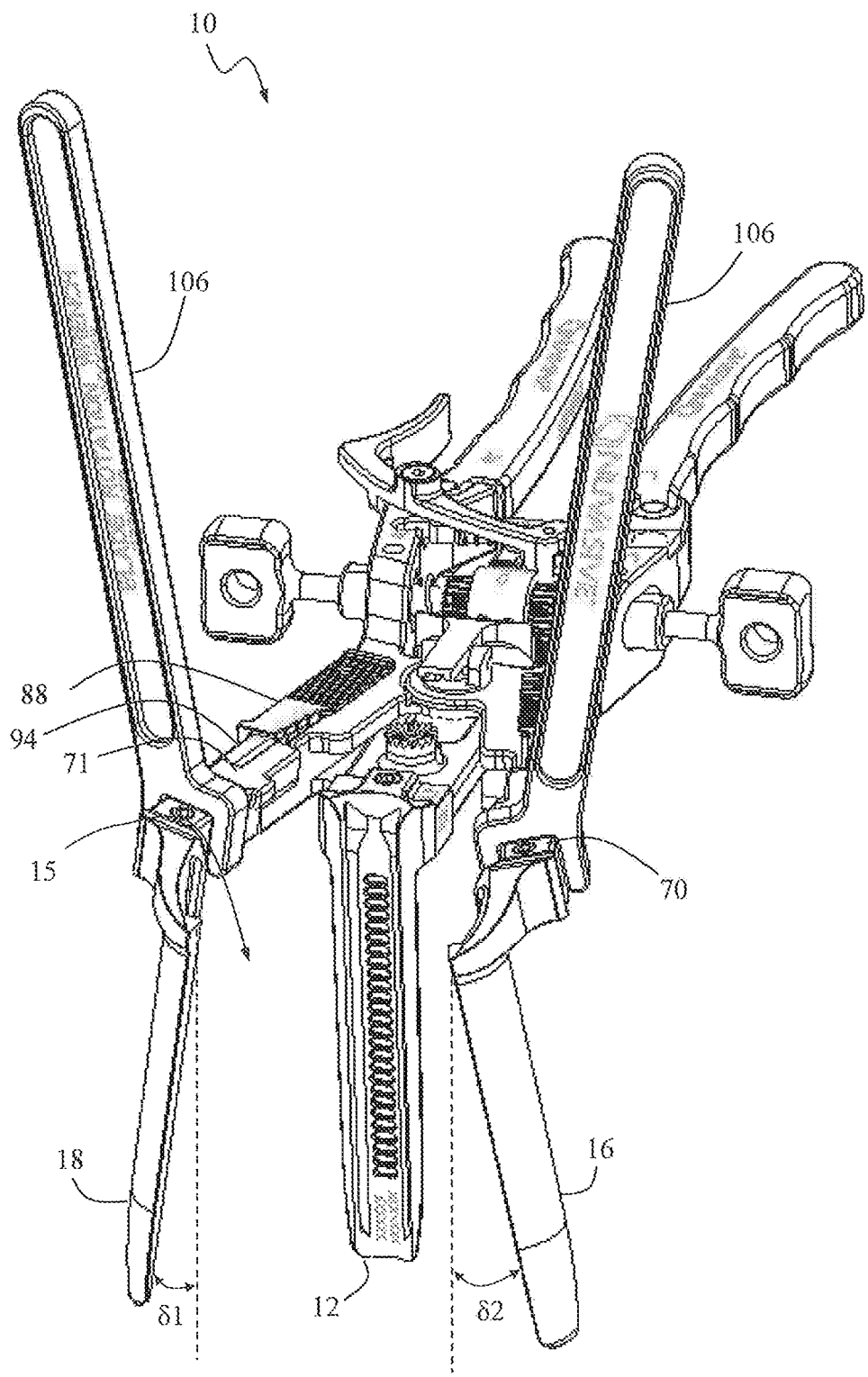
FIG. 25 is a perspective view of the tissue retraction assembly of FIG. 24 after pivoting of the blades.
Figure 26:
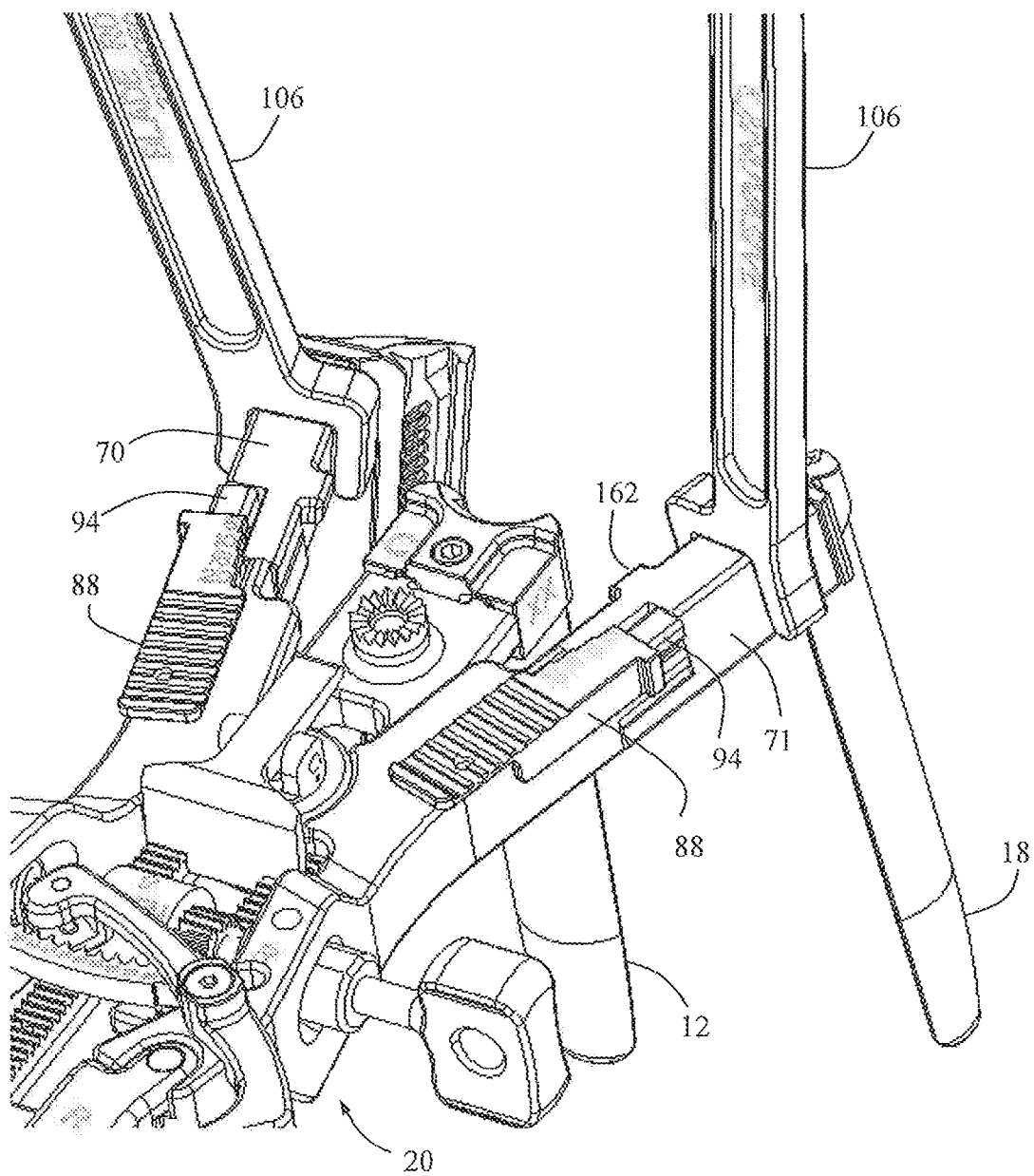
FIG. 26 is a perspective view of the tissue retraction assembly of FIG. 25, in which the locking mechanisms have been activated.
Figure 27:
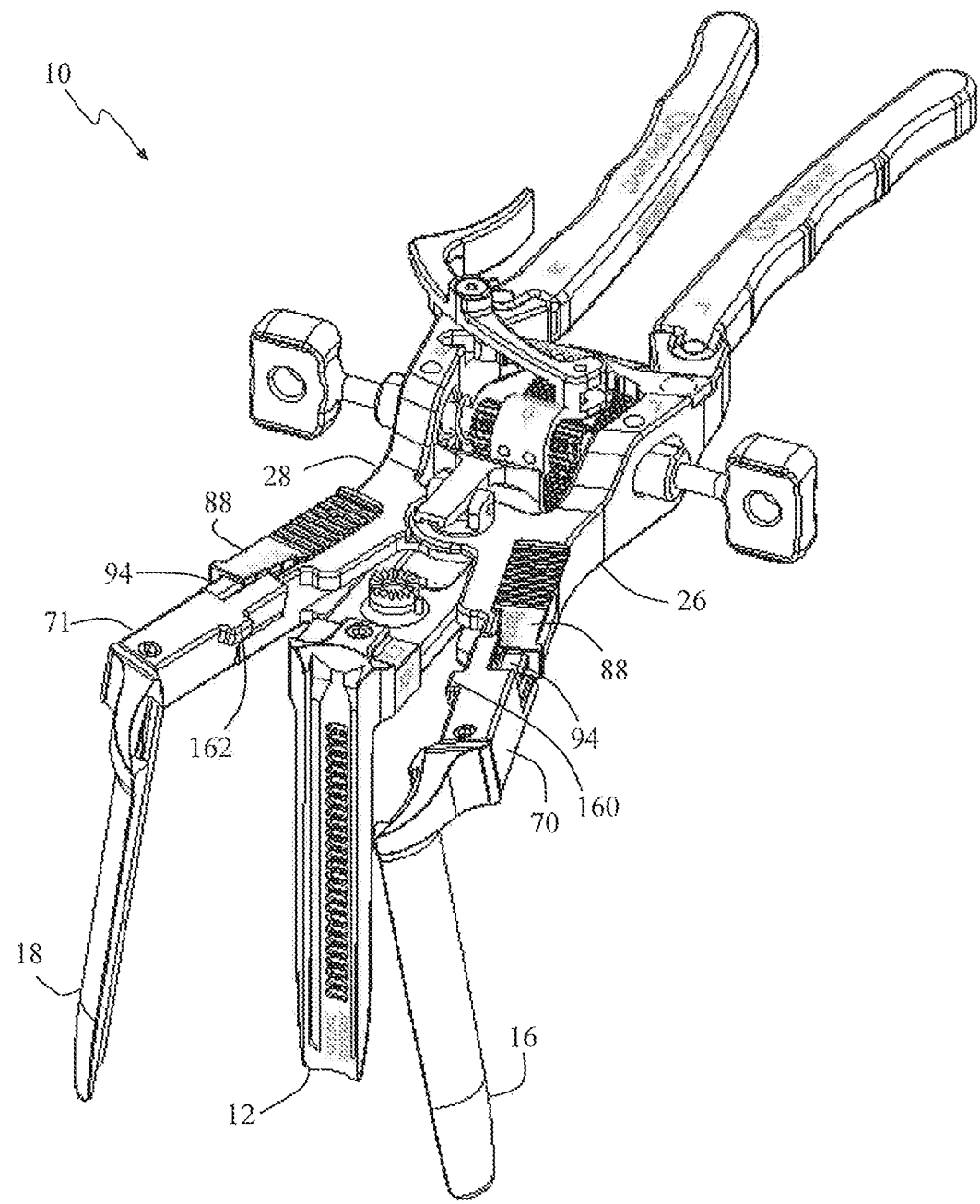
FIGS. 27-28 are perspective and top views, respectively, of the tissue retraction assembly of FIG. 25, in which the cephalad-most and caudal-most blades have been pivoted and the locking mechanisms have been engaged.
Figure 28:
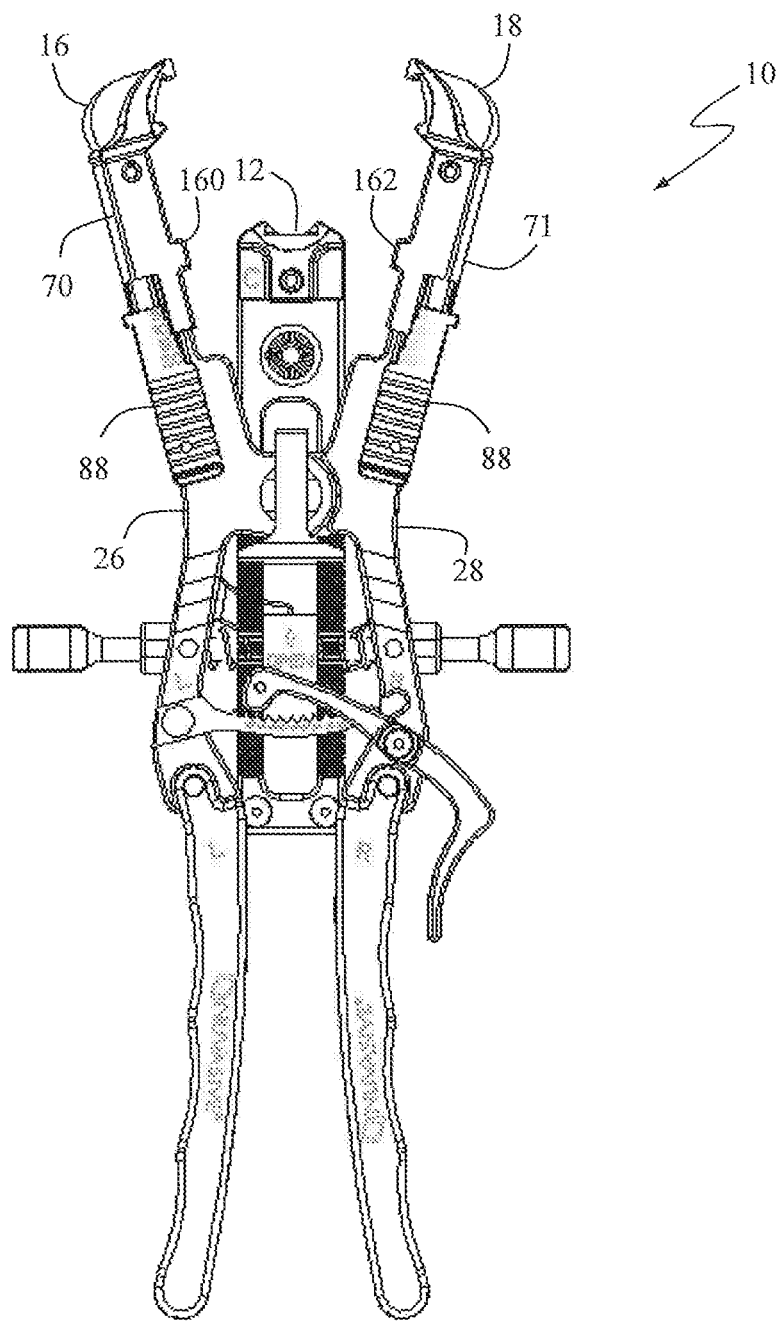
Figure 29:
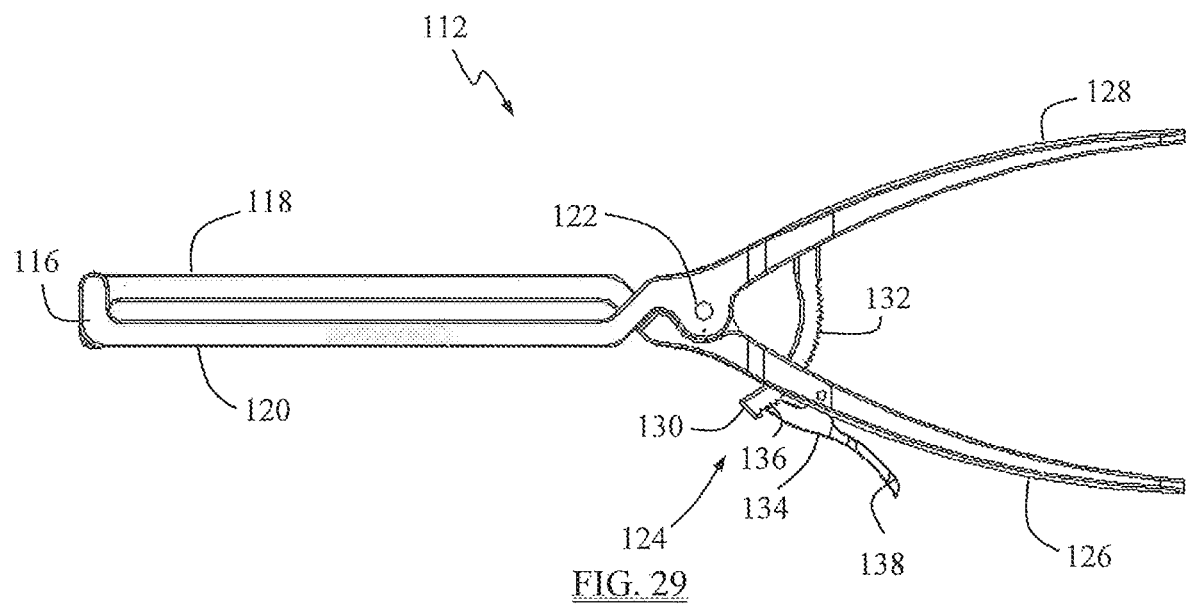
FIGS. 29-30 are side views of a retractor blade expander tool according to one embodiment of the present invention, shown in initial closed and secondary open positions, respectively.
Figure 30:
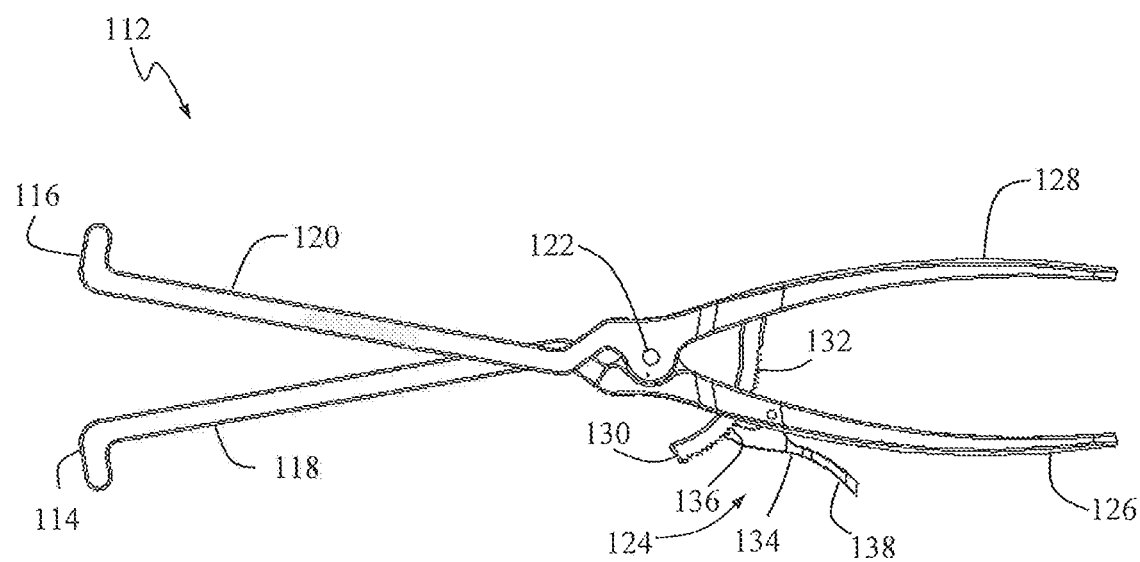

Initially, the retractor assembly 10 of the present invention is introduced to the surgical target site with the retractor blades 12, 16, 18 in a first, closed position (shown generally in FIGS. 2-3). In this configuration, the retractor blades 16, 18 are oriented in a generally perpendicular configuration. In some instances it may be desirable to pivot either the second retractor blade 16 or the third retractor blade 18 (or both) outward in order to increase the volume of the operative corridor 15 (by increasing the distal dimension of the operative corridor). To accomplish this (with respect to blade 16), a pivot wrench 106 is engaged to the distal pivot member 70 of arm 26, as shown in FIGS. 19-21. The pivot wrench 106 includes a gripping portion 108 and a handle 110. The gripping portion 108 is dimensioned to snugly interact with the distal pivot member 70 of arm 26. When the handle 110 is moved in a medial direction (relative to the retractor 10), the blade 16 will pivot in a lateral (outward) direction (FIGS. 21 and 25). Distal pivot member 70 of retractor arm 26 is configured in such a way that it prevents the blade 16 from pivoting in a medial direction. In this manner, the blade 16 may be pivoted to a desired angulation (any angle between 0 and 45 degrees from center, denoted by δ1 & δ2 in FIG. 25). While maintaining this desired angulation, the user may engage the user engagement region 92 and exert a force to slide the variable-stop lock 88 in a distal direction along locking bar 94 (FIGS. 22 and 26) until the sequential step-wise cutout region 96, 98, 100, 102 corresponding to the particular angulation engages the distal pivot member 70 of the first arm member 26. By way of example only, if a 5° angulation is desired, cutout region 96 will interact with the distal pivot member 70, preventing further pivoting of the retractor blade 16. On the other hand, if a 15° angulation is desired, the variable-stop lock 88 should be moved along locking bar 94 until cutout region 100 interacts with the distal pivot member 70 (shown, by way of example in FIGS. 22-23). After engaging the variable-stop lock 88, the pivot wrench 106 may be removed because the retractor blades 16, 18 are locked into a desired degree of angulation (FIGS. 27-28).

Although described with reference to first arm member 26, it will be appreciated that the detailed features and operation of the present invention as embodied within first arm member 26 are generally applicable (though in a mirror-image orientation) to the second arm member 28. Furthermore, the blade 18 may be pivoted independently of blade 16 such that different angles for each blade 16, 18 are achieved. Thus, it may be desirable to use blades of differing lengths and still maintain a symmetrical operating corridor wherein the distal ends of blades 16, 18 are oriented along the same general plane. Before removing the tissue retraction system 10 from the operative corridor, the variable-stop lock 88 should be disengaged by sliding it in a proximal direction along locking bar 94, allowing retractor blades 16, 18 to return to an initial alignment to facilitate removal.

As an alternative to the pivot wrench 106, a blade expander 112, such as shown by way of example only in FIGS. 29-33, may be provided to facilitate the manual pivoting of the retractor blades 16, 18. The blade expander 112 may include first and second blade engagement members 114, 116 located on first and second elongated extenders 118, 120, respectively, a pivot joint 122, a locking element 124 and pair of handle extensions 126, 128. By way of example only, the locking element 124 may include a generally curved member 130 including a series of engagement features 132 located along one edge. By way of example only, the engagement features 132 may consist of a series of "teeth" having a generally triangular cross-section. The locking element 124 may further include a release member 134 including a series of engagement features 136 that interact with engagement features 132 to effectively lock the blade expander 112 in a second variable configuration. The release member 134 further includes a manual depressor 138 that, when depressed, causes engagement features 136 to disengage from engagement features 132, allowing blade expander 112 to return from a second configuration to a first configuration.

Figure 31:
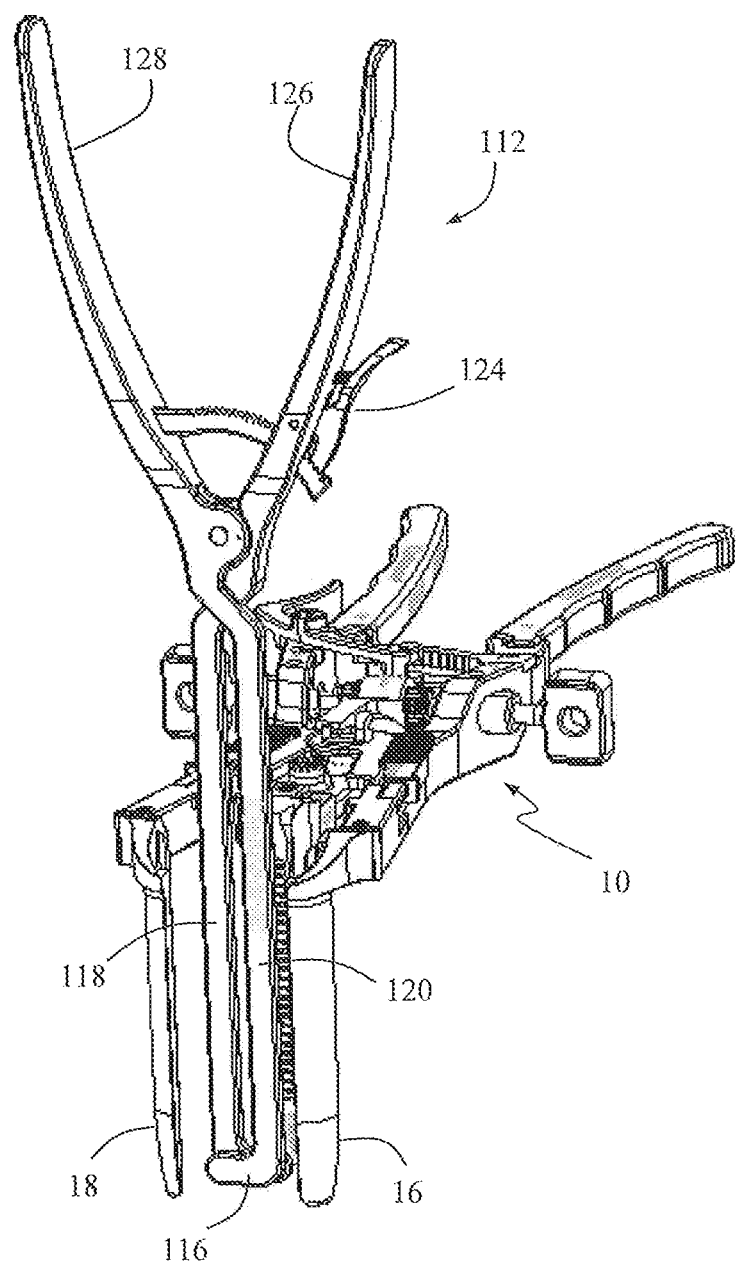
FIG. 31 is a perspective view of a retractor blade expander tool of FIG. 29 inserted into an operative corridor formed by the tissue retraction assembly of FIG. 1 with the blades in a retracted position.
Figure 32:
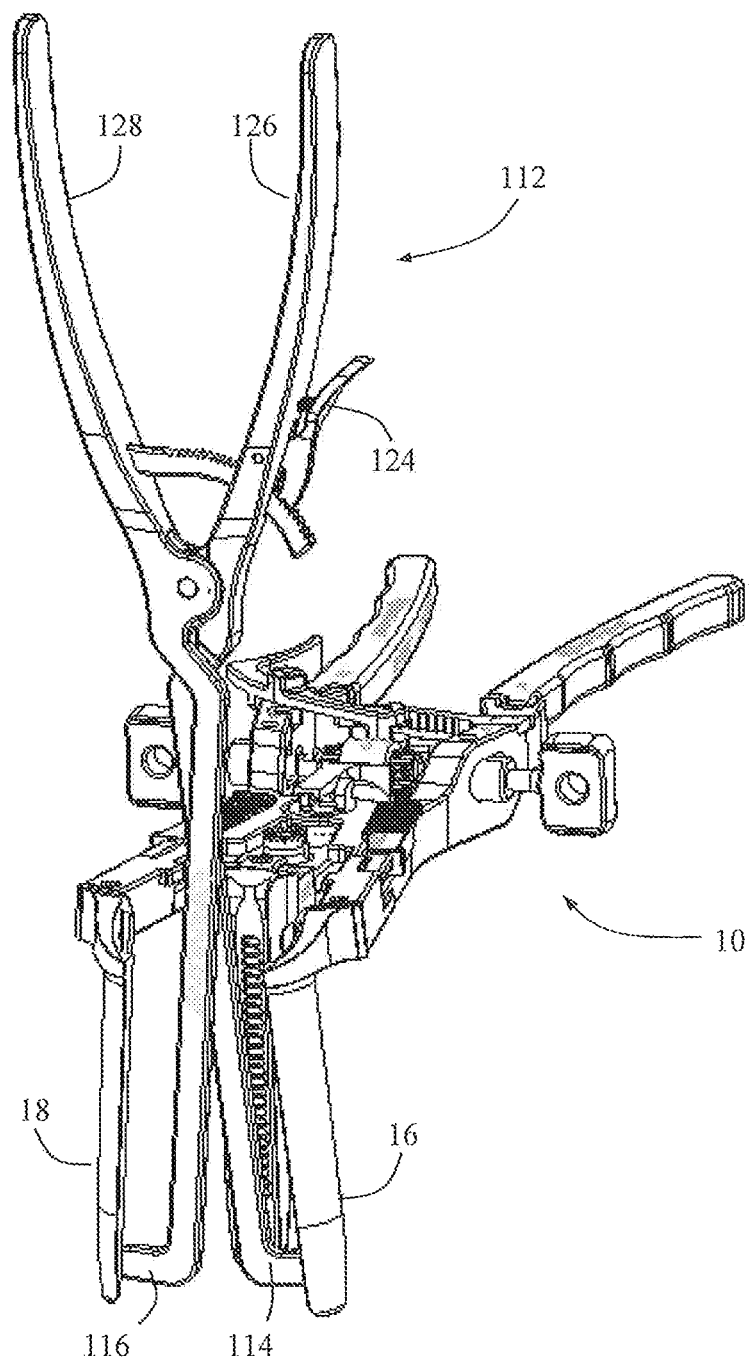
FIGS. 32-33 are perspective views of the retractor blade expander tool of FIG. 31 in an open position causing the cephalad-most and caudal-most retractor blades of the tissue retraction assembly of FIG. 31 to pivot in an outward direction.
Figure 33:
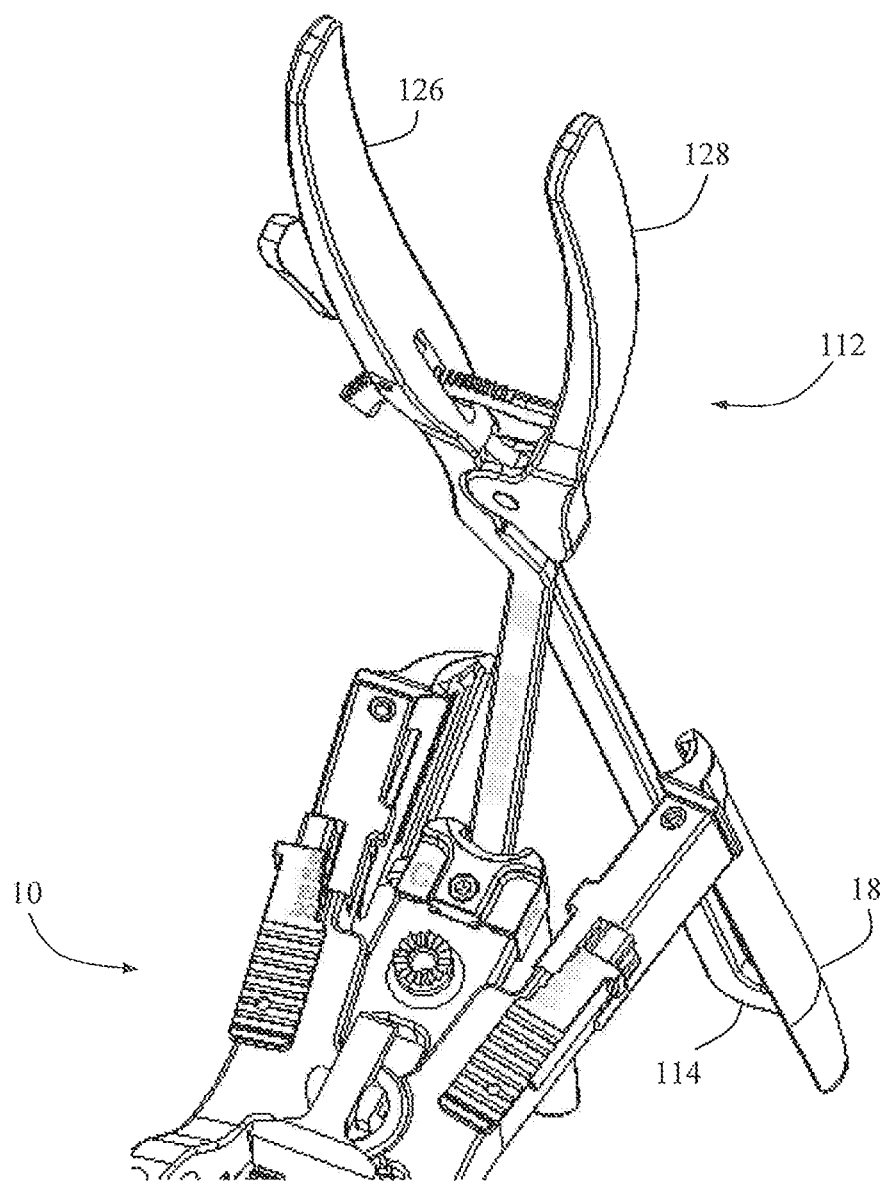
Figure 34:
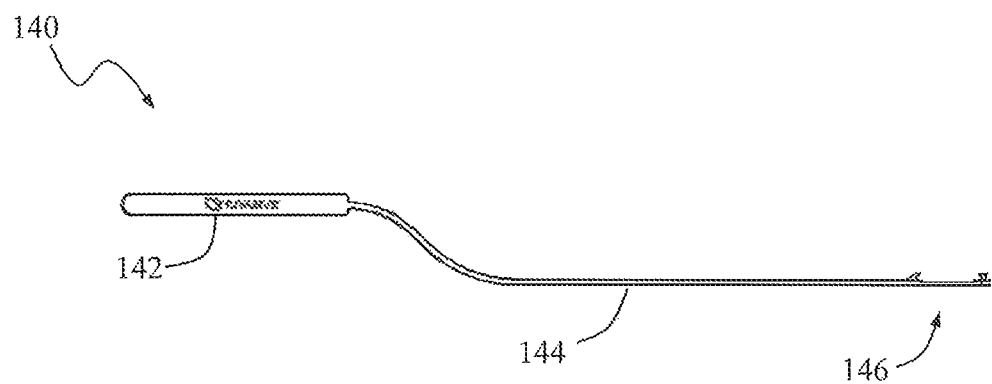
FIGS. 34-35 are side and perspective views, respectively, of a shim inserter according to a preferred embodiment of the present invention.
Figure 35:
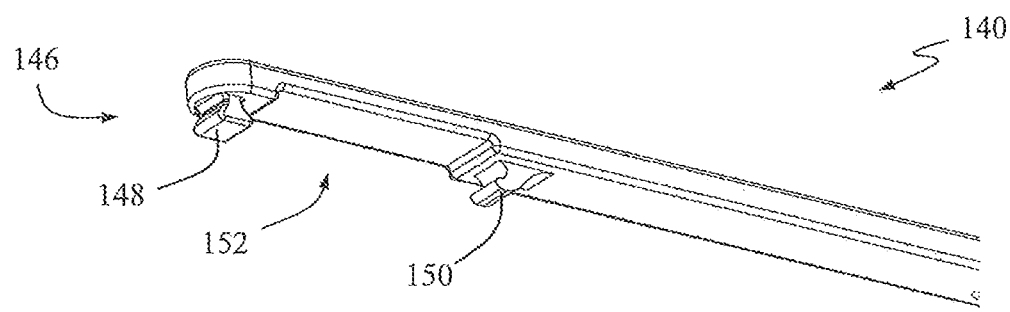

With the retractor blades 16, 18 in an initial alignment (i.e. generally perpendicular to the handle 20) and the first and second arm members 26, 28 in an "open" position, the blade expander 112 may be inserted into the operative corridor in a first "closed" position, as shown by way of example in FIG. 31. The blade engagement members 114, 116 may be positioned to interact with the retractor blades 16, 18, respectively. The user may then operate the blade expander 112 by squeezing handle extensions 126, 128, thereby causing first and second elongated extenders 118, 120 to spread apart into a second "open" position shown generally in FIG. 30. Blade engagement members 114, 116 are thus forced against the retractor blades 16, 18, causing distal pivot members 70, 71 to pivot in an outward direction (shown by way of example in FIGS. 32-33). Once the desired degree of angulation (secondary alignment) of the retractor blades 16, 18 is achieved, the user should cease squeezing the handle extensions 126, 128. Due to the interaction between engagement features 132, 136 of the locking element 124, the blade expander 112 is effectively locked in this second position. When desired, the blade expander 112 may be returned to a first closed position by engaging manual depressor 138 on release member 134, allowing blade expander 112 to be removed from the operative corridor 15.

Figure 36:
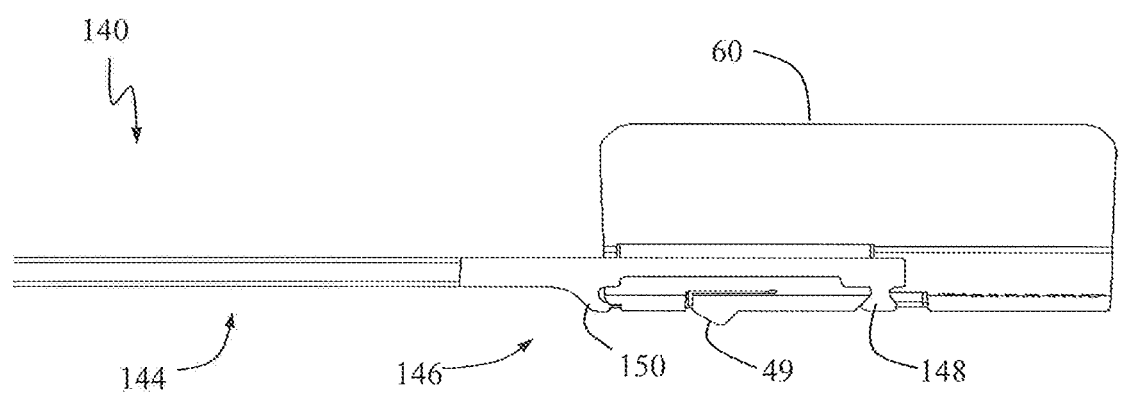
FIGS. 36-37 are side and perspective views, respectively, the shim inserter of FIG. 34 coupled to a shim.
Figure 37:
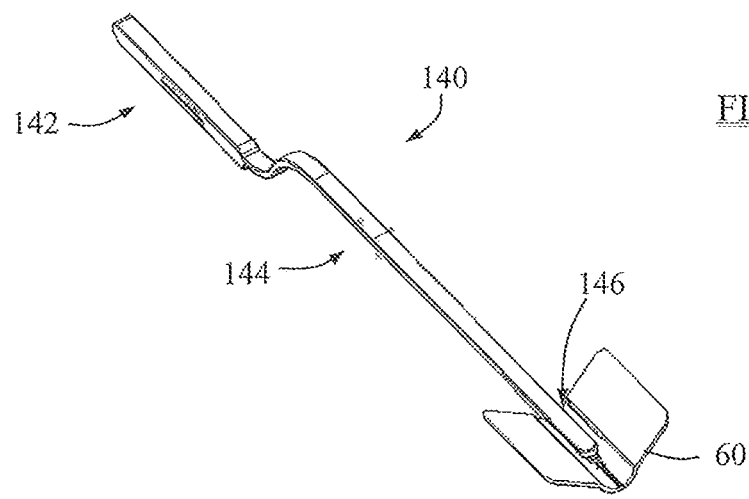

FIGS. 34-38 illustrate an inserter 140 for inserting retractor extenders 22, 24, 60 and/or shim element 25 according to a preferred embodiment of the present invention. By way of example only, inserter 140 is shown and described herein in conjunction with retractor extender 60, although it is to be readily appreciated that the inserter 140 may be employed in a similar manner with retractor extenders 22, 24 and shim element 25 according to the present invention. Inserter 140 includes a handle 142, and elongated region 144, and a distal end 146. The handle 142 may be any configuration suitable to allow purchase with the human hand, including but not limited to a grip (composed of any suitable material including but not limited to rubber, plastic, or metal) or a T-handle. The elongated region 144 may be straight or included any number of curved regions, and may be of any length necessary to mate the retractor extender 60 with the retractor blade 16/18. The distal end 146 may include a distal stub 148, a grip protrusion 150, and a recessed region 152. The distal stub 148 is configured to interact with elongated slot 43 of retractor extender 60 such that the retractor extender 60 is rigid relative to the inserter 140. Grip protrusion 150 is dimensioned to engage snugly over the edge of retractor extender 60 such that the retractor extender 60 is locked into place on the inserter 140 (FIG. 36).

Figure 38:
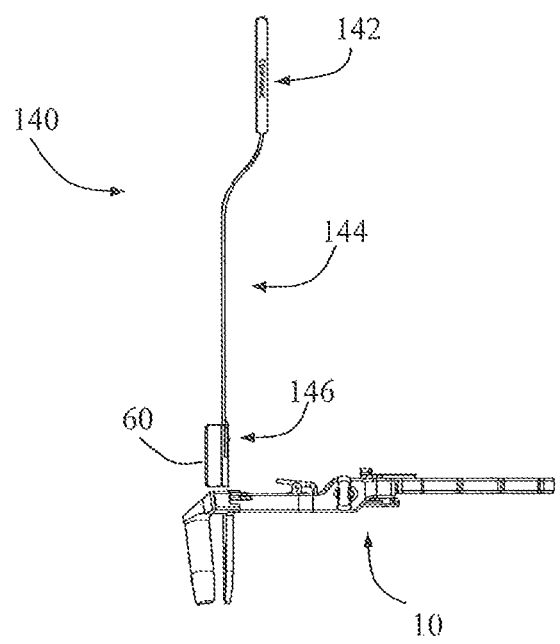
FIGS. 38-39 are side and top views, respectively, of the shim inserter of FIG. 36 prior to insertion of the shim.
Figure 39:
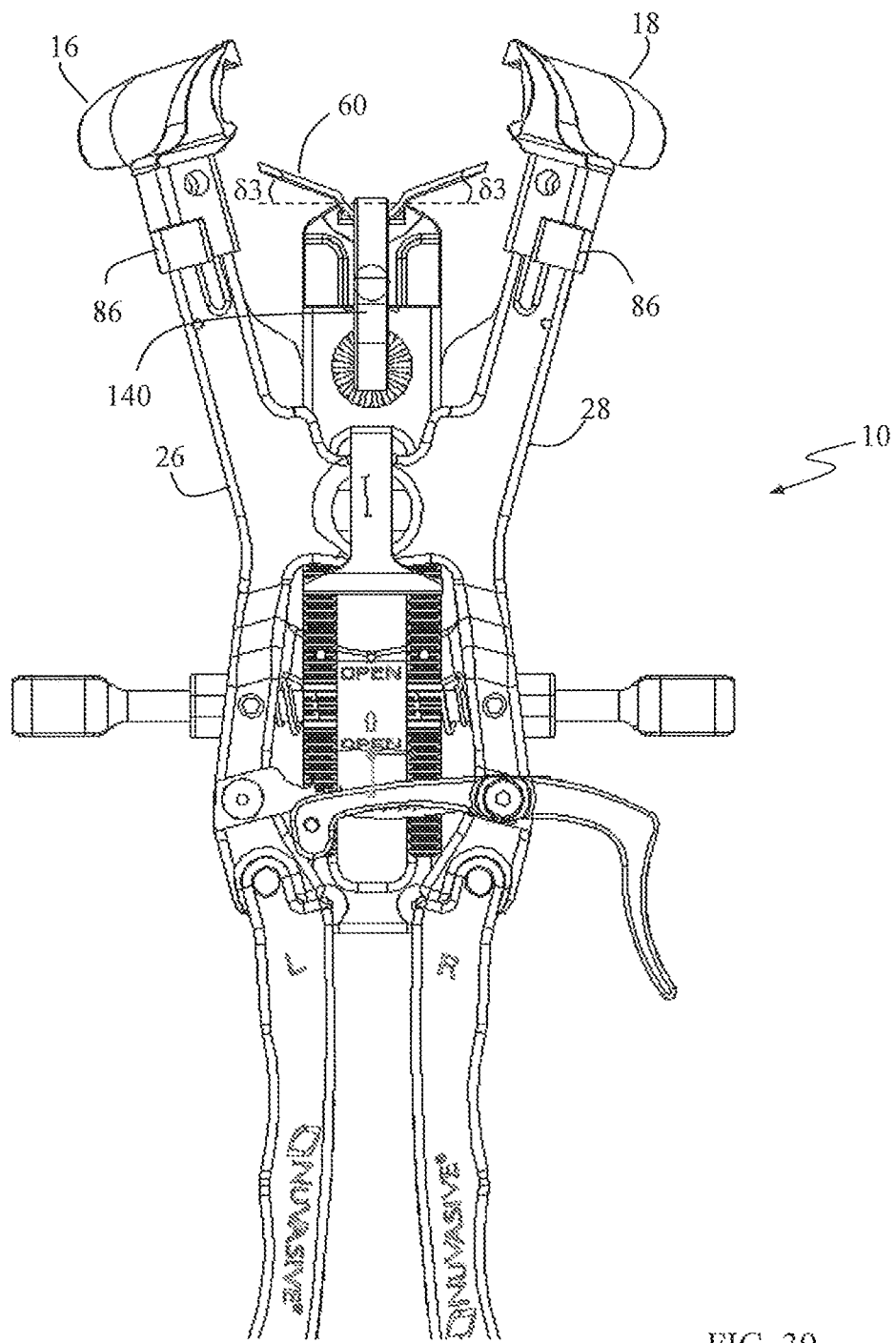
Figure 40:
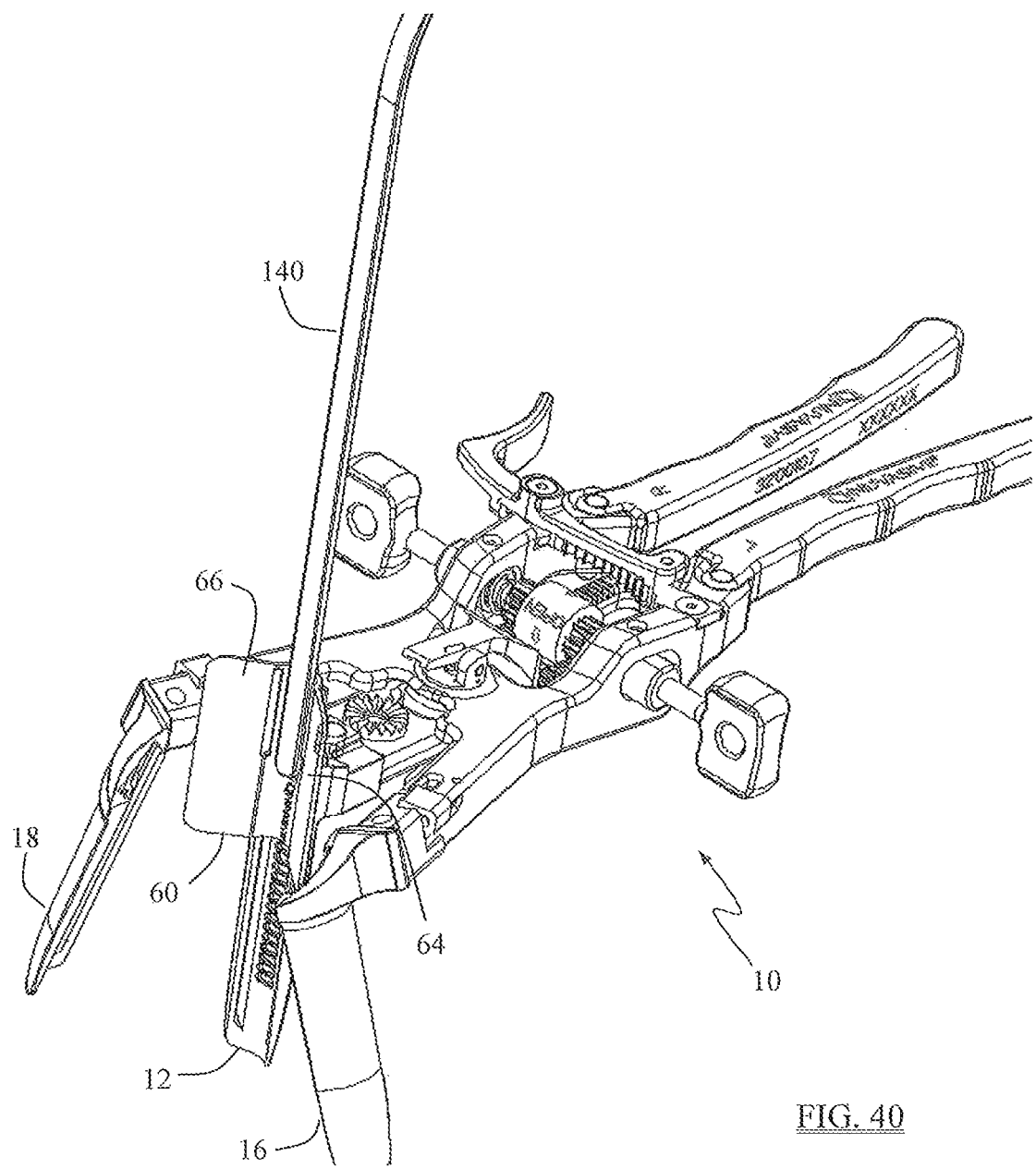
FIGS. 40-41 are perspective and top views, respectively, of a shim inserter according to the present invention coupled to a shim in the initial phase of insertion, where the shim is entering the operative corridor at the skin level.
Figure 41:
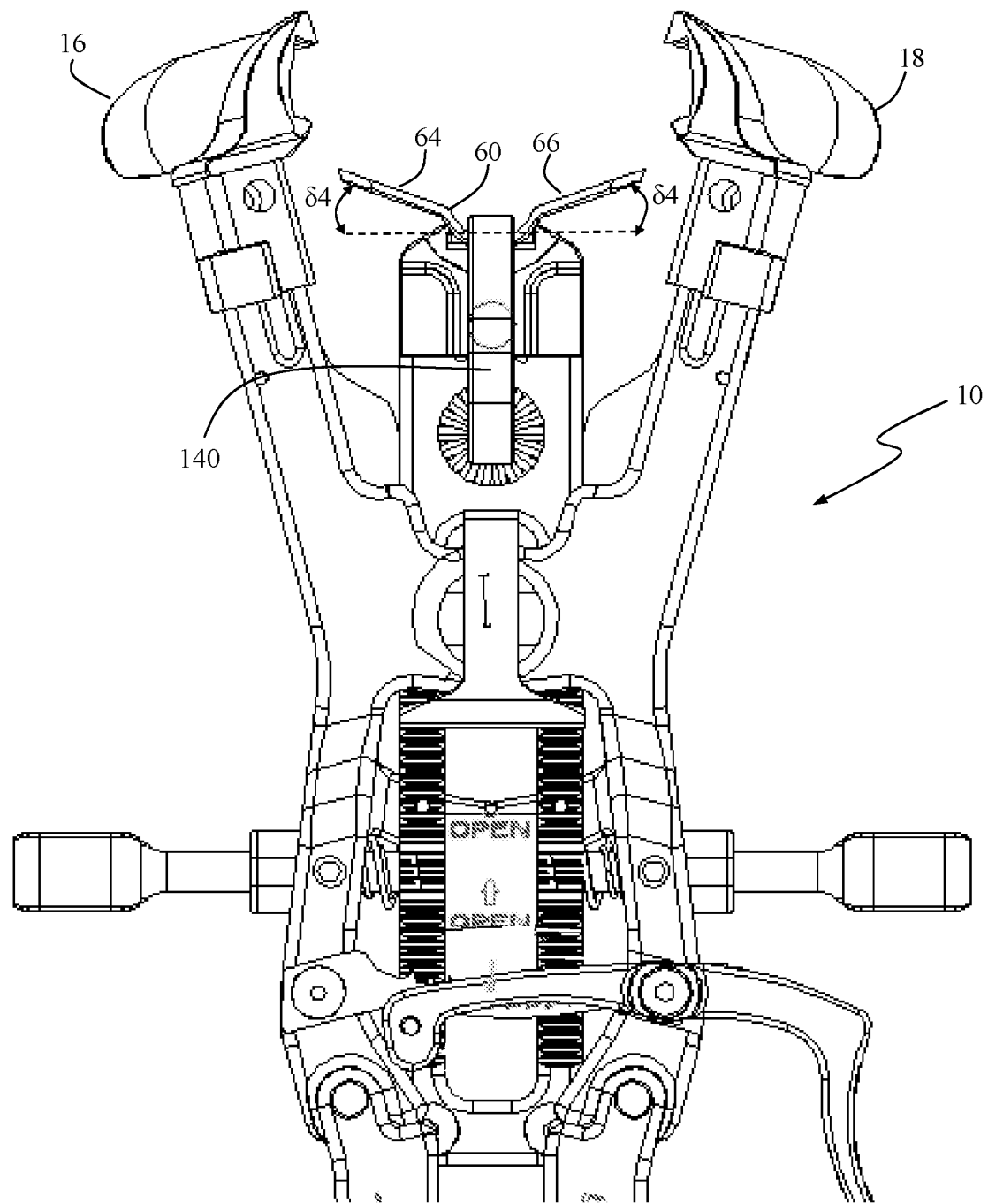
Figure 42:
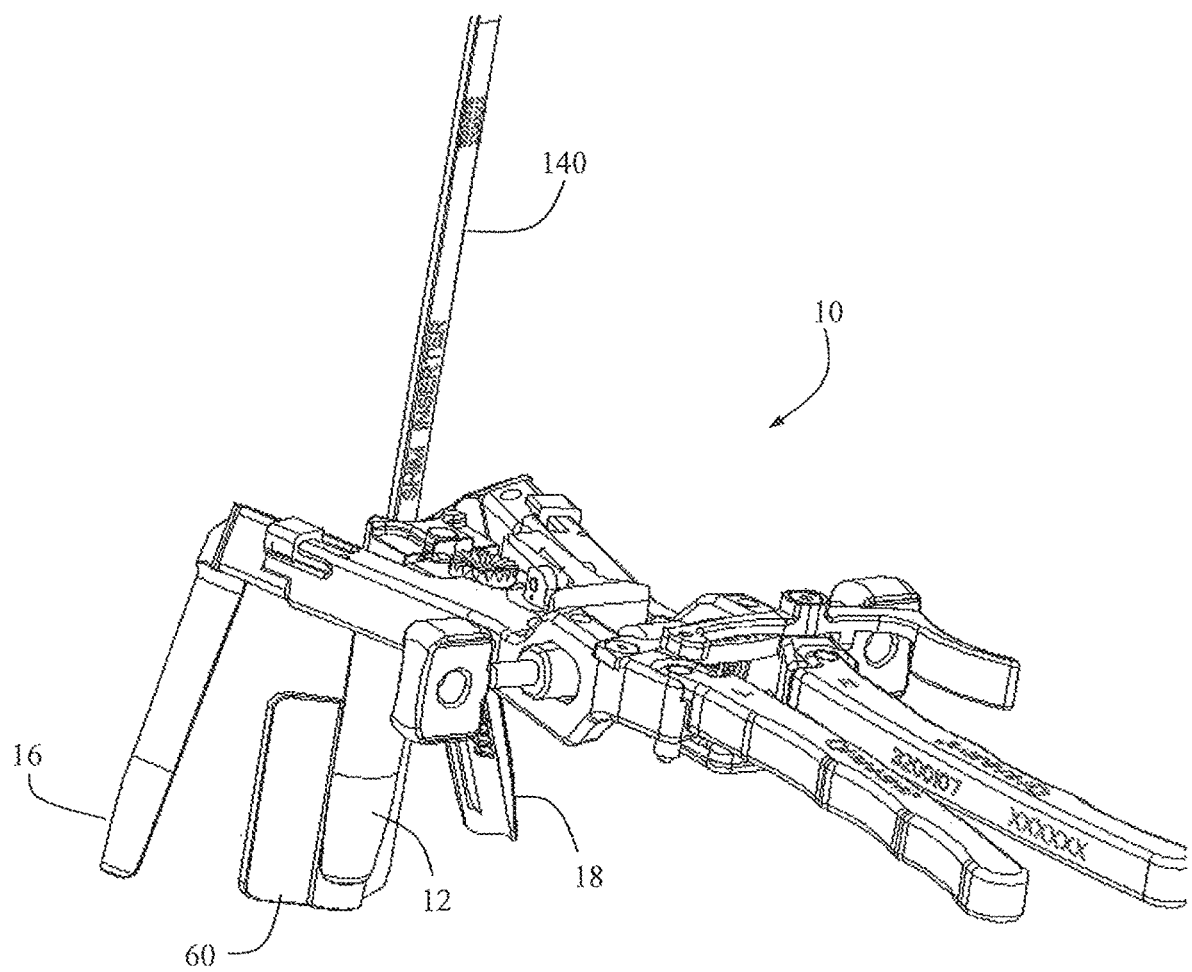
FIGS. 42-43 are perspective and top views, respectively, of the shim inserter & shim of FIG. 52, where the shim has been inserted beyond the skin level and fully into the operative corridor.
Figure 43:
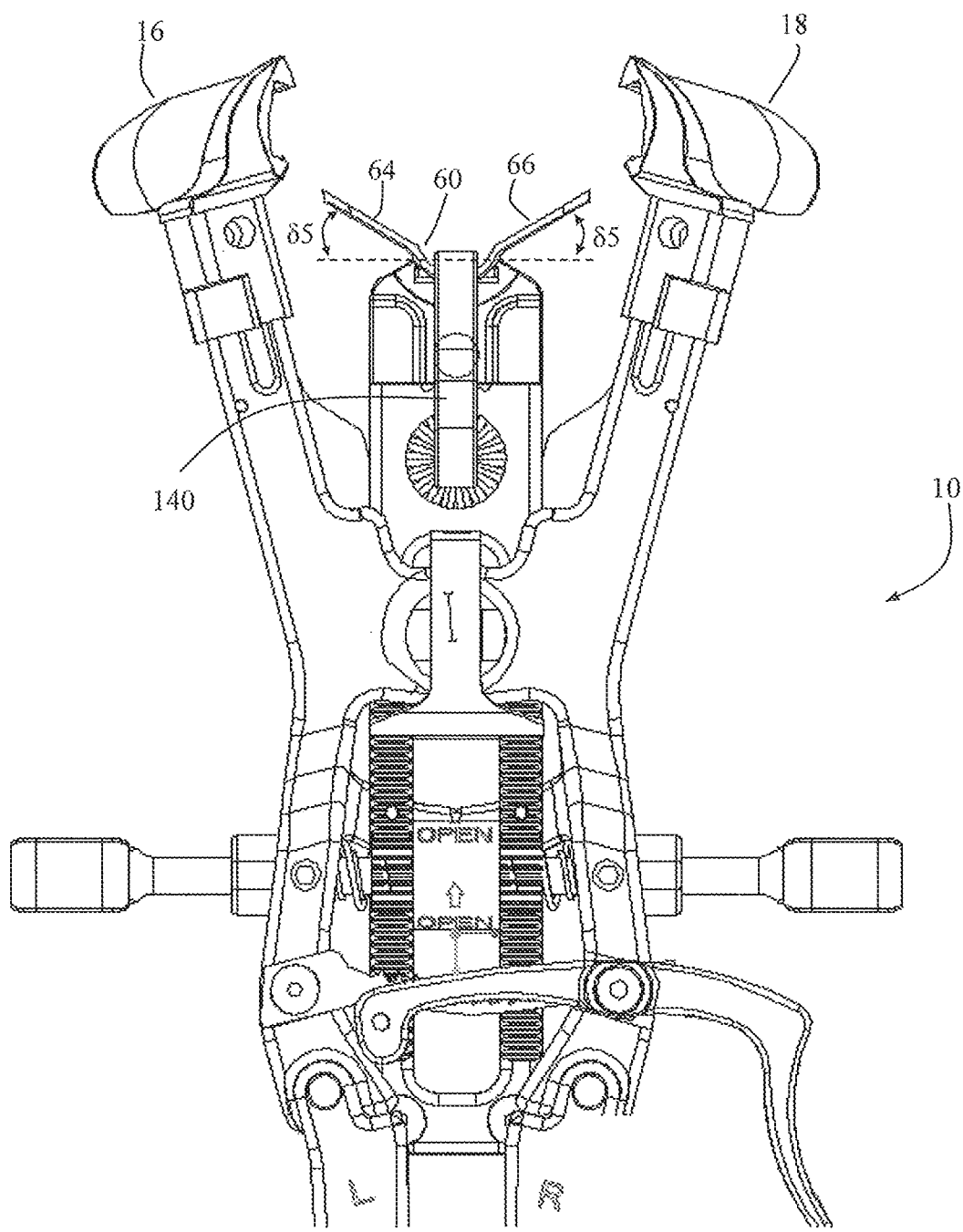
Figure 44:
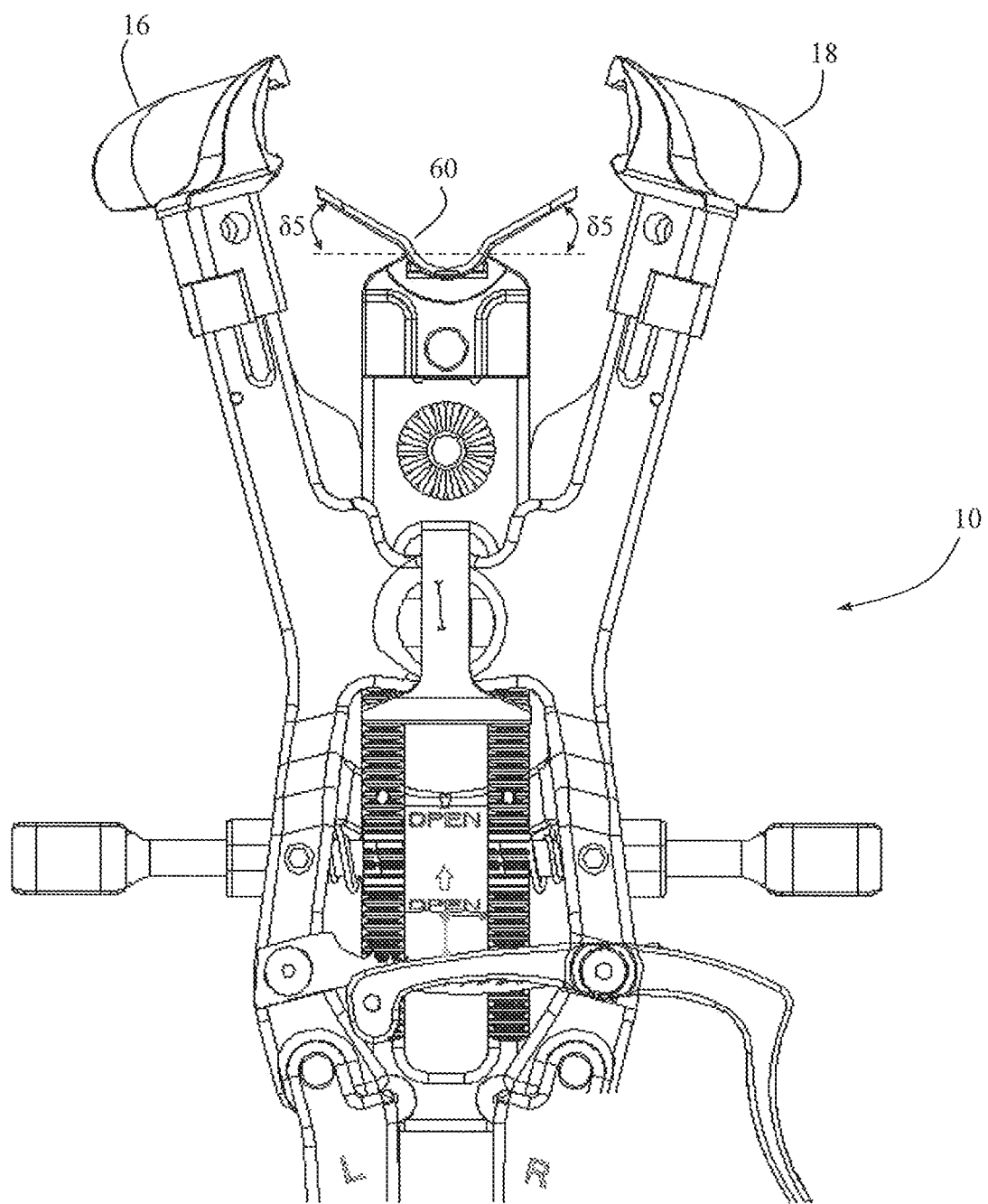
FIGS. 44-45 are top and perspective views, respectively, of a fully inserted shim, wherein the shim inserter has been removed.
Figure 45:
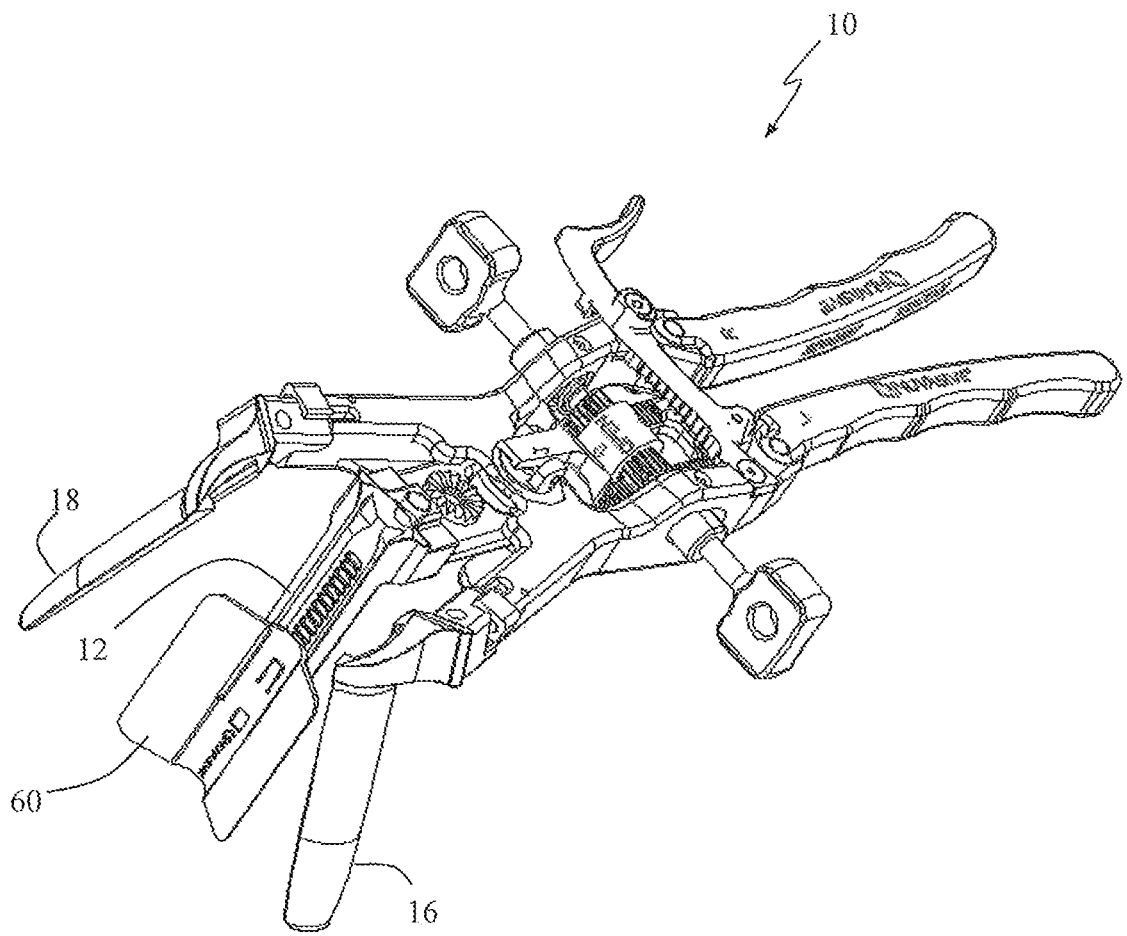

In use, once the retractor extender 60 is attached to the inserter 140 (FIG. 37), the retractor extender 60/inserter 140 combination is positioned over the desired retractor blade (shown as the posterior blade 12 in FIG. 38). As the retractor extender 60 is inserted through the operative opening at the level of the skin (FIGS. 40-41), the retractor extender 60 may compress together such that the panels 64, 66 are oriented at a greater angle (denoted by $\delta4$ in FIG. 41) than at default position (denoted by $\delta3$ in FIG. 39). As the retractor extender 60 is inserted beyond the level of the skin and into the operative corridor 15 (FIGS. 42-43), the panels 64, 66 may expand to a lesser angle (denoted by $\delta5$ in FIG. 43), which may or may not be the same angle as in default position. Once the retractor extender 60 has been inserted onto the retractor blade 12, the inserter 140 may be removed (FIGS. 44-45).

Figure 46:
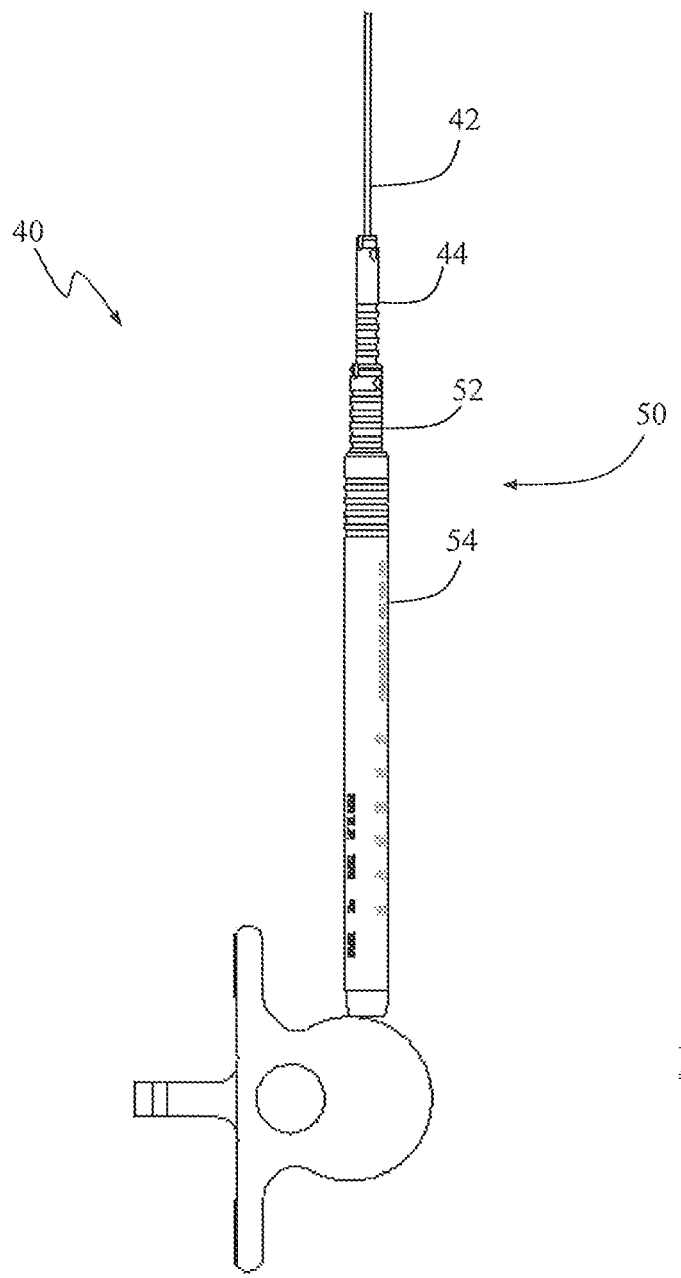
FIG. 46 is a side view illustrating the use of a tissue distraction assembly (comprising a plurality of dilating cannulae over a K-wire) to distract tissue between the skin of the patient and the surgical target site according to the present invention.

FIG. 46 illustrates a tissue distraction assembly 40 forming part of the surgical access system according to the present invention. The tissue distraction assembly 40 includes a K-wire 42, an initial dilating cannula 44, and a sequential dilation system 50. In use, the K-wire 42 is disposed within the initial dilating cannula 44 and the assembly is advanced through the tissue towards the surgical target site (e.g. stimulus). Again, this is preferably accomplished while employing the nerve detection and/or direction features described above. After the initial dilating assembly is advanced such that the distal end of the initial dilator 44 is positioned within the disc space, the sequential dilation system 50 consisting of one or more supplemental dilators 52, 54 may be employed for the purpose of further dilating the tissue down to the surgical target site. Once again, each component of the sequential dilation system 50 (namely, the K-wire 42 and the supplemental dilators 52, 54) may be, according to the present invention, provided with one or more electrodes (preferably at their distal regions) equipped for use with a nerve surveillance system, such as, by way of example, the type shown and described in the NeuroVision PCT Applications.

Figure 47:
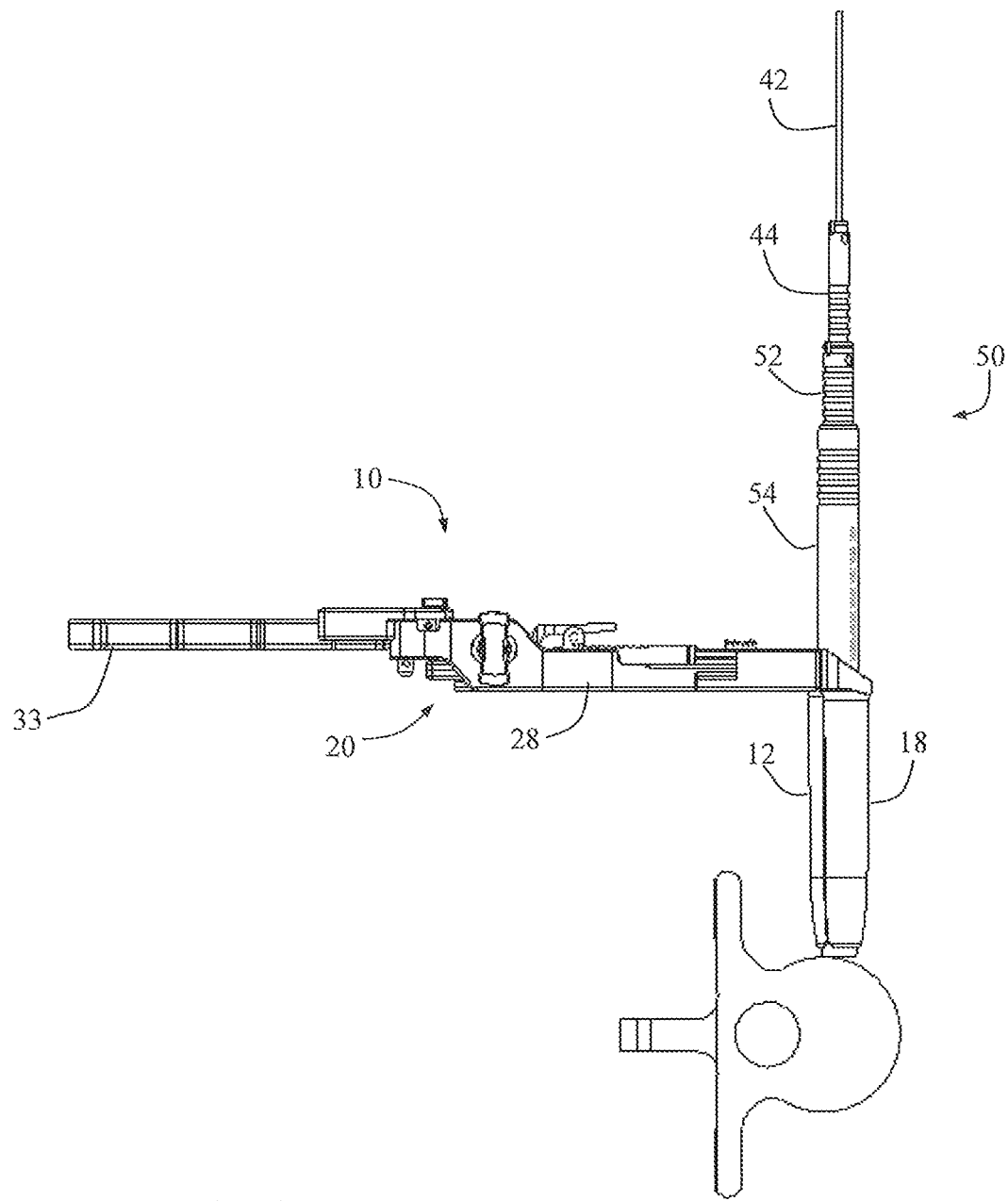
FIG. 47 is a side view of a retractor assembly according to the present invention, comprising a handle assembly having three (3) retractor blades extending there from (posterior, cephalad-most, and caudal-most), shown in a first, closed position and disposed over the tissue distraction assembly of FIG. 46.
Figure 48:
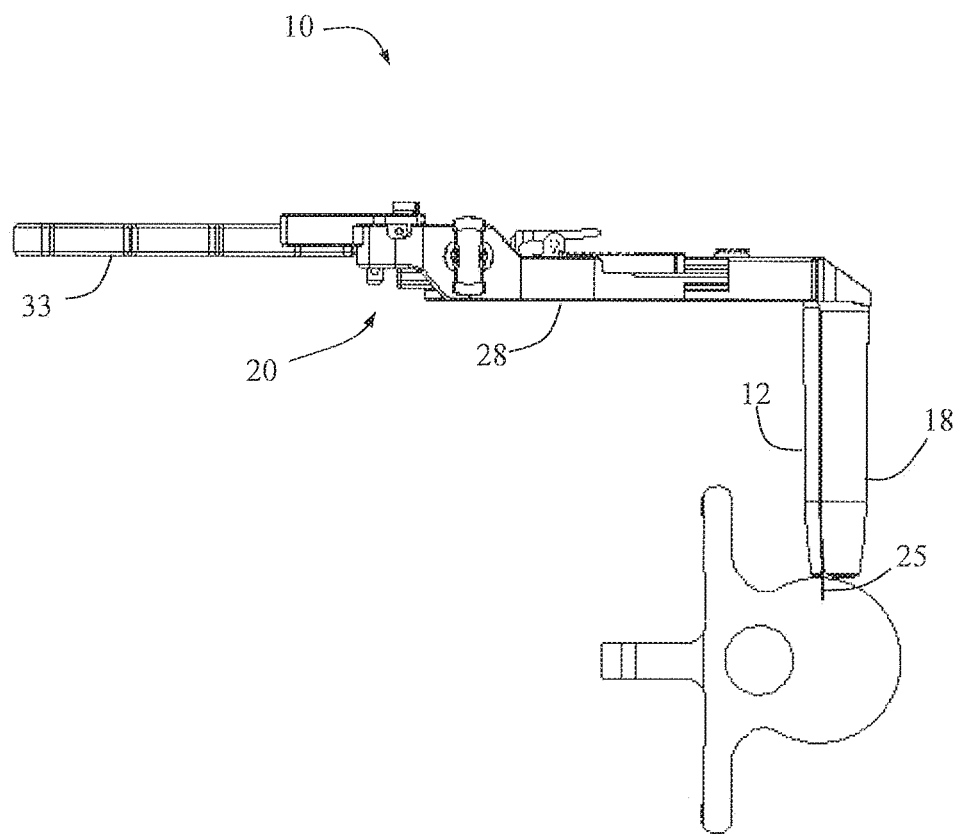
FIG. 48 is a side view of a retractor assembly according to the present invention, comprising a handle assembly having three (3) retractor blades extending there from (posterior, cephalad-most, and caudal-most) with the tissue distraction assembly of FIG. 46 removed and shim element introduced.
Figure 49:
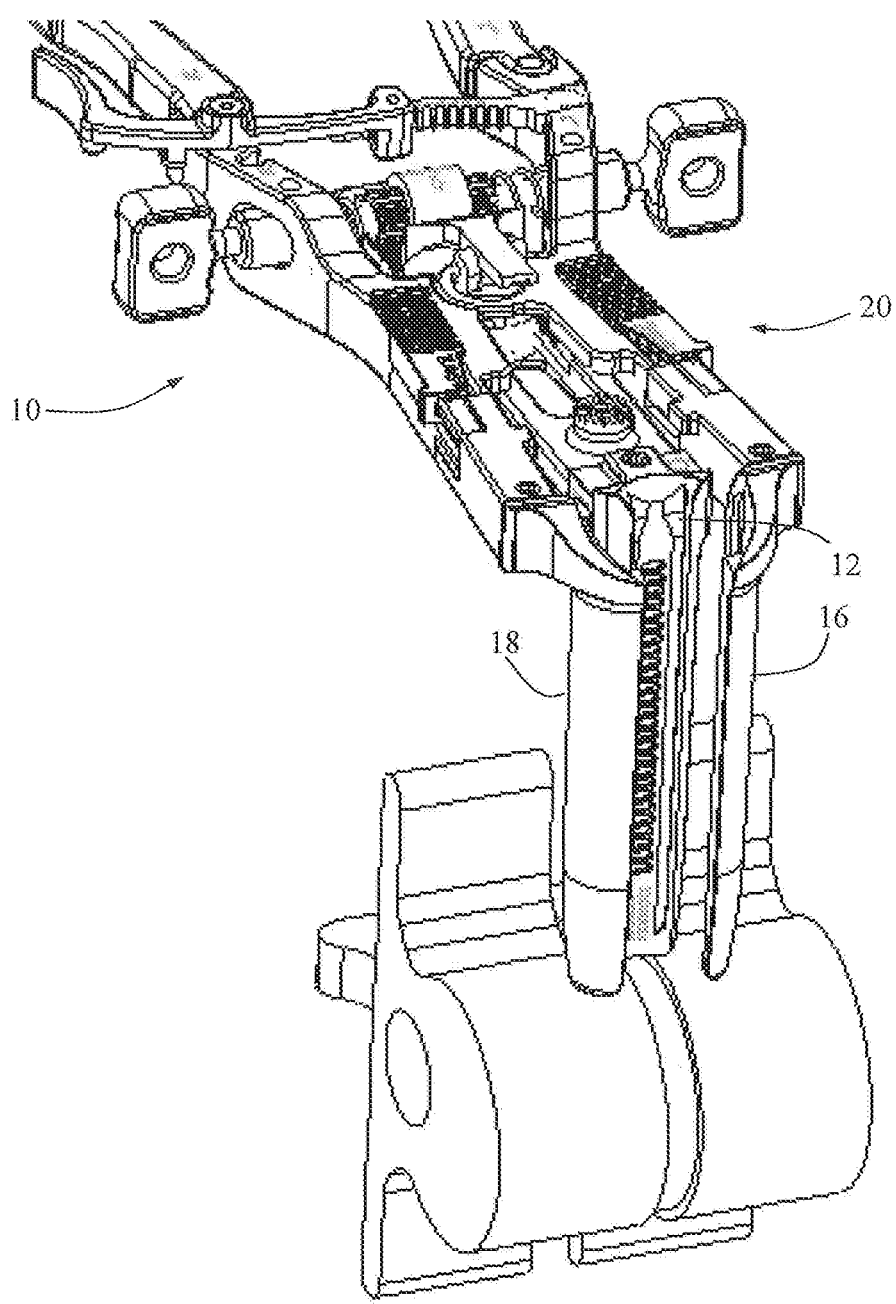
FIG. 49-50 are perspective and top views, respectively, of the retractor assembly in a second, opened (i.e. retracted) position to thereby create an operative corridor to a surgical target site according to the present invention.
Figure 50:
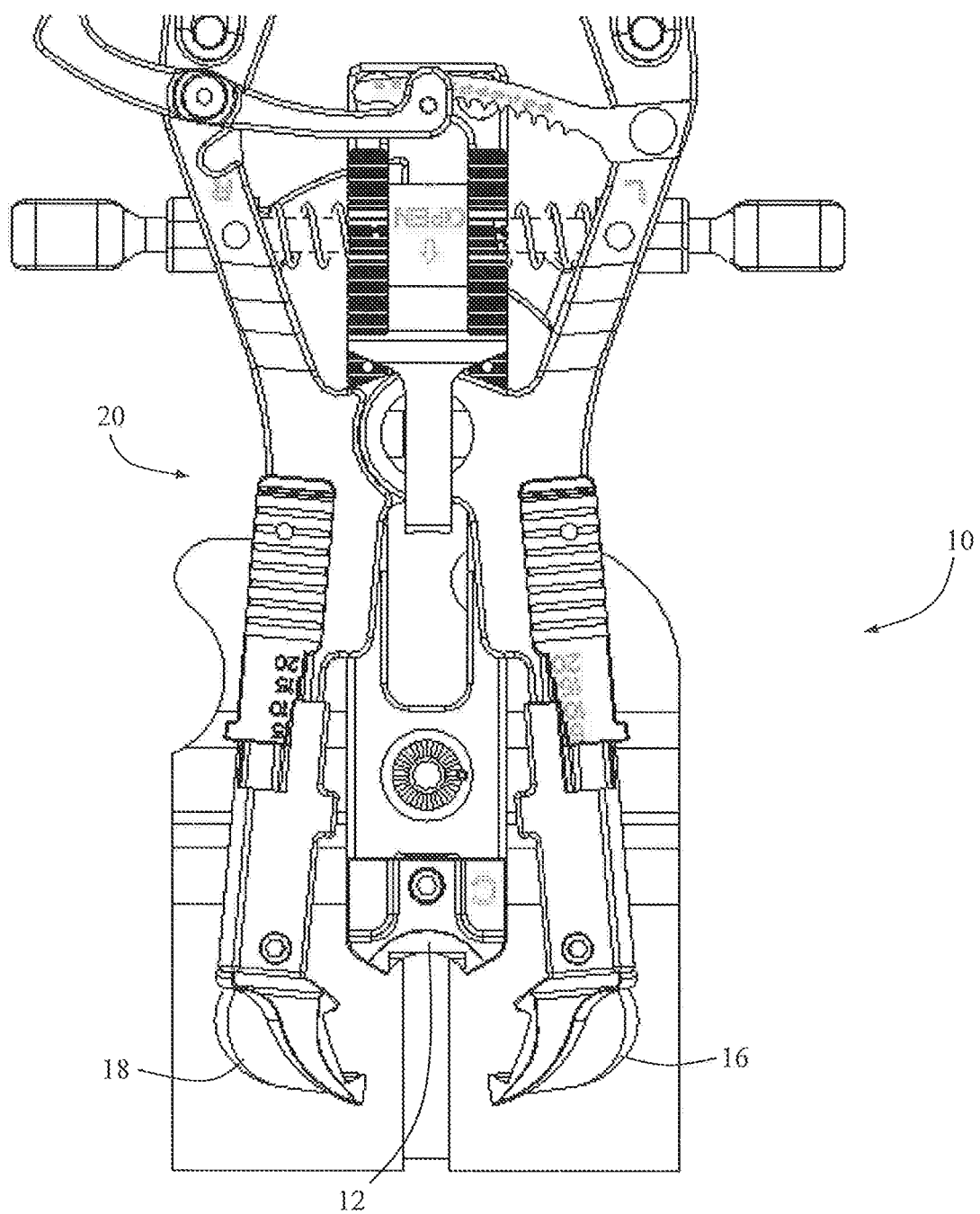
Figure 51:
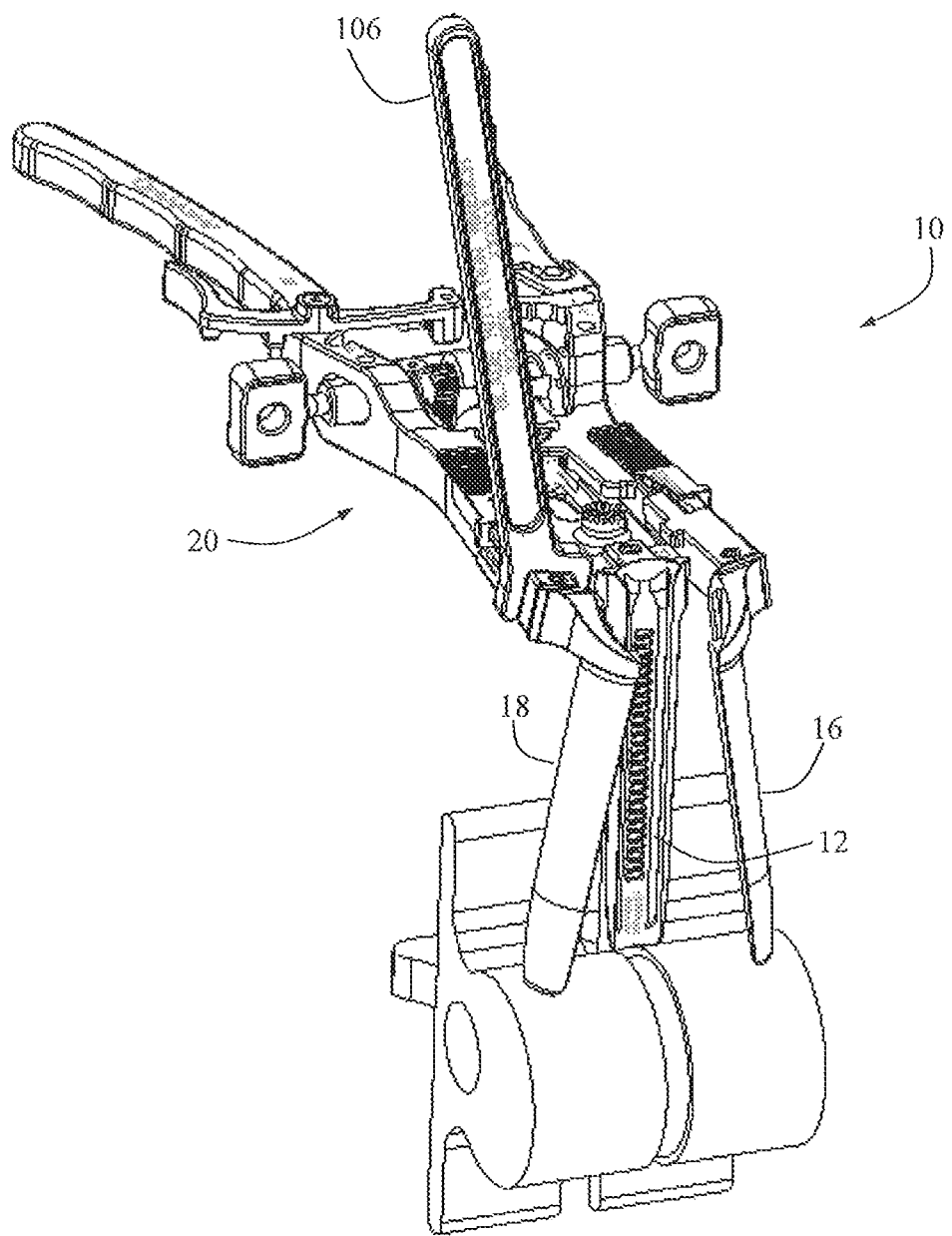
FIGS. 51-52 are perspective views of the retractor assembly of FIG. 50 with the retractor arms in a pivoted position.
Figure 52:
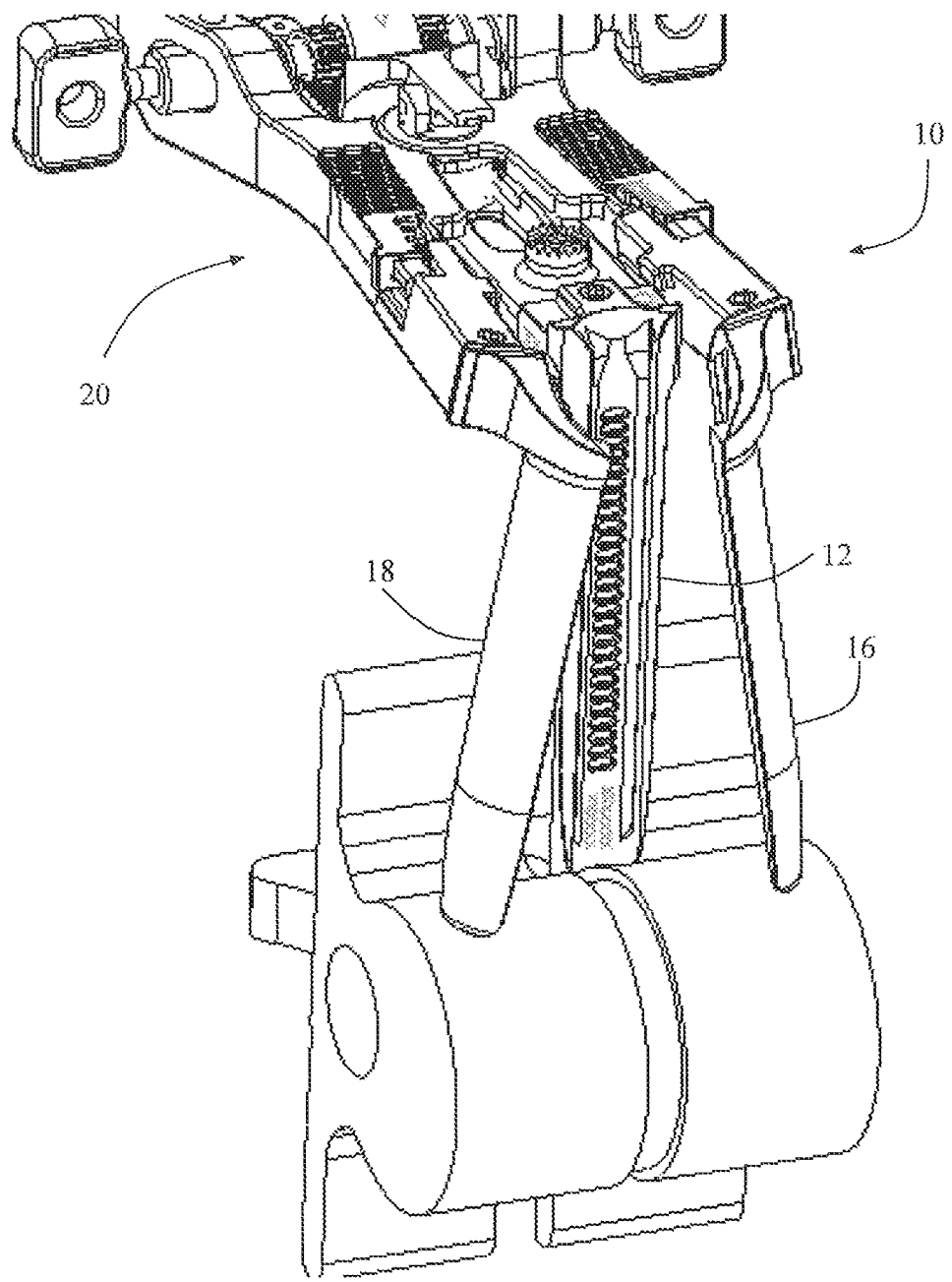
Figure 53:
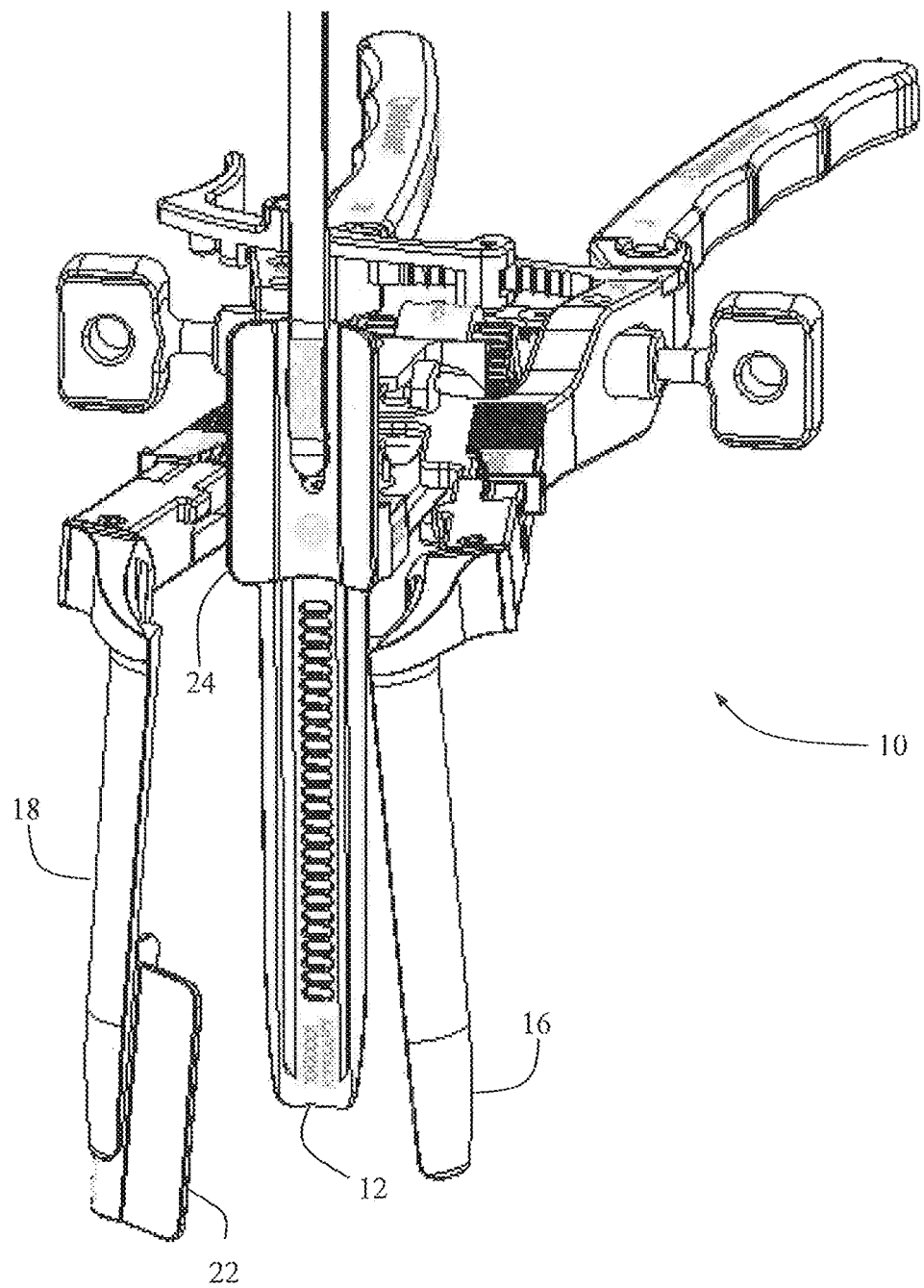
FIG. 53 is a perspective view of the retractor assembly in the second, opened (i.e. retracted) position (with the secondary distraction assembly removed) and with one retractor extender of FIGS. 6-7 coupled to a retractor blade and another retractor being inserted onto a second retractor blade according to the present invention.

As shown in FIG. 47, the retraction assembly 10 of the present invention is thereafter advanced along the exterior of the sequential dilation system 50. This is accomplished by maintaining the retractor blades 12, 16, 18 in a first, closed position (with the retractor blades 12-16 in generally abutting relation to one another as shown in FIGS. 2-5). Once advanced to the surgical target site, the sequential dilation assembly 50 may be removed and the shim element 25 engaged with the first retractor blade 12 such that the distal end thereof extends into the disc space as shown in FIG. 48. At this point, the handle assembly 20 may be operated to move the retractor blades 16, 18 into a second, "retracted" position as shown generally in FIGS. 49-50. As will be appreciated, the first retractor blade 12 is allowed to stay in the same general position during this process, such that the second and third retractor blades 16, 18 move away from the first retractor blade 12. Optionally, the second retractor blade 16 and/or the third retractor blade 18 may be pivoted in an outward direction as shown in FIGS. 51-52. At this point, the narrow and wide retractor extenders 22, 24, 60 may be engaged with any combination of retractor blades 12, 16, 18 as described above and as shown in FIG. 53.

Figure 54:
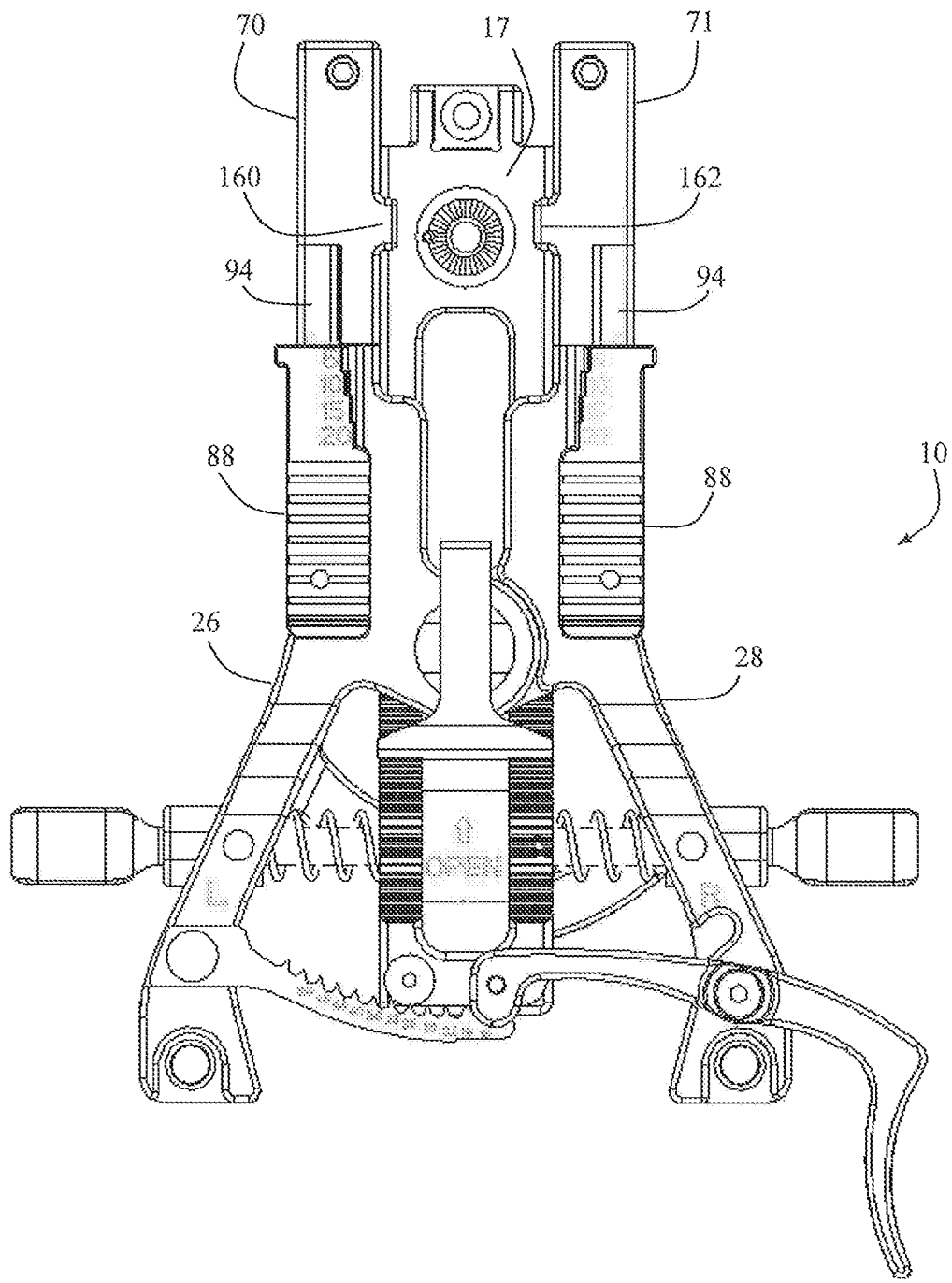
FIGS. 54-55 are perspective views of a handle assembly forming part of the tissue retraction assembly of FIG. 1 shown in an initial closed position.
Figure 55:
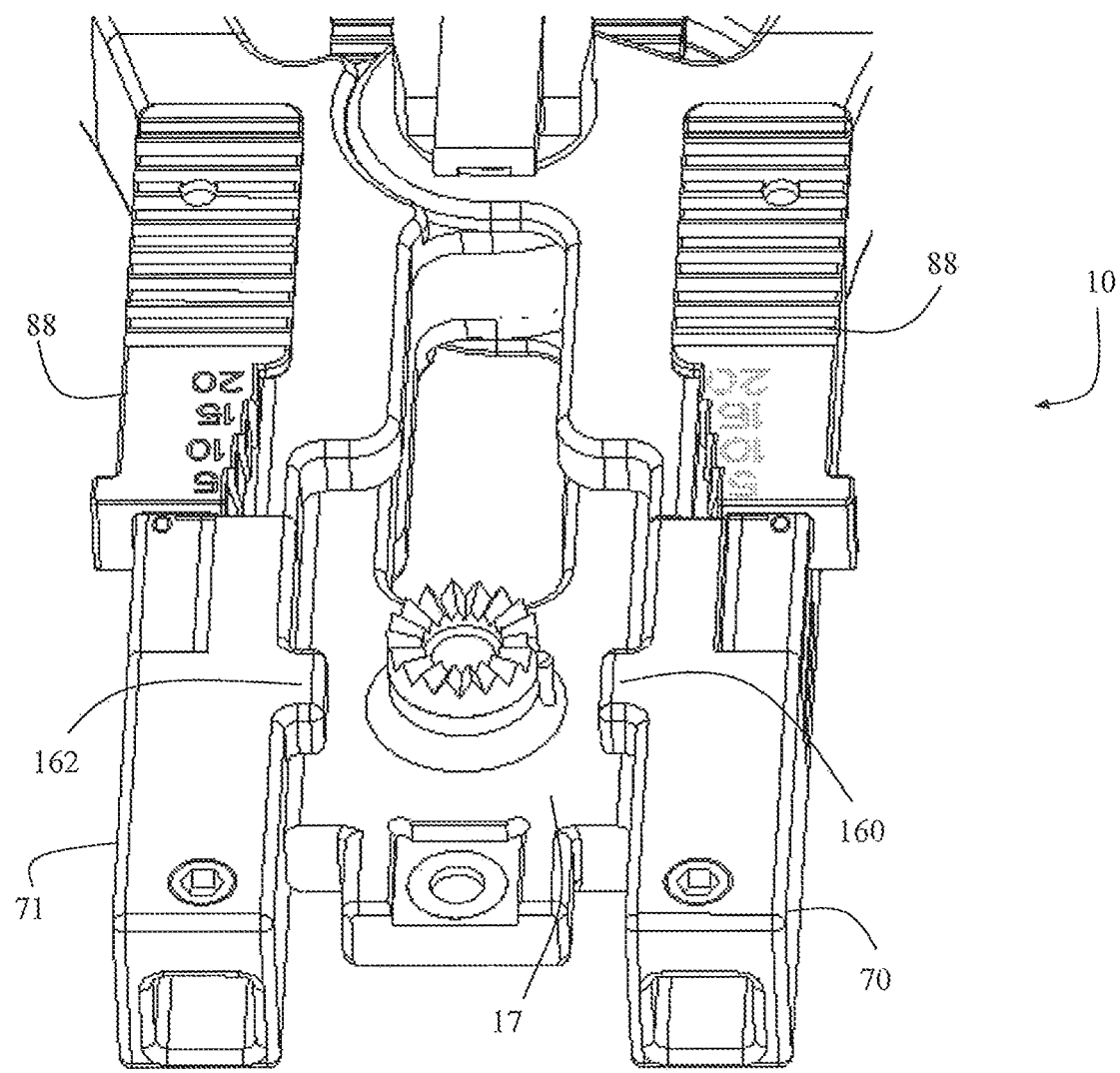

Various improvements and modifications may be made to the surgical access system disclosed herein without deviating from the scope of the present invention. For example, as exemplified in FIGS. 54-56, the tissue retraction system 10 may include an optional locking feature to maintain the blades 16, 18 in an initial alignment (e.g. generally parallel) during insertion. By way of example only, this locking feature may consist of a pair of tabs 160, 162 located on the distal pivot member 70, 71 of first and second arm members 26, 28, respectively. The tabs 160, 162 are dimensioned to extend at least partially over the translating member 17 such that when the tissue retraction system 10 is in an initial closed position as shown in FIGS. 54-55 (e.g. as the tissue retraction system 10 is advanced along the exterior of sequential dilation system 50), the distal pivot members 70, 71 are prevented from pivoting, thereby maintaining the retractor blades 16, 18 in an initial alignment.

Figure 24:
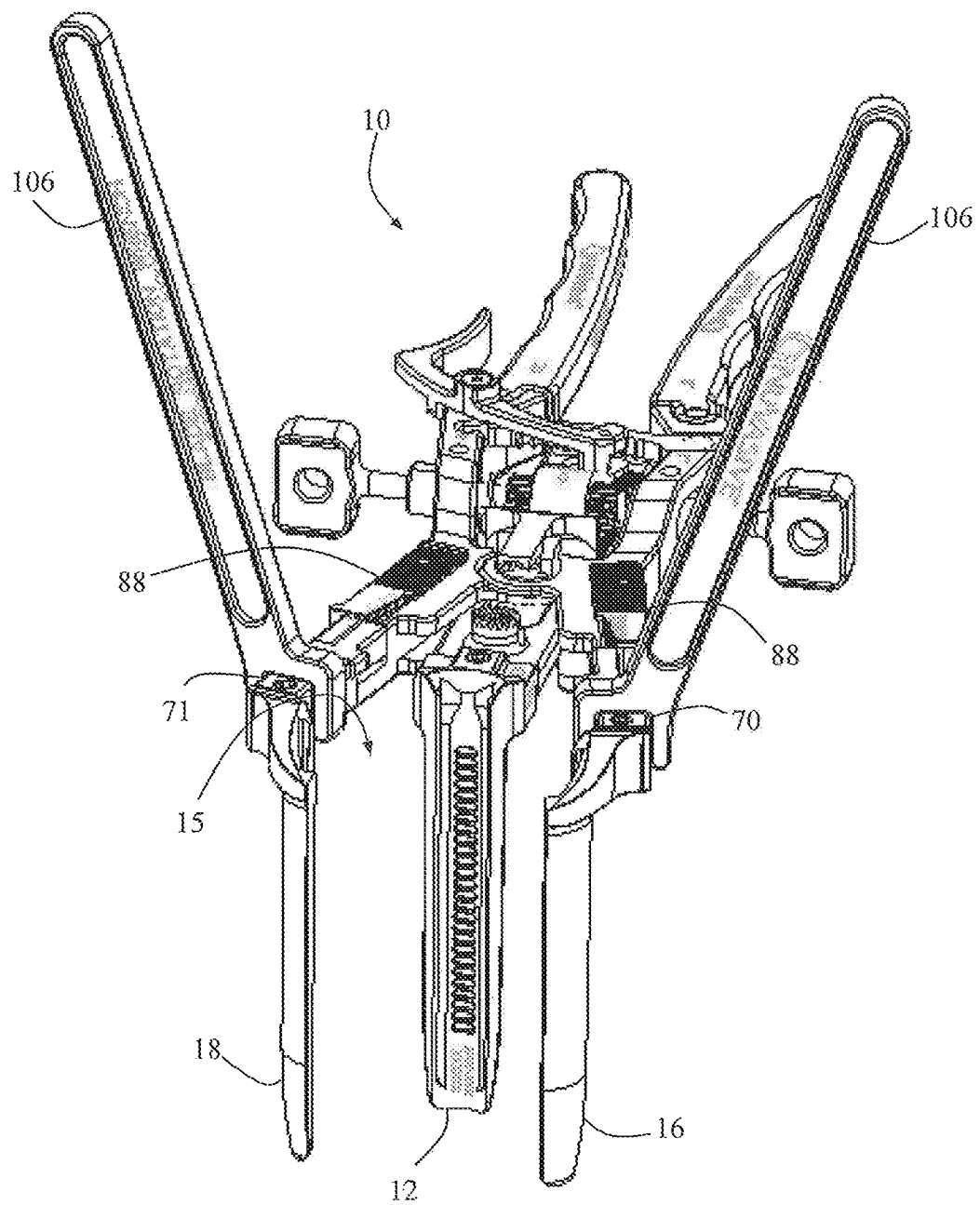
FIG. 24 is a perspective view of the tissue retraction assembly of FIG. 1 in conjunction with a pair of pivot wrenches before the blades have been pivoted.
Figure 56:
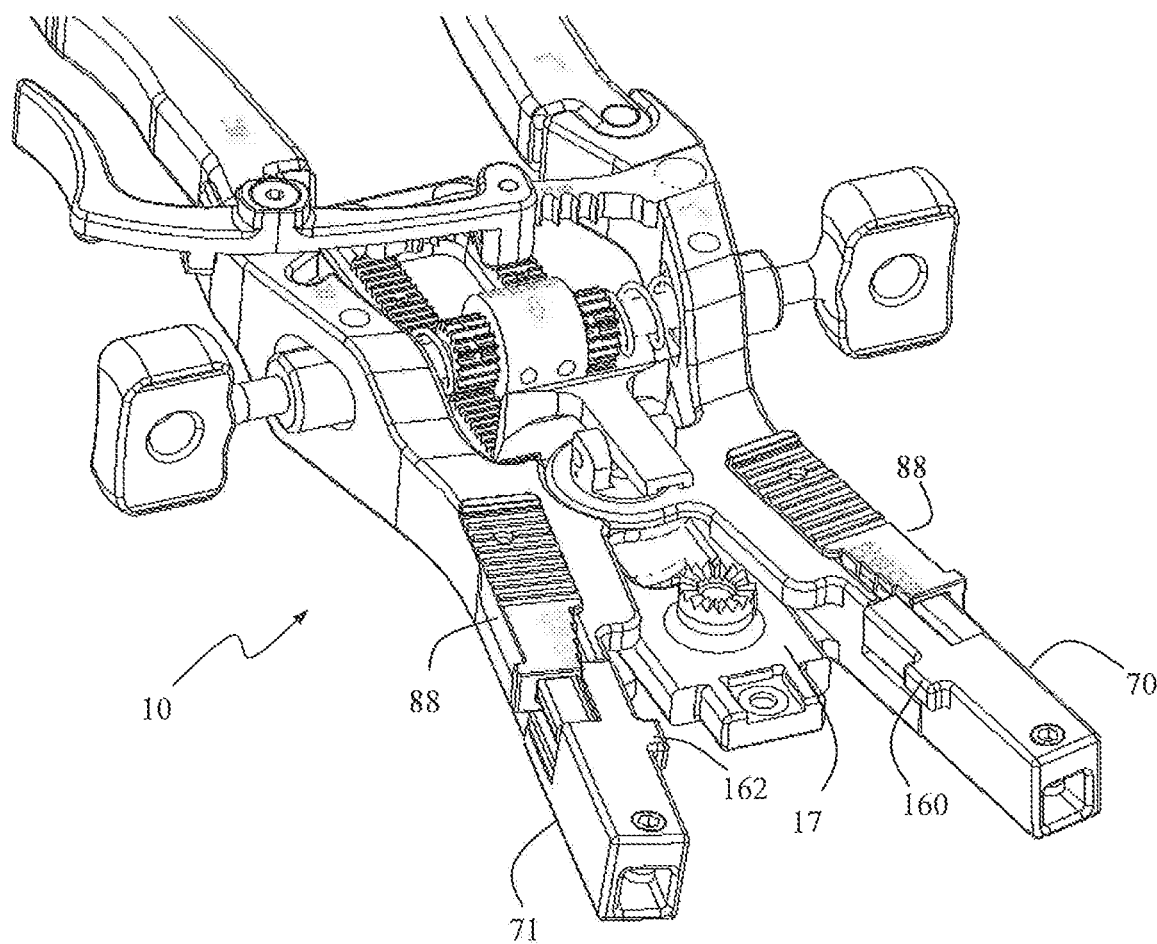
FIG. 56 is a perspective view of the handle assembly of FIG. 54 shown in a secondary open position.

Once the tissue retraction system 10 is fully in place and the sequential dilation system 50 has been removed as described above, the handle assembly 20 may be operated to move the first and second arm members 26, 28 into a second position shown generally in FIG. 56. In so doing, retractor blades 16, 18 are also moved into a second, "retracted" position. The presence of the patient's soft tissue defining the walls of the operative corridor is generally sufficient to maintain the retractor blades 16, 18 in the initial (e.g. generally vertical) alignment despite the fact that locking tabs 160, 162 are no longer engaged with translating member 17. At this point, the surgeon may elect to expand the operative corridor 15 by manually pivoting the retractor blades 16, 18 in a generally outward direction, using by way of example only either a pivot wrench 106 (FIGS. 24-26) and/or a blade expander 112 (FIGS. 31-33) as described above.

As mentioned above, any number of distraction components and/or retraction components (including but not limited to those described herein) may he equipped to detect the presence of (and optionally the distance and/or direction to) neural structures during tissue distraction and/or retraction. This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMC) system (that is, typically operated by a neurophysiologist). Such monitoring may also be carried out via the surgeon-driven EMG monitoring system shown and described in the commonly owned and co-pending Neuro-Vision PCT Applications referenced above. In any case (visual monitoring, traditional EMG and/or surgeon-driven EMG monitoring), the access system of the present invention may advantageously be used to traverse tissue that would ordinarily be deemed unsafe or undesirable, thereby broadening the number of manners in which a given surgical target site may be accessed.

Figure 57:
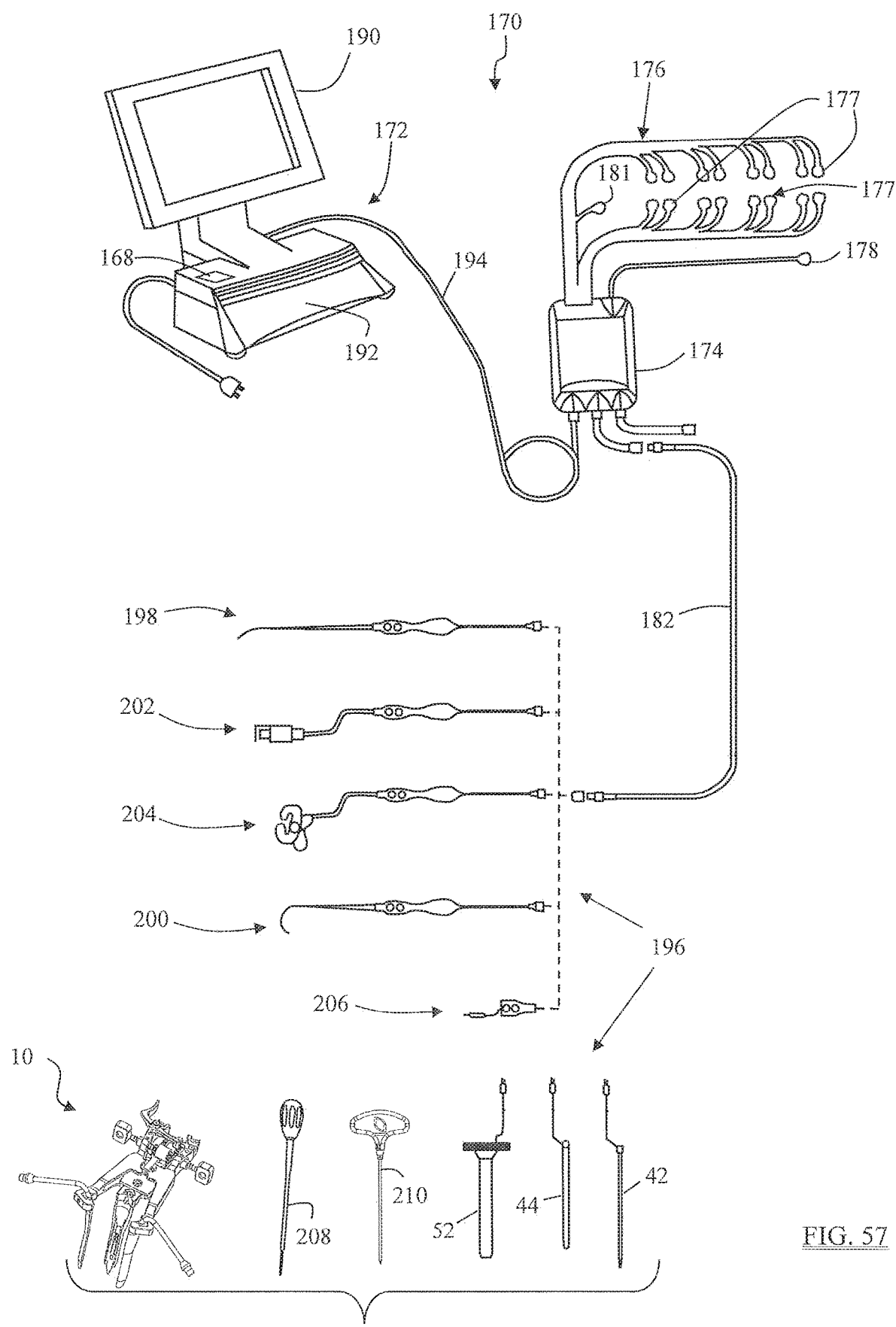
FIG. 57 is a perspective view of an exemplary nerve monitoring system capable of performing nerve monitoring before, during and after the creating of an operative corridor to a surgical target site using the surgical access system in accordance with the present invention.
Figure 58:
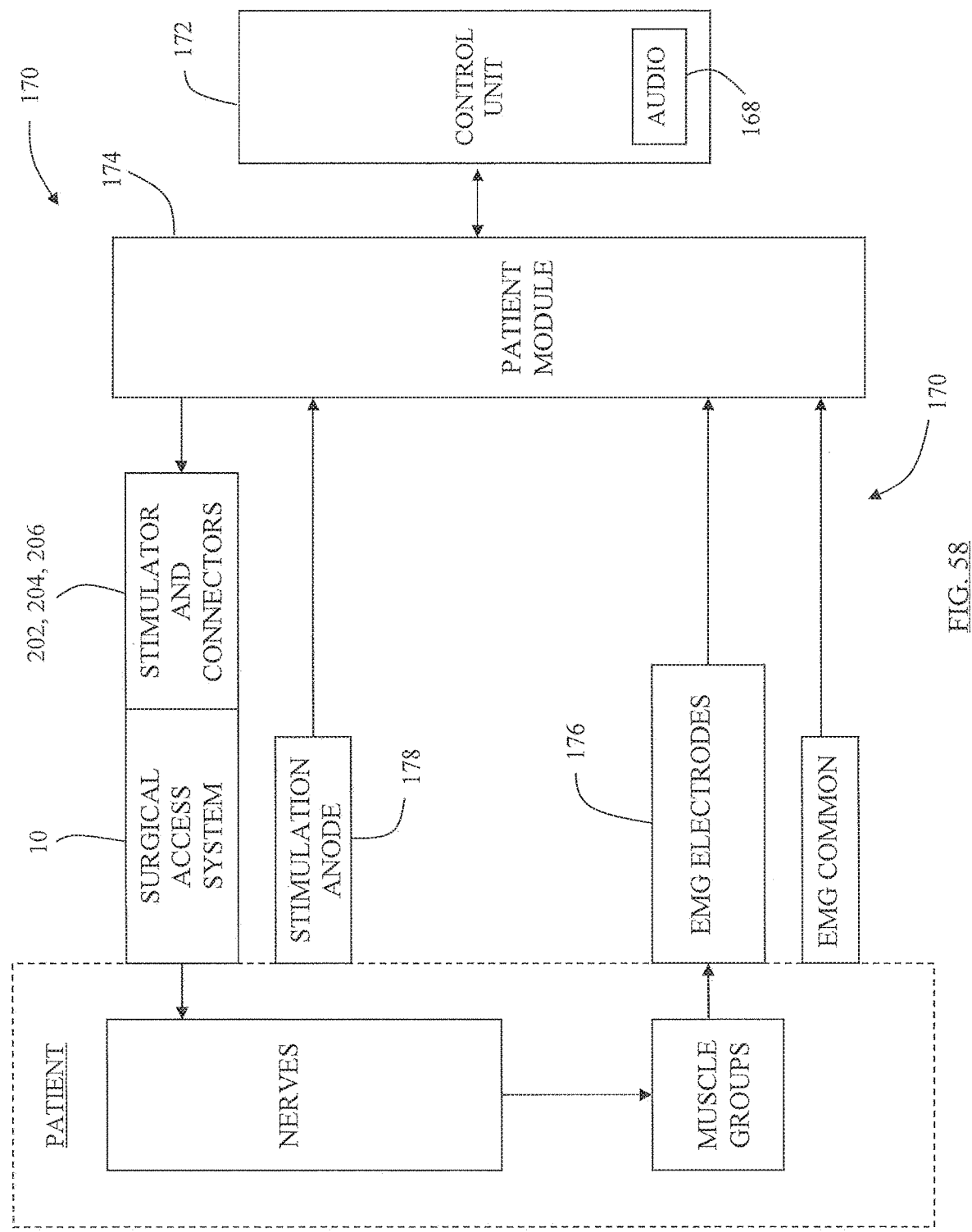
FIG. 58 is a block diagram of the nerve monitoring system shown in FIG. 57.

FIGS. 57-58 illustrate, by way of example only, a monitoring system 170 of the type disclosed in the NeuroVision PCT Applications suitable for use with the surgical access system 10 of the present invention. The monitoring system 170 includes a control unit 172, a patient module 174, and an EMG harness 176 and return electrode 178 coupled to the patient module 174, and a cable 182 for establishing electrical communication between the patient module 174 and any number of surgical accessories 196, including the surgical access system of the present invention (retractor assembly 10 of FIG. 1 and distraction assemblies 40, 50 of FIGS. 46-47, including K-wire 42, initial dilator 44 and sequentially dilating cannulae 52, 54). The surgical accessories 196 may further include, but are not necessarily limited to, devices for performing pedicle screw tests (such as a screw test probe 198), neural pathology monitoring devices (such as a nerve root retractor 200), coupling devices for electronically coupling surgical instruments to the system 170 (such as electric coupling devices 202, 204 and stimulator driver 206), and pilot hole forming components (such as a tap member 208, pedicle access probe 210, or other similar device). More specifically, this electrical communication can be achieved by providing, by way of example only, a hand-held stimulation driver 206 capable of selectively providing a stimulation signal (due to the operation of manually operated buttons on the hand-held stimulation controller 206) to one or more connectors (e.g., coupling devices 202, 204). The coupling devices 202, 204 are suitable to establish electrical communication between the hand-held stimulation controller 206 and (by way of example only) the stimulation electrodes on the K-wire 42, the dilators 44, 52, 54, the retractor blades 12, 16, 18 and/or the shim members 22, 24, 25, 60 (collectively "surgical access instruments").

In order to use the monitoring system 170, then, these surgical access instruments must be connected to at least one of coupling devices 202, 204 (or their equivalent), at which point the user may selectively initiate a stimulation signal (preferably, a current signal) from the control unit 172 to a particular surgical access instruments. Stimulating the electrode(s) on these surgical access instruments before, during and/or after establishing operative corridor will cause nerves that come into close or relative proximity to the surgical access instruments to depolarize, producing a response in a myotome associated with the innervated nerve.

The control unit 172 includes a touch screen display 190 and a base 192, which collectively contain the essential processing capabilities (software and/or hardware) for controlling the monitoring system 170. The control unit 172 may include an audio unit 168 that emits sounds according to a location of a surgical element with respect to a nerve. The patient module 174 is connected to the control unit 172 via a data cable 194, which establishes the electrical connections and communications (digital and/or analog) between the control unit 172 and patient module 174. The main functions of the control unit 172 include receiving user commands via the touch screen display 190, activating stimulation electrodes on the surgical access instruments, processing signal data according to defined algorithms, displaying received parameters and processed data, and monitoring system status and report fault conditions. The touch screen display 190 is preferably equipped with a graphical user interface (GUI) capable of communicating information to the user and receiving instructions from the user. The display 190 and/or base 192 may contain patient module interface circuitry (hardware and/or software) that commands the stimulation sources, receives digitized signals and other information from the patient module 174, processes the EMG responses to extract characteristic information for each muscle group, and displays the processed data to the operator via the display 190.

In one embodiment, the monitoring system 170 is capable of determining nerve direction relative to one or more of the K-wire 42, the dilators 44, 52, 54, the retractor blades 12, 16, 18 and/or the shim elements 22, 24, 25, 60 before, during and/or following the creation of an operative corridor to a surgical target site. Monitoring system 170 accomplishes this by having the control unit 172 and patient module 174 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 176. The nerve direction feature of the system 170 is based on assessing the evoked response of the various muscle myotomes monitored by the system 170 via the EMG harness 176.

By monitoring the myotomes associated with the nerves (via the EMG harness 176 and recording electrode 177) and assessing the resulting EMG responses (via the control unit 172), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 10 after the operative corridor has been established. In spinal surgery, for example, this is particularly advantageous in that the surgical access system 10 may be particularly suited for establishing an operative corridor to an intervertebral target site in a postero-lateral, trans-psoas fashion so as to avoid the bony posterior elements of the spinal column.

Figure 59:
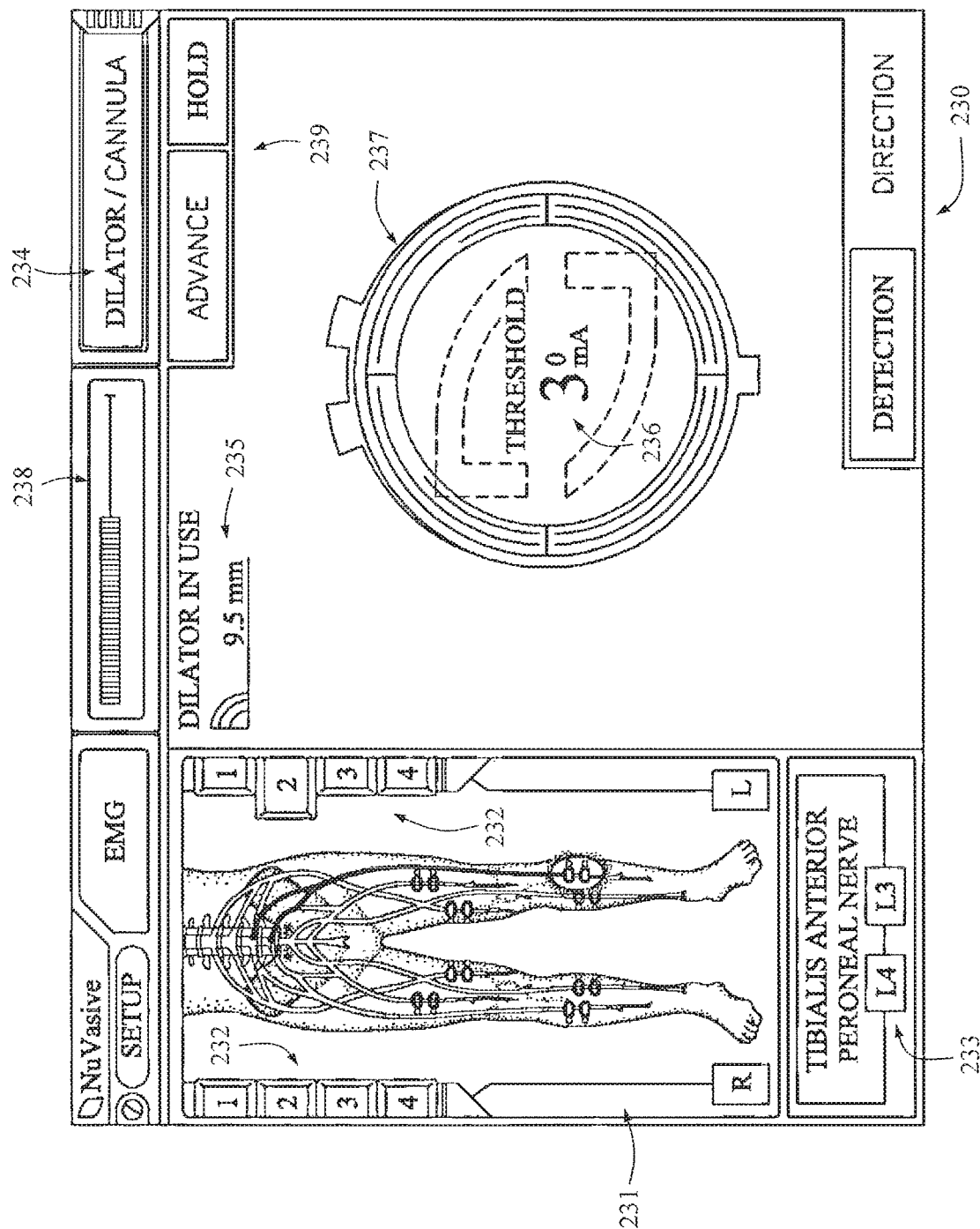
FIGS. 59-60 are screen displays illustrating exemplary features and information communicated to a user during the use of the nerve monitoring system of FIG. 57.
Figure 60:
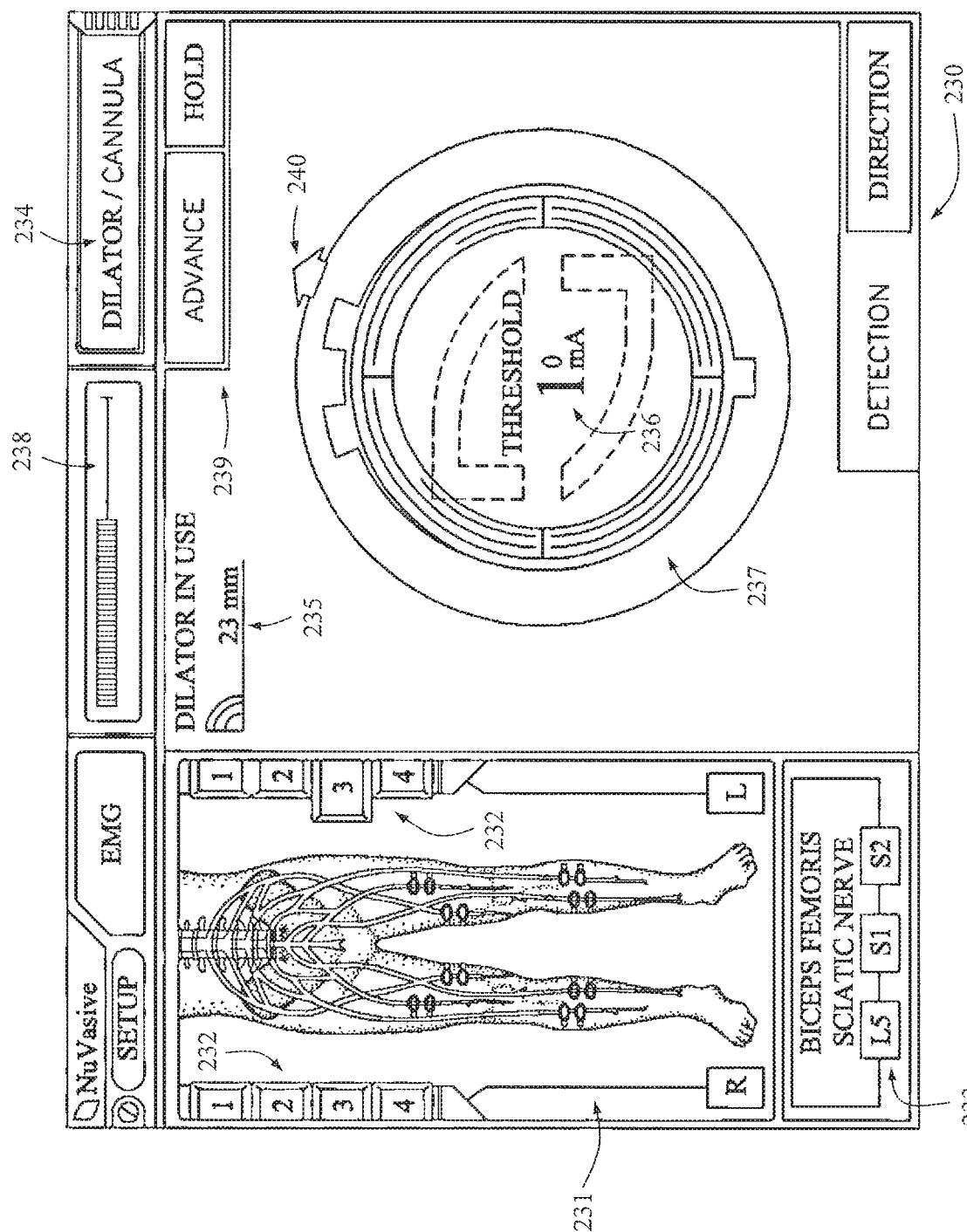

FIGS. 59-60 are exemplary screen displays (to be shown on the display 190) illustrating one embodiment of the nerve direction feature of the monitoring system shown and described with reference to FIGS. 57-58. These screen displays are intended to communicate a variety of information to the surgeon in an easy-to-interpret fashion. This information may include, but is not necessarily limited to, a display of the function 230 (in this case "DIRECTION"), a graphical representation of a patient 231, the myotome levels being monitored 232, the nerve or group associated with a displayed myotome 233, the name of the instrument being used 234 (in this case, a dilator 52, 54), the size of the instrument being used 235, the stimulation threshold current 236, a graphical representation of the instrument being used 237 (in this case, a cross-sectional view of a dilator 52, 54) to provide a reference point from which to illustrate relative direction of the instrument to the nerve, the stimulation current being applied to the stimulation electrodes 238, instructions for the user 239 (in this case, "ADVANCE" and/or "HOLD"), and (in FIG. 60) an arrow 240 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 234), it is to be readily appreciated that the present invention is deemed to include providing similar information on the display 190 during the use of any or all of the various instruments forming the surgical access system 10 of the present invention, including the distraction assembly 40 (i.e. the K-wire 42 and dilators 44, 52, 54) and/or the retractor blades 12, 16, 18 and/or the shim elements 22, 24, 25, 60.

As evident from the above discussion and drawings, the present invention accomplishes the goal of gaining access a surgical target site in a fashion less invasive than traditional "open" surgeries and, moreover, does so in a manner that provides the ability to access such a surgical target site regardless of the neural structures required to be passed through (or near) in order to establish an operative corridor to the surgical target site. The present invention furthermore provides the ability to perform neural monitoring in the tissue or regions adjacent the surgical target site during any procedures performed after the operative corridor has been established. The surgical access system of the present invention can be used in any of a wide variety of surgical or medical applications, above and beyond the spinal applications discussed herein. Such spinal applications may include any procedure wherein instruments, devices, implants and/or compounds are to be introduced into or adjacent the surgical target site, including but not limited to discectomy, fusion (including PDF, ALIF, TLIF and any fusion effectuated via a lateral or far-lateral approach and involving, by way of example, the introduction and/or removal of bone products (such as allograft or autograft) and/or devices having ceramic, metal and/or plastic construction (such as mesh) and/or compounds such as bone morphogenic protein), total disc replacement, etc. . . . ).

Moreover, the surgical access system of the present invention opens the possibility of accessing an increased number of surgical target sites in a "less invasive" fashion by eliminating or greatly reducing the threat of contacting nerves or neural structures while establishing an operative corridor through or near tissues containing such nerves or neural structures. In so doing, the surgical access system of the present invention represents a significant advancement capable of improving patient care (via reduced pain due to "less-invasive" access and reduced or eliminated risk of neural contact before, during, and after the establishment of the operative corridor) and lowering health care costs (via reduced hospitalization based on "less-invasive" access and increased number of suitable surgical target sites based on neural monitoring). Collectively, these translate into major improvements to the overall standard of care available to the patient population, both domestically and overseas.

What is claimed is:

1. A system for accessing a surgical target site, comprising: a retractor assembly having three blades capable of being advanced to said surgical target site along a longitudinal axis while in a closed position in which each of said three blades abuts the other two, and thereafter opened to create an operative corridor to said surgical target site, wherein at least one of said blades is pivotally coupled to a handle assembly to pivot about a pivot axis that is orthogonal to the longitudinal axis, and wherein at least two of the blades are arcuate in cross-section, wherein one of the three blades is a posterior blade rigidly coupled to a translating member, wherein the translating member is coupled to the handle assembly via a linkage assembly configured to move the translating member in a linear fashion with respect to the handle assembly, the linkage assembly comprising a roller member, whereby rotating the roller member in a first rotational direction drives the translating member and posterior blade away from the handle assembly, and rotating the roller member in a second rotational direction drives the translating member and posterior blade toward the handle assembly, wherein movement of the translating member and posterior blade toward or away from the handle assembly can be performed without moving the other blades with respect to the handle assembly.

2. The system of claim 1, including a distraction assembly for creating a distraction corridor to said surgical target site prior to advancing said retractor blades to said surgical target site.

3. The system of claim 2, wherein said distraction assembly includes an initial distraction assembly including a K-wire and at least one dilator capable of being slidably passed over said K-wire to perform said initial distraction.

4. The system of claim 3, including a secondary distraction assembly for distracting said initial distraction corridor to a secondary distraction corridor, said retractor blades being advanced through said secondary distraction corridor to said surgical target site.

5. The system of claim 3, wherein said K-wire has a first stimulation electrode at a distal tip of the K-wire.

6. The system of claim 2, wherein said distraction assembly includes at least one stimulation electrode.

7. The system of claim 6, further comprising a control unit capable of electrically stimulating said at least one stimulation electrode, sensing a response of a nerve depolarized by said stimulation, determining a direction from said distraction assembly to the nerve based upon the sensed response, and communicating said direction to a user.

8. The system of claim 7, further comprising an electrode configured to sense a neuromuscular response of a muscle coupled to the depolarized nerve, the electrode being operable to send the response to the control unit.

9. The system of claim 8, wherein the control unit comprises a display operable to display an electromyographic (EMG) response of the muscle.

10. The system of claim 7, further comprising a handle coupled to said distraction assembly, the handle having at least one button for initiating the electrical stimulation from said control unit to said at least one stimulation electrode.

11. The system of claim 7, wherein the control unit comprises a touch-screen display operable to receive commands from a user.

12. The system of claim 11, wherein the at least one stimulation electrode is positioned near a distal end of the distraction assembly.

13. The system of claim 1, wherein at least one of said retractor blades includes at least one stimulation electrode.

14. The system of claim 13, further comprising a control unit capable of electrically stimulating said at least one stimulation electrode, sensing a response of a nerve depolarized by said stimulation, determining a direction from at least one of said retractor blades to the nerve based upon the sensed response, and communicating said direction to a user.

15. The system of claim 14, further comprising an electrode configured to sense a neuromuscular response of a muscle coupled to said depolarized nerve, the electrode being operable to send the response to the control unit.

16. The system of claim 15, wherein the control unit comprises a display operable to display an electromyographic (EMG) response of the muscle.

17. The system of claim 14, further comprising a handle coupled to at least one of said retractor blades, the handle having at least one button for initiating the electrical stimulation from said control unit to said at least one stimulation electrode.

18. The system of claim 14, wherein the control unit comprises a touch-screen display operable to receive commands from a user.

19. The system of claim 13, wherein the at least one stimulation electrode is positioned near a distal end of at least one of said retractor blades.

20. The system of claim 1, wherein said system for establishing an operative corridor to a surgical target site is configured to access a spinal target site.

21. The system of claim 1, wherein said system for establishing an operative corridor to a surgical target site is configured to establish said operative corridor via a lateral, trans-psoas approach.

22. The system of claim 1, wherein at least one of the retractor blades is constructed from a material that is at least partially radiolucent.

23. The system of claim 1, wherein the handle assembly is equipped with a locking mechanism to selectively lock the blades in a selected position.

24. The system of claim 23, wherein the locking mechanism allows the blades to be locked in any of a variety of predetermined angles.

25. The system of claim 24, wherein the locking mechanism includes a rotating arm section coupled to the handle having a plurality of pre-selected stops corresponding to said predetermined angles.

26. The system of claim 24, wherein the predetermined angles include the range of 0 to 20 degrees relative to when the blades are in the closed position.

27. The system of claim 1, further comprising at least one tool for pivoting the at least one blade, wherein the at least one tool comprises at least one of a wrench and a blade expander.

28. The system of claim 1, further comprising at least one of a blade extender and a blade shim configured to be releasably coupled to at least one of the plurality of blades.

29. The system of claim 28, wherein at least one of the blade extender and the blade shim include a lateral extension to increase the width of the blade extender and blade shim.

30. The system of claim 28, wherein at least one of the blade extender and the blade shim include a distal extension to increase the length of the blade extender and blade shim.

* * * * *